United States Patent
Dublanchet et al.

(10) Patent No.: US 11,141,368 B2
(45) Date of Patent: *Oct. 12, 2021

(54) COSMETIC COMPOSITION, COSMETIC TREATMENT METHOD, KIT, AND COMPOUND

(71) Applicant: L'OREAL, Paris (FR)

(72) Inventors: Anne-Claude Dublanchet, Antony (FR); Christian Blaise, Saint Mande (FR); Abel Messavussu, Fontenay sous Bois (FR)

(73) Assignee: L'OREAL, Paris (FR)

( * ) Notice: Subject to any disclaimer, the term of this patent is extended or adjusted under 35 U.S.C. 154(b) by 193 days.

This patent is subject to a terminal disclaimer.

(21) Appl. No.: 15/979,955

(22) Filed: May 15, 2018

(65) Prior Publication Data

US 2018/0256476 A1    Sep. 13, 2018

Related U.S. Application Data

(63) Continuation of application No. 13/520,409, filed as application No. PCT/FR2011/050005 on Jan. 4, 2011, now Pat. No. 10,813,866.

(60) Provisional application No. 61/292,255, filed on Jan. 5, 2010.

(30) Foreign Application Priority Data

Jan. 4, 2010   (FR) ..................................... 1050003

(51) Int. Cl.
  *A61K 8/58*    (2006.01)
  *A61K 8/49*    (2006.01)
  *A61Q 5/12*    (2006.01)
  *C07D 239/47*  (2006.01)

(52) U.S. Cl.
  CPC ............. *A61K 8/585* (2013.01); *A61K 8/49* (2013.01); *A61K 8/4953* (2013.01); *A61Q 5/12* (2013.01); *C07D 239/47* (2013.01)

(58) Field of Classification Search
  CPC ........ A61K 8/585; A61K 8/49; A61K 8/4953; A61Q 5/12; C07D 239/47
  See application file for complete search history.

(56) References Cited

U.S. PATENT DOCUMENTS

| | | | |
|---|---|---|---|
| 6,320,018 | B1 | 11/2001 | Sijbesma et al. |
| 10,813,866 | B2 * | 10/2020 | Dublanchet .......... A61K 8/4953 |
| 2004/0034190 | A1 | 2/2004 | Janssen et al. |
| 2004/0131932 | A1 | 7/2004 | Hamada et al. |
| 2004/0161394 | A1 | 8/2004 | Mougin |
| 2005/0031566 | A1 | 2/2005 | Cooper |
| 2005/0153194 | A1 | 7/2005 | Kimura et al. |
| 2006/0018856 | A1 | 1/2006 | Bosman et al. |
| 2007/0008678 | A1 | 1/2007 | Fresard et al. |
| 2007/0093639 | A1 | 4/2007 | Jassen et al. |
| 2008/0096104 | A1 | 4/2008 | Kim |
| 2009/0081145 | A1 | 3/2009 | Knorr et al. |
| 2009/0130172 | A1 | 5/2009 | Dankers et al. |
| 2010/0242188 | A1 | 9/2010 | Daubresse et al. |
| 2011/0189118 | A1 | 8/2011 | Mougin et al. |

FOREIGN PATENT DOCUMENTS

| | | |
|---|---|---|
| EP | 1120841 A1 | 8/2001 |
| EP | 1797867 A1 | 6/2007 |
| EP | 1970099 A2 | 9/2008 |
| EP | 1985445 A1 | 10/2008 |
| FR | 2862218 A1 | 5/2005 |
| JP | 11-354097 A | 12/1999 |
| JP | 2000-106164 A | 4/2000 |
| JP | 2005300817 A | 10/2005 |
| WO | WO-2004016598 A1 | 2/2004 |
| WO | WO2008/059125 | 5/2008 |
| WO | WO2008063057 | 5/2008 |
| WO | WO2010001041 | 1/2010 |

OTHER PUBLICATIONS

Sontjens et al., "Stability and Lifetime of Quadruply Hydrogen Bonded 2-Ureido-4[1H]-pyrimidinone Dinmers", J. Am. Chem. Soc, 2000, 122, 7487-7493.

Lange et al., "Hydrogen-Bonded Supramolecular Polymer Networks", Journal of Polymer Science: Part A: Polymer Chemistry, vol. 37, 1999, pp. 3657-3670; XP002605245.

Rieth et al., "Polymerization of ureidopyrimidinone-functionalized olefines by using late-transition metal Ziegler-Natta catalysts: synthesis of thermoplastic elastomeric polyolefins", Angew. Chem. Int. Ed., 2001, 40, No. 11 pp. 2153-2156, XP002260388.

(Continued)

*Primary Examiner* — Matthew P Coughlin
*Assistant Examiner* — Thurman Wheeler
(74) *Attorney, Agent, or Firm* — Polsinelli PC

(57) ABSTRACT

The invention relates to a cosmetic composition, especially a hair composition, and to a method for the cosmetic treatment of keratin materials, especially of the hair, employing compounds of formula:

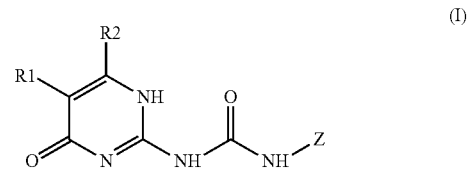

(I)

in which Z represents (i) a hydrogen atom, (ii) a linear or branched C1 to C32 (saturated) alkyl radical; (iii) a linear or branched C2 to C32 (unsaturated) alkene radical, comprising one or two C=C double bonds; (iv) an aryl-substituted alkyl radical; said radicals being optionally substituted and/or interrupted.

17 Claims, No Drawings

(56) References Cited

OTHER PUBLICATIONS

Sijbesma et al., "Reversible Polymers Formed from Self-Complementary Monomers Using Quadruple Hydrogen Bonding", Science, vol. 278, Nov. 28, 1997, pp. 1601-1604, XP002605246.

Beijer et al., "Strong Dimerization of Ureidopyrimidones via Quadruple Hydrogen Bonding", J. Am. Chem. Soc., 1998, 120, 6761-6796, XP002605247.

Gruijters et al., "Catalyst Recycling via Hydrogen-Bonding-Based Affinity Tags", Org. Lett., vol. 8, No. 15, 2008, 3163-3166, XP002605248.

Kreutzberger et al., "2-Ureido-4(3H)-pyrimidinone", Arch, Pharm., vol. 314, No. 1, 1981, 34-41, XP002605249.

Franz Pohl, "Untersuchungen aus dem organ.-chem. Laboratorium der Technischen Hochschule zu Dresden, LXXXVII. Zur Kenntnis des Dicyandiamids", Journal für Praktische Chemie, vol. 77, No. 1, May 14, 1908, pp. 533-548, XP002605250.

Arrachart et al., "Nanostructuring of Hybrid Silicas through a Self-Recognition Process", Chem. Eur. J., 2009, 15, 5002-5005, XP002605251.

Han et al., "Fabrication of Superhydrophobic Surface from a Supramolecular Organosilane with Quadruple Hydrogen Bonding", J. Am. Chem. Soc., 2004, 126, 4796-4797, XP002605252.

Guan et al., "Modular Domain Structure: A Biomimetic Strategy for Advanced Polymeric Materials", J. Am. Chem. Soc., 2004, 126, 2058-2065, XP002605253.

Database Registry [Online] Chemical Abstracts Service, Columbus, Ohio, US, Jun. 25, 2003, XP002603188.

Zou et al., "Tunable Complex Stability in Surface Molecular Recognition Mediated by Self-Complementary Quadruple Hydrogen Bonds", Langmuir 2003, 19, 8618-8621, XP002605254.

Wang et al., "Selective Rearrangements of Quadruply Hudrogen-Bonded Dimer Driven by Donor-Acceptor Interaction", Chem. Eur. J., 2003, 9, 2904-2913, XP002605255.

Vippagunta, Advanced Drug Delivery Reviews, May 16, 2001, pp. 3-26.

\* cited by examiner

COSMETIC COMPOSITION, COSMETIC TREATMENT METHOD, KIT, AND COMPOUND

CROSS REFERENCE TO RELATED APPLICATIONS

This application is a Continuation of application Ser. No. 13/520,409, having a filing date of Jan. 4, 2011, which is the National Phase filing under 35 U.S.C. § 371 of PCT/FR2011/050005 filed on Jan. 4, 2011; and this application claims priority to Application No. 1050003 filed in France on Jan. 4, 2010, and this application claims the benefit of U.S. Provisional Application No. 61/292,255 filed on Jan. 5, 2010, under 35 U.S.C. § 119; the entire contents of all are hereby incorporated by reference.

The present invention relates to a method for the cosmetic treatment of keratin materials, especially of the hair, using a composition comprising compounds capable of forming hydrogen bonds, and also to the cosmetic compositions thus prepared, and to a kit comprising this composition.

In the cosmetics industry, there is a constant desire to improve the properties of keratin materials and to combat damage, such as external attacks, for instance pollution and ultraviolet radiation, or chemical attacks, for instance those caused by oxidizing, reducing or alkaline dyeing or permanent-waving treatments. Among the damage suffered by the hair, mention may especially be made of the increased hydrophilic nature, the loss or the detachment of some of the scales, and difficulties in disentangling.

In order to improve the properties of the hair, it is known practice to use compositions containing cosmetic active agents in order to provide the keratin materials, such as the hair, with all the beneficial effects associated with these cosmetic active agents. However, the persistence and therefore the effectiveness of these active agents are not sufficient, since they can be easily removed with shampoo, or else they do not form a homogeneous deposit at the surface of the hair.

The objective of the present invention is to propose a cosmetic composition capable of being used for the cosmetic treatment of the hair, and of giving the hair long-lasting cosmetic properties.

Indeed, it has been observed that compounds comprising entities capable of forming physical interactions with one another can give the hair advantageous cosmetic qualities. These compounds are especially characterized by the presence of at least one entity capable of giving at least 3 hydrogen bonds, in particular 4 hydrogen bonds, and also by their low mass.

One subject of the present invention is therefore a cosmetic composition comprising, in a cosmetically acceptable medium, at least one compound of formula (I) as defined below.

Another subject of the invention is a method for the cosmetic treatment of keratin materials, consisting in applying such a cosmetic composition to said keratin materials.

Another subject of the invention is a kit comprising said composition.

Particular compounds, of formula (Ia), constitute yet another subject of the invention.

It has been observed that depositing a compound according to the invention onto the skin or the hair or causing a compound according to the invention to penetrate into the hair makes it possible to provide the hair with a beneficial effect. Without being bound by the present explanation, it is possible to imagine that ureidopyrimidone entities are capable of generating, in situ in or on the hair, a crosslinked network by physical associations between molecules. When deposited on the hair or the skin, said compound becomes involved in and trapped in a crosslinked deposit, which increases its persistence, in particular with respect to sebum, water and shampoo.

Furthermore, since the crosslinking is a physical crosslinking, it is possible for the effect to be persistent while at the same time allowing the compound to be removed during makeup removal. The removal of the deposit may consist especially of rinsing with a cleansing composition applied at room temperature or at a temperature above 25° C., or through the use of a makeup remover, or by using any known hydrogen bond breaker.

Many compounds that incorporate ureido-pyrimidone (UPY) units have been described in the literature and studied for their self-assembly property by fundamental research laboratories. However, none of these documents describes the application of these compounds to keratin materials, nor even their possible use for strengthening said materials.

In the cosmetic field, mention may be made of WO 02/098377 which describes, in a general manner, compounds with UPY units for cosmetic applications to the skin and the hair. Mention may also be made of WO 2003/032929 which describes the preparation of supramolecular polymers and the use thereof in hair applications. Mention may also be made of WO 2004/016598 which describes the preparation of supramolecular polymers and the use thereof in various applications, including cosmetic applications. Alternatively, mention may be made of WO 2005/042641 which describes the preparation of supramolecular polymers, especially of polyurethane type, and the use thereof in various applications, including cosmetic applications.

In all of these documents, the compounds described are polymers, therefore compounds of high molecular weight, which will not therefore penetrate into the hair in order to provide it with beneficial properties, in particular in terms of protection of the hair.

The present invention may also make it possible to hydrate and strengthen or even repair keratin materials, and to provide long-lasting softness to them, such that the effect remains perceptible after at least one shampoo wash.

The expression "strengthening of keratin materials" is understood to mean in particular an improvement in the mechanical properties which may result in:
- an increase in their rigidity, which gives them greater strength and body; or else
- a decrease in their deformation, in particular under wet conditions, which allows the hair to readily return to its initial shape once dried, and results in an improvement in the dynamics of the hair; or else
- a better resistance to tensile mechanical forces which are applied thereto, for example during combing, and which can lead to breaking of the hair;
- a decrease in its porosity or in its swelling in water. Indeed, it is known that hair damaged by oxidizing, reducing or alkaline treatments is more porous than undamaged hair, which results in a faster diffusion of water further into the core and has the effect of increasing the diameter of the hair in a wet environment (The Science of Hair Care, p. 416, $2^{nd}$ edition, ed. C. Bouillon, J. Wilkinson, 2005).

Furthermore, it is possible to generate a network, in situ, in the hair, which will make it possible to provide the hair with protection or repair properties, following a dyeing, bleaching, permanent-waving, smoothing or straightening treatment for example. Creating this crosslinked network in the hair also makes it possible to avoid premature bleeding of a dye.

The compounds according to the invention may therefore both coat the hair, and therefore provide in particular strengthening properties, and also penetrate into the hair and provide, in situ, protection or repair properties in particular.

Moreover, it has been observed that the use of compounds according to the invention on hair straightened by an alkaline treatment makes it possible to transform the hair in a manner that is resistant to shampoo washes, in other words to increase the straightening performances without increasing the porosity of said hair; this effect still remaining perceptible after 5 shampoo washes.

It has also been observed that the application of certain compounds according to the invention to damaged, and therefore hydrophilic hair has the effect of repairing the surface of said hair by rendering it lastingly hydrophobic, and of facilitating the disentagling thereof in a wet environment.

Furthermore, it has been observed that the association of certain compounds according to the invention, applied in the form of 3 successive low concentration (0.1% AM) applications to damaged hair, previously reduced with a 0.2M thioglycolic acid treatment has the effect of re-establishing the modulus of rigidity of the hair.

The compounds according to the invention may therefore be applied before, during or after a cosmetic hair dyeing, bleaching, permanent-waving, straightening or smoothing treatment, or else as a maintenance treatment for hair damaged by external attacks such as UV, pollution, repeated brushing and chlorinated water.

The compound capable of being employed within the context of the invention therefore corresponds to the formula (I), salts thereof, addition salts thereof, isomers thereof, solvates thereof, especially hydrates thereof, the tautomeric forms being included:

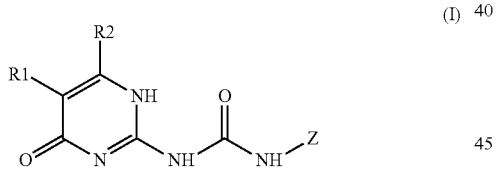
(I)

in which:

R1 and R2, independently of one another, represent H, —OH, —NRR' (with R, R', which may be identical or different, being H or a linear or branched C1-C12, preferably C1-C4 alkyl radical, and better still a methyl or ethyl radical); or a linear, branched and/or cyclic, saturated or unsaturated, optionally aromatic, C1-C18, preferably C1-C12 carbon-based group, especially an alkyl group, which may contain one or more O, N and/or S heteroatoms, especially OH, COOH and/or NRR'.

The radicals R1 and R2 may especially be chosen from:
H;
$NH_2$;
a C1-C18 alkyl group, optionally substituted with one or more $NH_2$, COOH and/or OH functions;
a C4-C12 cycloalkyl group, optionally substituted with one or more $NH_2$, COOH and/or OH functions;
a C4-C12 aryl group, optionally substituted with one or more $NH_2$, COOH and/or OH functions; and/or optionally substituted with one or more PEG groups of formula —$(CH_2CH_2O)_m$— with m=2 to 15;
a C1-C4 alkoxy group;
an aryl(C1-C4)alkoxy group; optionally substituted with one or more $NH_2$, COOH and/or OH functions.

Preferably, R1 represents H.

Preferably, R2 represents H, $CH_3$, $O_7H_{15}$, $C_{13}H_{27}$ or aryl.

Preferentially, R1=H and R2=methyl.

Z represents a monovalent radical chosen from:

(i) a hydrogen atom, (ii) a linear or branched C1 to C32, especially C2-C24 or even C3-C18, better still C4-C12 (saturated) alkyl radical;

(iii) a linear or branched C2 to C32, especially C2-C24 or even C3-C18 (unsaturated) alkene radical, comprising one or two C=C double bonds;

(iv) a C1-C32, especially C2-C24, or even C3-C18, better still C4-C12 alkyl radical, substituted with a C6-C10, especially C6-C8 aryl; in particular phenyl;

it being possible for said radicals to optionally be substituted with 1 to 8, especially 2 to 6 or even 3 to 5 groups chosen from —OH, —OR, —SH, —SR, —$SO_3H$, —$SO_3R$, —$SO_2NRR'$, —COOH, —COOR, —CONRR', —NR—C(O)—NRR', —NRR' and —N'RR'R", with R, R' and R"=H or C1-C6 alkyl, especially methyl; and the substituents of formula (a) to (h) below:

(a)

(b)

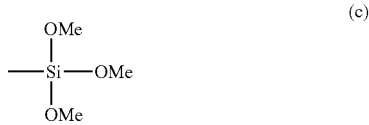
(c)

(d)

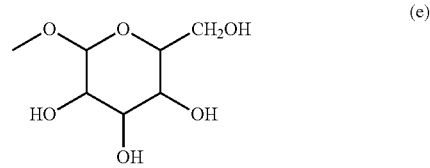
(e)

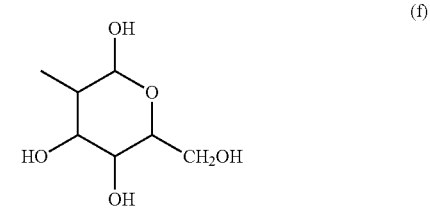
(f)

-continued

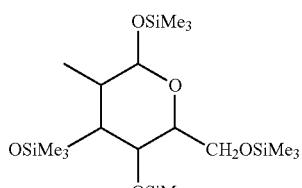

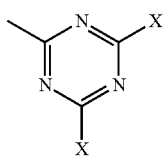

(X = halogen, especially Cl)

and/or it being possible for said radicals to optionally comprise 1 to 8, especially 2 to 6 or even 3 to 5 divalent groups chosen from, alone or as a mixture, —S—, S(O), SO₂, —NH— (or =NH), —O—, —C(O)—, —C(=NH)—, —N⁺(CH₃)₂-An⁻ (An⁻: anion); or else —N= (trivalent).

For the sake of clarity, it is specified that the Z radical cannot comprise the group:

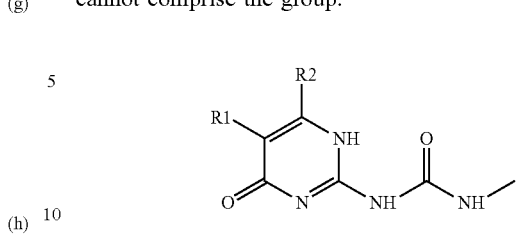

Preferably, the Z radical comprises 0 to 12 heteroatoms, especially 1 to 10, or even 2 to 6 heteroatoms.

Preferably, the Z radical, when it is substituted, is substituted by 1 to 8, especially 2 to 6, or even 3 to 5 groups chosen from —OH, —SH, —SO₃H, —COOH, —NRR' and —N'RR'R", with R, R' and R"=H or C1-C6 alkyl, especially methyl; and the substituents of formula (a) to (h).

Preferably, the Z radical, when it is interrupted, is interrupted by 1 to 8, especially 2 to 6, or even 3 to 5 divalent groups chosen from, alone or as a mixture, —S—, —NH— (or =NH), —O—, —C(O)—, —C(=NH)—, —N⁺(CH₃)₂—.

Among the compounds of formula (I) that are particularly preferred, mention may be made of the following compounds:

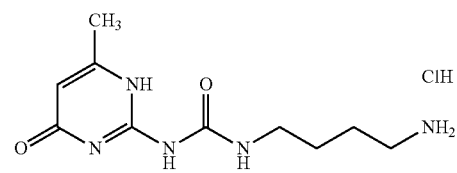

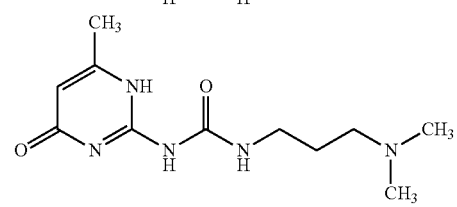

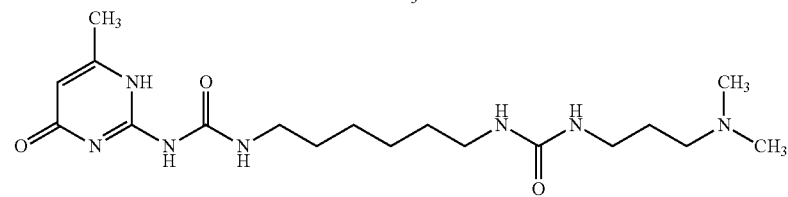

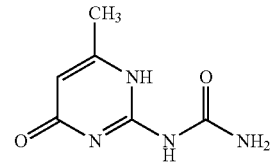

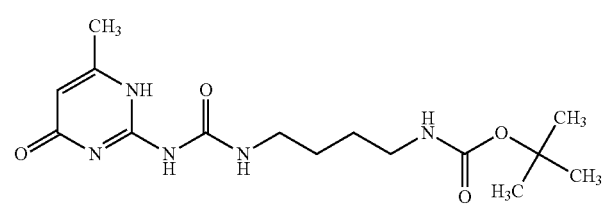

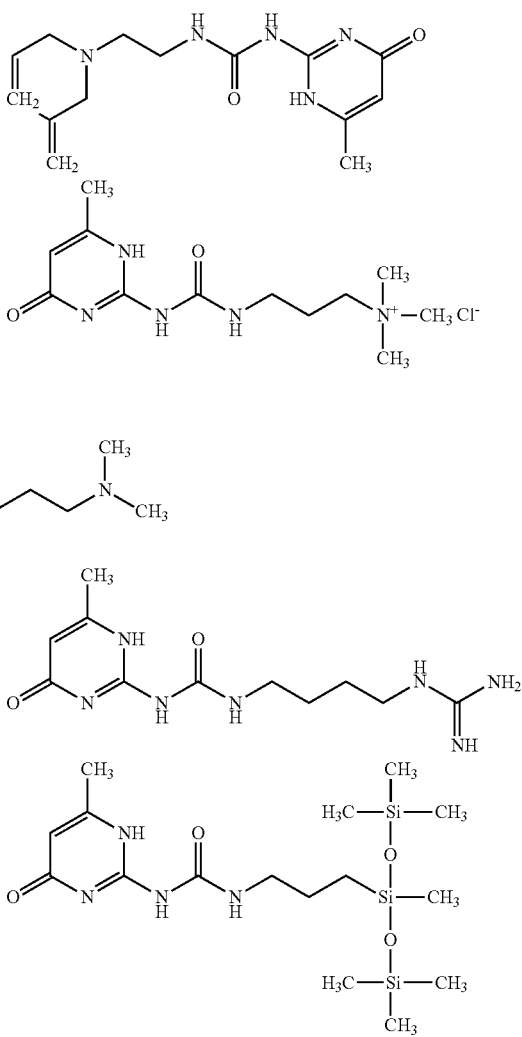

-continued
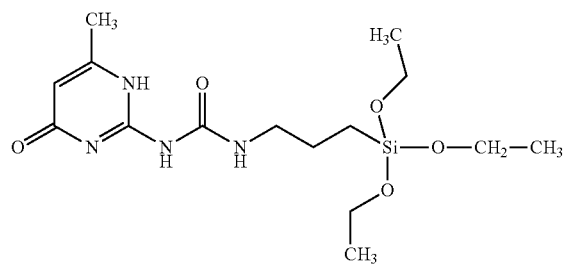
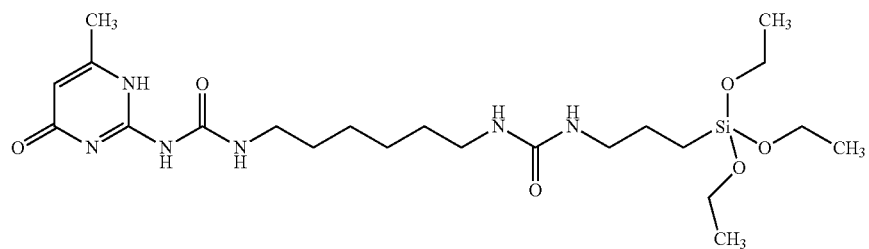
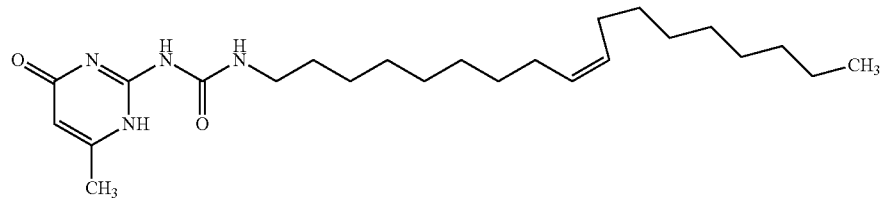
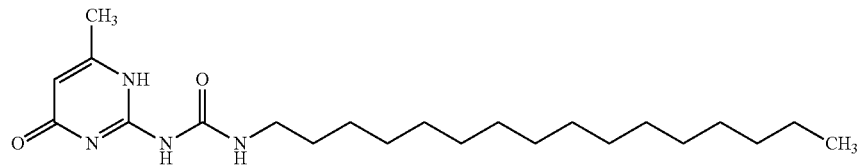
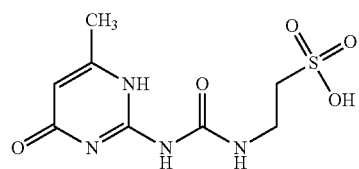
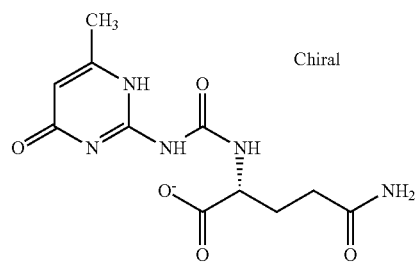
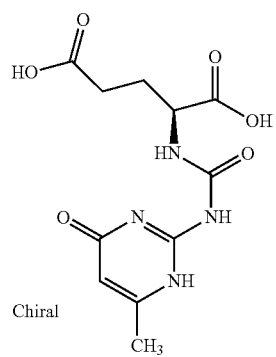
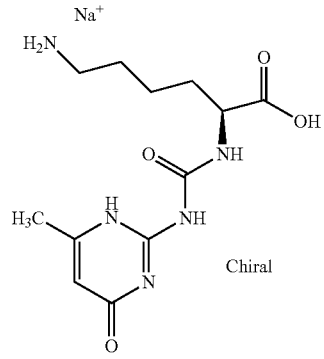

9
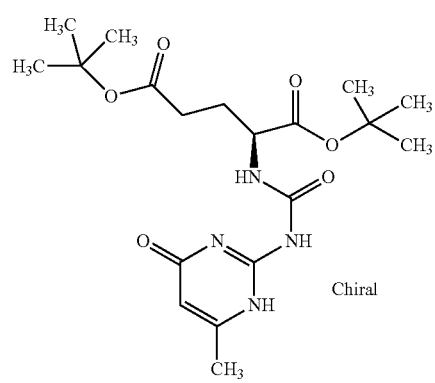
-continued
10
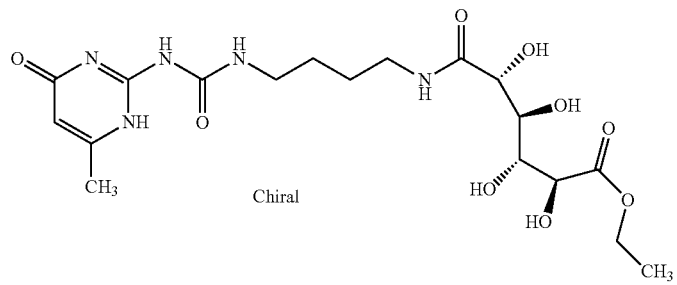
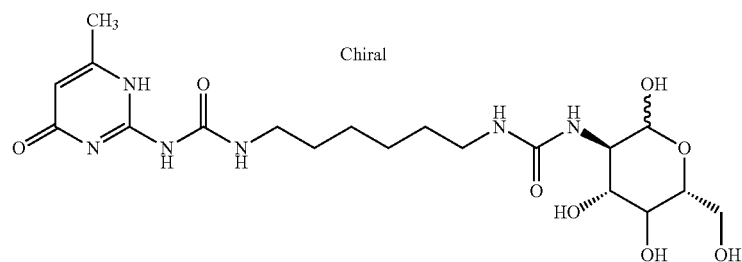
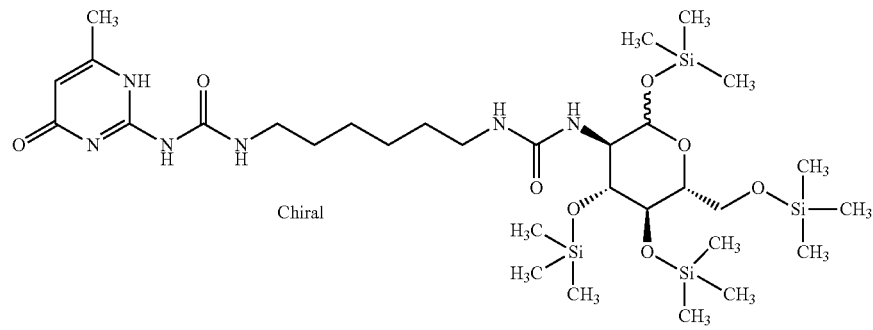
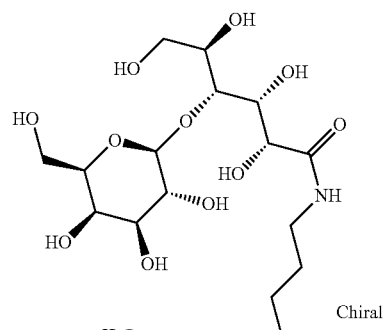
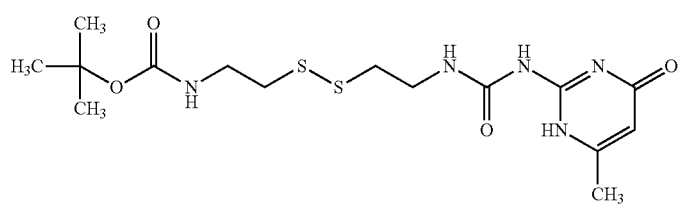
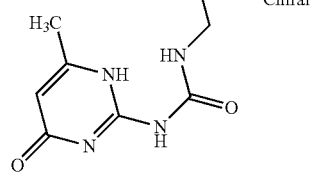

-continued
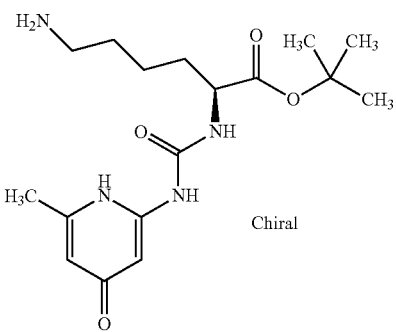
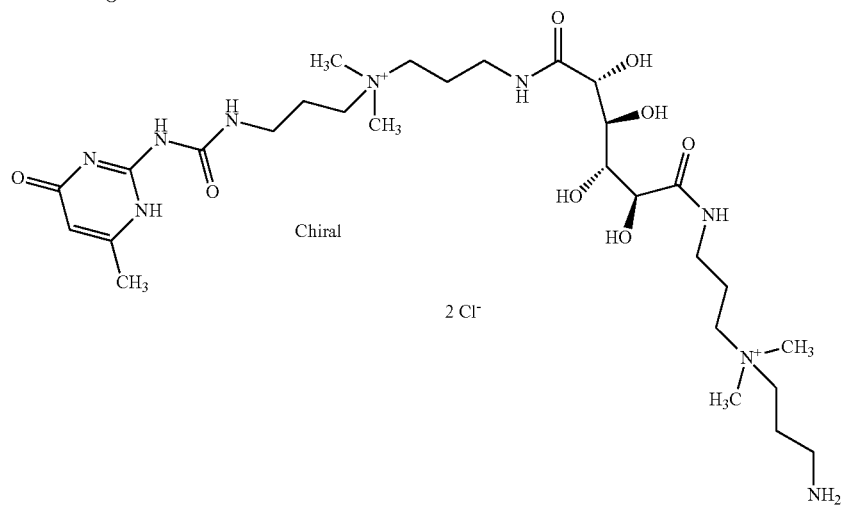
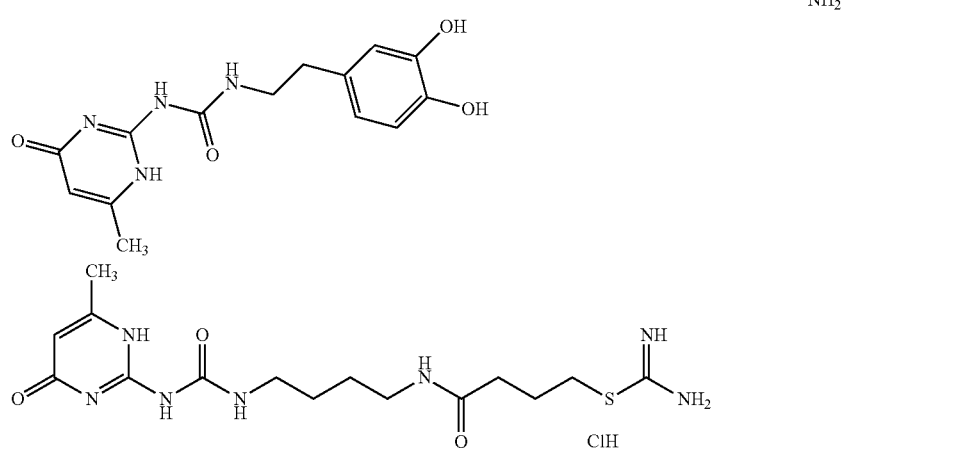
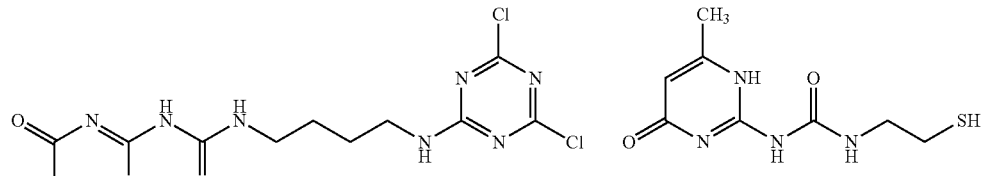
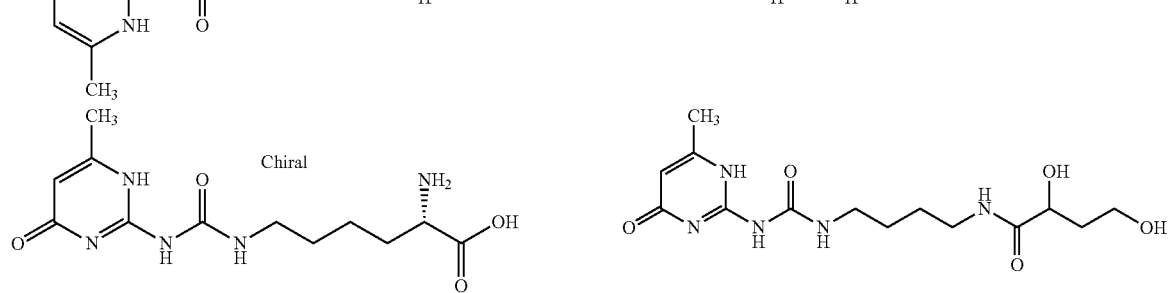

13
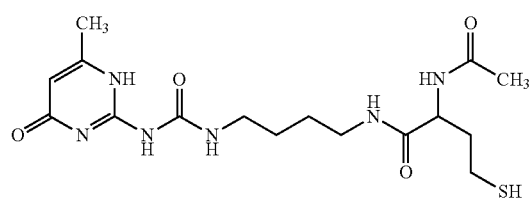
14
-continued
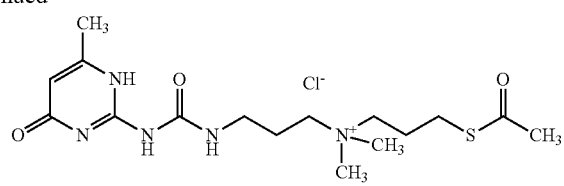
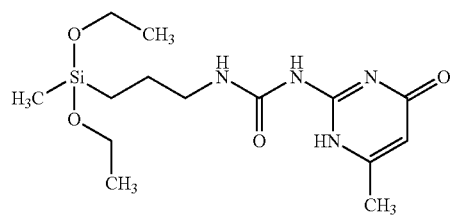
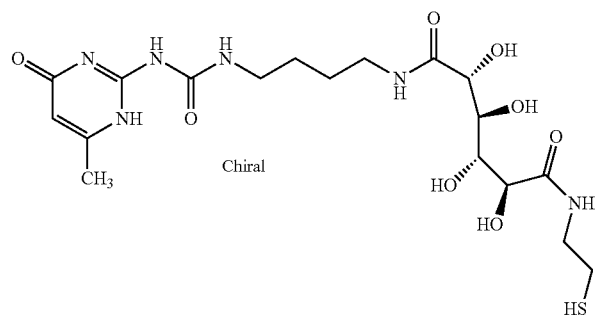
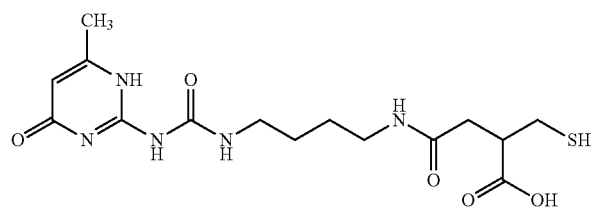
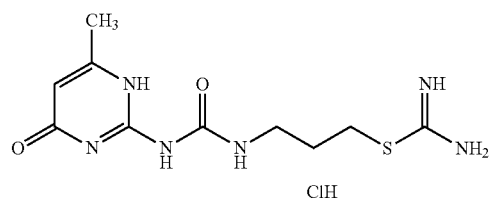
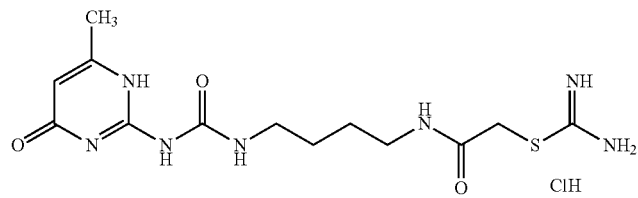
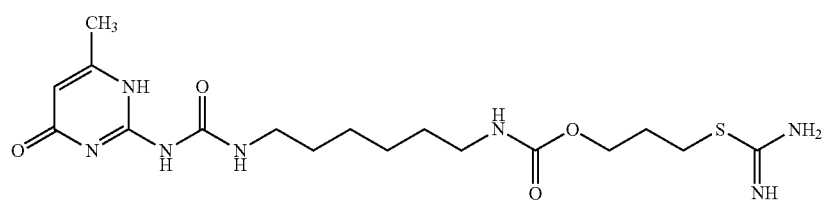
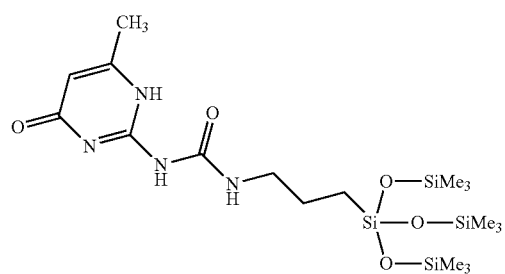

Preferably, the weight-average molecular weight ($M_w$) of the compound of formula (I) according to the invention is less than or equal to 1200 g/mol. This low molecular weight favours in particular the penetration of the compounds into the hair.

The present invention also relates to certain novel compounds, of formula (Ia), and also the tautomeric forms thereof and the salts thereof:

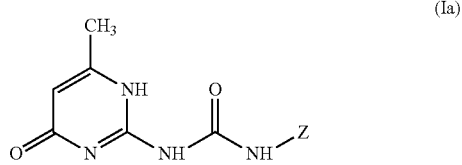

in which Z represents a monovalent radical chosen from:
(i) a non-cyclic, saturated or unsaturated, linear or branched, C1 to C32 hydrocarbon-based radical,
  optionally substituted with 1 to 20 hydroxyl radicals —OH, and/or
  optionally interrupted by 1 to 10 identical or different groups chosen from, alone or combined with one another, —S—, S(O), $SO_2$, —NH— (or =NH), —N= (trivalent), —O—, —C(O)—, —CH(OH)—, —C(=NH)—, —$N^+(CH_3)_2$—, C6-C10, especially C6-C8, aryl (cyclic aromatic) radical. Preferably, the interrupting group is chosen from the groups —NH—, —C(O)—, —CH(OH)—, —$N^+(CH_3)_2$— or is nonexistent; preferably the non-cyclic hydrocarbon-based radical is a linear C3 to C10 radical;
  terminated with a group chosen from —$NR_1R_2$, —$N^+R_1R_2R_3An^-$, —$NHC(O)OR_4$, —$CH(NH_2)CO_2R_4$, —$NHC(O)CH(OH)(CH_2)_2OH$, in which:
  $R_1$, $R_2$, $R_3$, independently represent a linear or branched C1-C6 alkyl radical, especially a methyl or ethyl radical, or a hydroxyalkyl radical, especially a hydroxyethyl radical; or an aminoalkyl radical, especially a —$(CH_2)_4$—$NH_2$ radical;
  $R_4$ represents a hydrogen atom H or a linear or branched C1-C6 alkyl radical, especially a methyl, ethyl or tert-butyl radical, or a hydroxyalkyl radical, especially a hydroxyethyl radical;
  $An^-$ denotes a cosmetically acceptable anion or a mixture of cosmetically acceptable anions;
(ii) a radical of formula (A1): —$(CH_2)_p$—$(X)_n$—$(CH_2)_q$—$NR_6$—C(=NH)—$NR_7R_8$
  in which X denotes a group chosen from —S—, S(O), $SO_2$, —NH— (or =NH), —N= (trivalent), —O—, —C(O)—, —C(=NH)—, —C(O)O—, —OC(O)—, —NC(O)—, —NC(O)N—, $NSO_2N$—, —$NR_6$—C(=NH)—$NR_7$—, —$N^+(CH_3)_2$— $An^-$, a C6-C10, especially C6-C8, aryl (cyclic aromatic) radical. Preferably, the interrupting group is equal to —NH—C(O)—NH—;
  $An^-$ denotes a cosmetically acceptable anion or a mixture of cosmetically acceptable anions.
  n, p and q are integers and
  n=0 to 8;
  p=1 to 10;
  q=1 to 10;
  p+q≠5.
  Preferably, n=0 or 1, p+q is between 4 and 10, p+q≠5.
  More preferably, n=0 and p+q=4.
  $R_6$, $R_7$, $R_8$ independently denote a hydrogen atom H, a linear or branched C1-C6 alkyl radical, especially a methyl or ethyl radical, or a hydroxyalkyl radical, especially a hydroxyethyl radical.

Preferably, $R_6$, $R_7$, $R_8$ independently denote a hydrogen atom H or a methyl or ethyl radical.
More preferably, $R_6$, $R_7$, $R_8$ are identical and represent a hydrogen atom H.
(iii) a radical of formula (A2): —$(CH_2)_r$—$(T)_s$—$(CH_2)_t$—$(CHR_9)_u$—$(CH_2)_v$—$SiR_{10}R_{11}R_{12}$
  in which T denotes a group chosen from the groups: —S—, S(O), $SO_2$, —NH— (or =NH), —N= (trivalent), —O—, —C(O)—, —C(=NH)—, —$N^+(CH_3)_2$— $An^-$, a C6-C10, especially C6-C8, aryl (cyclic aromatic) radical, a carbon-carbon double bond, especially —CH=CH—, a carbon-carbon triple bond, and combinations thereof.
  Preferably, T represents a group —NH—C(O)—NH— or —NH—C(O)—O—.
  When s, respectively u, is not zero, the adjacent T groups, respectively adjacent —$CHR_9$— groups, are identical or different.
  $R_9$ denotes a radical chosen from the radicals: —OH, —SH, —$SO_3H$, —COOH, —COOR, —NHC(O)R, NHC(O)OR, —NRR' and —N'RR'R" $An^-$, in which R, R' and R", which may be identical or different, represent a hydrogen atom H or a linear or branched C1-C6 alkyl radical, especially a methyl radical;
  $R_{10}$, $R_{11}$, $R_{12}$ are chosen independently from $OR_{13}$ radicals or linear or branched C1-C6 alkyl radicals;
  $R_{13}$ denotes a linear or branched C1-C6 alkyl radical, or a radical —$(CH_2—CH_2—O)_wR_{14}$ or a radical —$SiR_{15}R_{16}R_{17}$.
  $R_{14}$ denotes a hydrogen atom H, or a methyl radical.
  $R_{15}$, $R_{16}$ and $R_{17}$ independently denote a linear or branched C1-C4 alkyl radical.
  Preferably $R_{13}$ represents a methyl or ethyl radical or an $SiMe_3$ radical.
  $An^-$ denotes a cosmetically acceptable anion or a mixture of cosmetically acceptable anions.
  r, s, t, u, v, w are integers and
  r=1 to 10;
  s, t, u, v=0 to 10;
  w=1 to 5;
  it being understood that when s=u=0 and $R_{10}$=$R_{11}$=$R_{12}$=$OR_{13}$, then r+t+v≠3.
  Preferably, s=0 or 1, u=0, r+t+v is between 1 and 10, more preferably between 3 and 9.
(iv) a radical of formula (A3): —$(CH_2)_x$—$(U)_y$—$(CH_2)_z$—$CH_3$
  in which U denotes a group chosen from the radicals: —S—, S(O), $SO_2$, —NH— (or =NH), —N= (trivalent), —O—, —C(O)—, —C(=NH)—, —$N^+(CH_3)_2$— $An^-$, a C6-C10, especially C6-C8, aryl (cyclic aromatic) radical, a carbon-carbon double bond, especially —CH=CH—, a carbon-carbon triple bond, and also combinations thereof;
  $An^-$ denotes a cosmetically acceptable anion or a mixture of cosmetically acceptable anions.
  x, y and z are integers, between 0 and 10 inclusive;
  it being understood that when y=0, x+z is greater than or equal to 10 and less than or equal to 30 and other than 18, in particular x+z is equal to 15;
  and that when y≠0, x is greater than or equal to 2 and less than or equal to 25 and z is greater than or equal to 3 and less than or equal to 25, in particular x+z is equal to 15 with U equal to C=C and y=1;
(v) a radical of formula (A4): -Alk1-$(V)_{a1}$-$(Alk2)_{a2}$—$CH_2$—W
  in which Alk1 and Alk2 independently denote a saturated or unsaturated, linear or branched, C1 to C32 alkyl radical. Preferably the alkyl radical is a saturated C1 to C10 alkyl radical.

V denotes a group chosen from the radicals: —S—, S(O), SO$_2$, —NH— (or =NH), —N= (trivalent), —O—, —C(O)—, —C(=NH)—, —N$^+$(CH$_3$)$_2$— An$^-$, a C6-C10, especially C6-C8, aryl (cyclic aromatic) radical, a carbon-carbon double bond, especially —CH=CH—, a carbon-carbon triple bond, or combinations thereof. Preferably, V represents a group chosen from: —NH—C(O)—, NH—C(O)—NH—, —NH—CO—O—, O—C(O)—, —N$^+$(CH$_3$)$_2$-An$^-$.

An$^-$ denotes a cosmetically acceptable anion or a mixture of cosmetically acceptable anions.

W denotes a radical chosen from the radicals: —SR$_{15}$, —S(O)R$_{15}$, —SO$_2$R$_{15}$, —SO$_3$H, —OSO$_3$H. Preferably, W represents an —SR$_{15}$ or —SO$_3$H radical.

R$_{15}$ denotes an aromatic C5-C10, especially C5-C6 (hetero)cycle, 3 carbon atoms of which can be replaced by nitrogen atoms; a carbonyl radical —C(O)R$_{16}$; a radical —C(=NR$_{17}$)—NR$_{18}$R$_{19}$;

R$_{16}$ denotes a linear or branched C1 to C6 alkyl radical;

R$_{17}$, R$_{18}$, R$_{19}$ independently denote a hydrogen atom H or a linear or branched C1-C6 alkyl radical;

R$_{17}$ and R$_{18}$ may be connected to one another in order to form, with the nitrogen atoms to which they are attached, a saturated or unsaturated ring or bicyclic ring containing from 5 to 8 atoms.

a1 and a2 are integers.

a1=0 to 8, preferably 0 to 2.

a2=0 or 1.

(vi) a radical of formula (A5): —Y—(K)$_j$-G in which Y denotes a saturated or unsaturated, linear or branched C1 to C32 alkyl radical, optionally interrupted by 1 to 8 identical or different groups chosen from —S—, S(O), SO$_2$, —NH— (or =NH), —N= (trivalent), —O—, —C(O)—, —C(=NH)—, —N$^+$(CH$_3$)$_2$— An$^-$, a C6-C10, especially C6-C8 aryl (cyclic aromatic) radical, or combination thereof.

Preferably, Y denotes a saturated C2 to C8, more preferably C2, C4, C6 alkyl radical;

K denotes a group chosen from —CO—, —NHC(O)—, —CH(NRR')—, —CHR—, —C(=CHR)—.

Preferably, K denotes a group —CO— or —NHC(O)—, more preferably —NHC(O)—;

G denotes a group chosen from G1, G2 or G3, where:

G1 denotes a monosaccharide or a polysaccharide containing up to 20 sugar units, in pyranose and/or furanose form and of L and/or D series, said monosaccharide or polysaccharide optionally having one or more amine functions, the hydroxyl and amine functions being optionally protected; and the optical and/or geometric isomers thereof. Preferably, G1 represents a monosaccharide or a polysaccharide containing up to 6 sugar units, in pyranose and/or furanose form and of L and/or D series. Advantageously, the preferred monosaccharides are chosen from D-glucosamine, D-galactosamine, D-glucose, D-galactose, D-mannose, D-xylose, D-lyxose, L-fucose, L-arabinose, L-rhamnose, D-glucuronic acid, D-galacturonic acid, D-iduronic acid, with a preference for D-glucosamine. These monosaccharides may or may not be protected at the hydroxyl functions not involved in the bond with the H radical. More advantageously, the preferred polysaccharides containing up to 6 sugar units are chosen from D-maltose, D-lactose, D-cellobiose, D-maltotriose, a disaccharide combining a uronic acid chosen from D-iduronic acid or D-glucuronic acid with a hexosamine chosen from D-galactosamine, D-glucosamine, N-acetyl-D-galactosamine, N-acetyl-D-glucosamine.

G2 denotes an alpha amino acid radical with a protected or unprotected side chain, chosen from the side chains of the 22 natural amino acids, this radical being C or N branched, racemic or non-racemic, of L or D stereochemistry, protected or unprotected at the C or N residue and at the side chain for the alpha amino acids in question. Preferably, the side chain is the side chain of a cysteine, of a lysine, of an aspartic acid, of a glutamic acid or of an arginine, more preferably a lysine.

G3 denotes a phenyl radical substituted at any one of the positions with a hydroxyl radical and optionally substituted with a group R$_{20}$. Preferably, G3 denotes an ortho-diphenol.

R$_{20}$ denotes a saturated or unsaturated, linear or branched C1 to C6 alkyl radical, a C1 to C6 hydroxyalkyl radical, a C5-C10 aryl (cyclic aromatic) radical, or a radical —OH, —SH, —SO$_3$H, —COOH, —COOR, —NHC(O)R, NHC(O)OR, —NRR' and —N'RR'R" An$^-$.

R, R' and R" independently denote a hydrogen atom H or a C1-C6 alkyl radical, especially a methyl radical.

An$^-$ denotes a cosmetically acceptable anion or a mixture of cosmetically acceptable anions.

j is an integer equal to 0 or 1.

Preferably, j=1 when G denotes a radical G1 and j=0 when G denotes a radical G2 or G3.

When G denotes a radical G1, and when G1 is connected to H by an anomeric bond, this anomeric bond may be α or β.

The protected hydroxyl or amine functions of monosaccharides or of polysaccharides are, for example, those obtained by the protection reactions described in "Protective Groups in Organic Synthesis", T. W. Greene, P. G. M. Wuts, second edition, Wiley Interscience, 1991.

(vii) a radical of formula (A6): —(CH$_2$)$_g$-(J)$_h$-(CH$_2$)$_i$—(CHR$_{23}$)$_k$—CH$_2$R$_{24}$ in which J denotes a group chosen from the groups: —S—, S(O), SO$_2$, —NH— (or =NH), —N= (trivalent), —O—, —C(O)—, —C(=NH)—, —N$^+$(CH$_3$)$_2$— An$^-$, a C6-C10, especially C6-C8, aryl (cyclic aromatic) radical, a carbon-carbon double bond, especially —CH=CH—, a carbon-carbon triple bond, or combinations thereof.

Preferably, J denotes a —NH—C(O)— group;

R$_{23}$ denotes a radical —OR$_{25}$, —SH, —SO$_3$H, —COOH, —COOR, —NHC(O)R, NHC(O)OR, —NRR' and —N'RR'R" An$^-$, with R, R' and R"=H or C1-C6 alkyl, especially methyl. Preferably, R$_{23}$ denotes a radical —OR$_{25}$;

R$_{24}$ denotes a hydrogen atom H, or a hydroxyl radical —OH;

R$_{25}$ denotes a hydrogen atom H, or a monosaccharide or a polysaccharide containing up to 20 sugar units, in pyranose and/or furanose form and of L and/or D series, said monosaccharide or polysaccharide optionally having one or more amine functions, the hydroxyl and amine functions being optionally protected; and the optical and/or geometric isomers thereof. Preferably, R$_{25}$ represents a hydrogen atom or a monosaccharide or a polysaccharide containing up to 6 sugar units, in pyranose and/or furanose form and of L and/or D series. Advantageously, the preferred monosaccharides are chosen from D-glucosamine, D-galactosamine, D-glucose, D-galactose, D-mannose, D-xylose, D-lyxose, L-fucose, L-arabinose, L-rhamnose, D-glucuronic acid, D-galacturonic acid, D-iduronic acid, with a preference for glucose. These monosaccharides may or may not be protected at the hydroxyl functions not involved in the bond with the radical —$CH_2$—$R_{24}$. More advantageously, the preferred polysaccharides containing up to 6 sugar units are chosen from D-maltose, D-lactose, D-cellobiose, D-maltotriose, a disaccharide combining a uronic acid chosen from D-iduronic acid or D-glucuronic acid with a hexosamine chosen from D-galactosamine, D-glucosamine, N-acetyl-D-galactosamine, N-acetyl-D-glucosamine.

An⁻ denotes a cosmetically acceptable anion or a mixture of cosmetically acceptable anions.

g, h, i, k denote an integer;

g, h, k=1 to 10;

i=0 to 10.

Preferably, g, h, k=1 to 6; i=0 to 3.

More preferably, g=4 to 6, h=1, k=4 to 6, i=0.

In the case where $R_{25}$ is connected to $R_{23}$ by an anomeric bond, this anomeric bond may be α or β.

(viii) a radical of formula (A7): —$(CH_2)_b$-(A)-(B)-(A)$_c$-$(CH_2)_d$-D in which A denotes a group chosen from —NHC(O)—, —C(O)NH—, —NHC(O)NH—, —C(O)O—, —OC(O)—;

B denotes a branched or unbranched hydrocarbon-based chain, optionally substituted with a radical chosen from —OH, —COOH, —NHC(O)$R_{21}$;

$R_{21}$ denotes a linear or branched C1-C6 alkyl radical; D denotes a radical —SH or a linear or branched C1 to C4 alkyl radical.

b, c and d are integers;

b=2 to 10, preferably 3 to 6;

c=0 or 1;

d=0 to 10, preferably 0 to 3;

(ix) a radical of formula (A8): -Alk3-S—S-Alk4 in which Alk4 denotes a linear or branched C2 to C20 hydrocarbon-based radical, optionally comprising one or more double bonds, and optionally comprising one or more heteroatoms chosen from O or N, and optionally substituted with one or more identical or different radicals chosen from —OH, —$SO_3H$, —COOH, —COOR, —NHC(O)R, NHC(O)OR, —NRR' and —N'RR'R" An⁻.

Alk3 denotes a linear or branched C2 to C20 hydrocarbon-based radical, optionally comprising one or more double bonds, and optionally comprising one or more heteroatoms chosen from O or N, and optionally substituted with one or more identical or different radicals chosen from —OH, —$SO_3H$, —COOH, —COOR, —NHC(O)R, —NRR' and —N'RR'R" An⁻.

R, R' and R" independently denote a hydrogen atom H or a linear or branched C1-C6 alkyl radical, especially a tert-butyl or methyl radical.

An⁻ denotes a cosmetically acceptable anion or a mixture of cosmetically acceptable anions.

Preferably, Alk3 represents a linear or branched C2 to C10 hydrocarbon-based chain, optionally interrupted by a group chosen from —NH—C(O)—O, —NH—C(O)—, —O—C(O)—.

More preferably still, Alk3 represents a linear C2 to C6 hydrocarbon-based chain.

(x) a radical of formula (A9): —CHL-COO$R_{22}$ in which L denotes the side chain of an alpha amino acid, chosen from the side chains of the 22 natural amino acids; the stereochemistry is L, D or a racemic mixture. Preferably, the side chain is the side chain of a lysine (—$(CH_2)_4$—$NH_2$), of a glutamic acid (—$CH_2$—$CH_2$—$CO_2H$) or of a glutamine (—$CH_2$—$CH_2$—CO—$NH_2$), protected or unprotected.

$R_{22}$ denotes a hydrogen atom H, or a linear or branched C1 to C6 alkyl radical, or a benzyl radical.

Preferably, $R_{22}$ denotes a hydrogen atom H, or a tert-butyl radical.

(xi) a radical —$(CH_2)_2$—SH (xii) a radical —$(CH_2)_4$—$NH_2$

According to a first variant, the compounds of formula (Ia) are such that Z denotes: a linear, saturated, non-cyclic C1 to C20 hydrocarbon-based radical optionally substituted with 1 to 5 hydroxyl radicals —OH, optionally interrupted by 1 to 5 identical or different functional groups chosen from —NH—CO—NH—, —NHCO—, CO—NH—N⁺$(CH_3)_2$—, terminated by a group chosen from —$NR_1R_2$, —N⁺$R_1R_2R_3$An⁻, —NHC(O)O$R_4$, —CH($NH_2$)$CO_2R_4$, —NHC(O)CH(OH)$(CH_2)_2$OH, in which:

$R_1$, $R_2$, $R_3$, independently represent a methyl or ethyl radical or an aminoalkyl, especially —$(CH_2)_4$—$NH_2$, radical.

$R_4$ represents a hydrogen atom H or a methyl, ethyl or tert-butyl radical;

An⁻ denotes a cosmetically acceptable anion or a mixture of cosmetically acceptable anions.

According to a second variant, the compounds of formula (Ia) are such that Z denotes a radical (A1) in which n represents 0 or 1, X represents —NH—C(O)—NH—.

p+q=4 to 10, it being understood that p+q≠5.

More preferably, according to this variant, n=0, p+q=4.

According to a third variant, the compounds of formula (Ia) are such that Z denotes a radical (A2) in which T represents a group —NH—C(O)—NH— or —NH—C(O)—O—, u=0, s=0 or 1, r, t and v are integers with r+t+v between 1 and 10, more preferably between 3 and 9.

$R_{10}$, $R_{11}$, $R_{12}$ are chosen independently from among the radicals OMe, OEt, OSiMe3, Me, Et, it being understood that when s=u=0 and $R_{10}$=$R_{11}$=$R_{12}$=O$R_{13}$, then r+t+v≠3.

According to a fourth variant, the compounds of formula (Ia) are such that Z denotes a radical (A3) in which U denotes a carbon-carbon double bond CH=CH, y is equal to 0 or 1 and x+z=15.

According to a fifth variant, the compounds of formula (Ia) are such that Z denotes a radical (A4) in which Alk1 and Alk2 independently denote a linear, saturated C1 to C10 alkyl radical.

V denotes a group chosen from the radicals —NH—C(O)—, NH—C(O)—O—, —N⁺$(CH_3)_2$-An⁻.

An⁻ denotes a cosmetically acceptable anion or a mixture of cosmetically acceptable anions.

W represents a radical —S—CO—$CH_3$ or —$SO_3H$ or —S—C(=NH)$NH_2$.

a1=0 or 1.

a2=0 or 1.

According to a sixth variant, the compounds of formula (Ia) are such that Z denotes a radical (A5) in which Y denotes a linear, saturated C1 to C8, more preferably C2, C4, C6 alkyl radical; K denotes a group —CO— or —NHC(O)—, more preferably —NHC(O)—; j is equal to 0 or 1.

G denotes a group chosen from G1, G3, where:

G1 denotes a monosaccharide in pyranose and/or furanose form and of L and/or D series, said monosaccharide optionally having one or more amine functions, the hydroxyl and amine functions being optionally protected; and the optical and/or geometric isomers thereof. Advantageously, the preferred monosaccharides are chosen from D-glucosamine, D-galactosamine, with a preference for D-glucosamine. These monosaccharides may or may not be protected at the hydroxyl functions not involved in the bond with the H radical.

G3 denotes an ortho-diphenol radical.

Preferably, j=1 when G denotes a radical G1 and j=0 when G denotes a radical G3.

When G denotes a radical G1, and when G1 is connected to H by an anomeric bond, this anomeric bond may be α or β.

According to a seventh variant, the compounds of formula (Ia) are such that Z denotes a radical (A6) in which J denotes a group —NH—C(O)—;

$R_{23}$ denotes a radical —$OR_{25}$, —SH, —$SO_3H$, —COOH, —COOR, —NHC(O)R, NHC(O)OR, —NRR' and —N'RR'R" An⁻, with R, R' and R"=H or C1-C6 alkyl, especially methyl. $R_{23}$ denotes a radical —$OR_{25}$.

$R_{24}$ denotes a hydrogen atom H, or a hydroxyl radical —OH, preferably a hydroxyl radical —OH.

$R_{25}$ denotes a hydrogen atom H, or a monosaccharide, in pyranose and/or furanose form and of L and/or D series, said monosaccharide optionally having one or more amine functions, the hydroxyl and amine functions being optionally protected; and the optical and/or geometric isomers thereof. Preferably, $R_{25}$ represents a hydrogen atom or a monosaccharide in pyranose and/or furanose form and of L and/or D series. Advantageously, the preferred monosaccharides are chosen from D-glucose, D-galactose, D-mannose, D-xylose, D-lyxose, L-fucose, L-arabinose, L-rhamnose. These monosaccharides may or may not be protected at the hydroxyl functions not involved in the bond with the radical —$CH_2$—$R_{24}$.

More preferably, $R_{25}$ denotes a hydrogen atom or glucose.

g=4 to 6, h=1, k=4 to 6, i=0.

In the case where $R_{25}$ is connected to $R_{23}$ by an anomeric bond, this anomeric bond may be α or β.

According to an eighth variant, the compounds of formula (Ia) are such that Z denotes a radical (A7) in which A denotes a group —NHC(O)—, B denotes a branched or unbranched hydrocarbon-based chain, optionally substituted by a radical chosen from —OH, —COOH, —NHC(O)$R_{21}$;

$R_{21}$ denotes a linear or branched C1 to C4 alkyl radical, preferably a methyl radical;

D denotes an —SH radical or a linear or branched C1 to C4 alkyl radical, preferably an —SH radical or a methyl radical.

b=3 to 6;

c=0 or 1, preferably c=0;

d=0 to 3.

According to a ninth variant, the compounds of formula (Ia) are such that Z denotes a radical (A8) in which Alk4 denotes a linear C2 to C10 hydrocarbon-based radical, optionally substituted with one or more identical or different radicals chosen from —COOR, —NHC(O)R, NHC(O)OR, preferably NH—C(O)—OR.

Alk3 denotes a linear C2 to C6 hydrocarbon-based radical.

R denotes a hydrogen atom H or a linear or branched C1-C4 alkyl radical, especially a tert-butyl or methyl radical.

According to a tenth variant, the compounds of formula (Ia) are such that Z denotes a radical (A9) in which L denotes the side chain of a lysine (—$(CH_2)_4$—$NH_2$), of a glutamic acid (—$CH_2$—$CH_2$—$CO_2H$) or of a glutamine (—$CH_2$—$CH_2$—CO—$NH_2$), protected or unprotected, the amino acid precursor being D or L or racemic.

$R_{22}$ denotes a hydrogen atom H, or a linear or branched C1 to C6 alkyl radical, or a benzyl radical. Preferably, $R_{22}$ denotes a hydrogen atom H, or a tert-butyl radical.

Preferably, the compounds of formula (I) are the following:

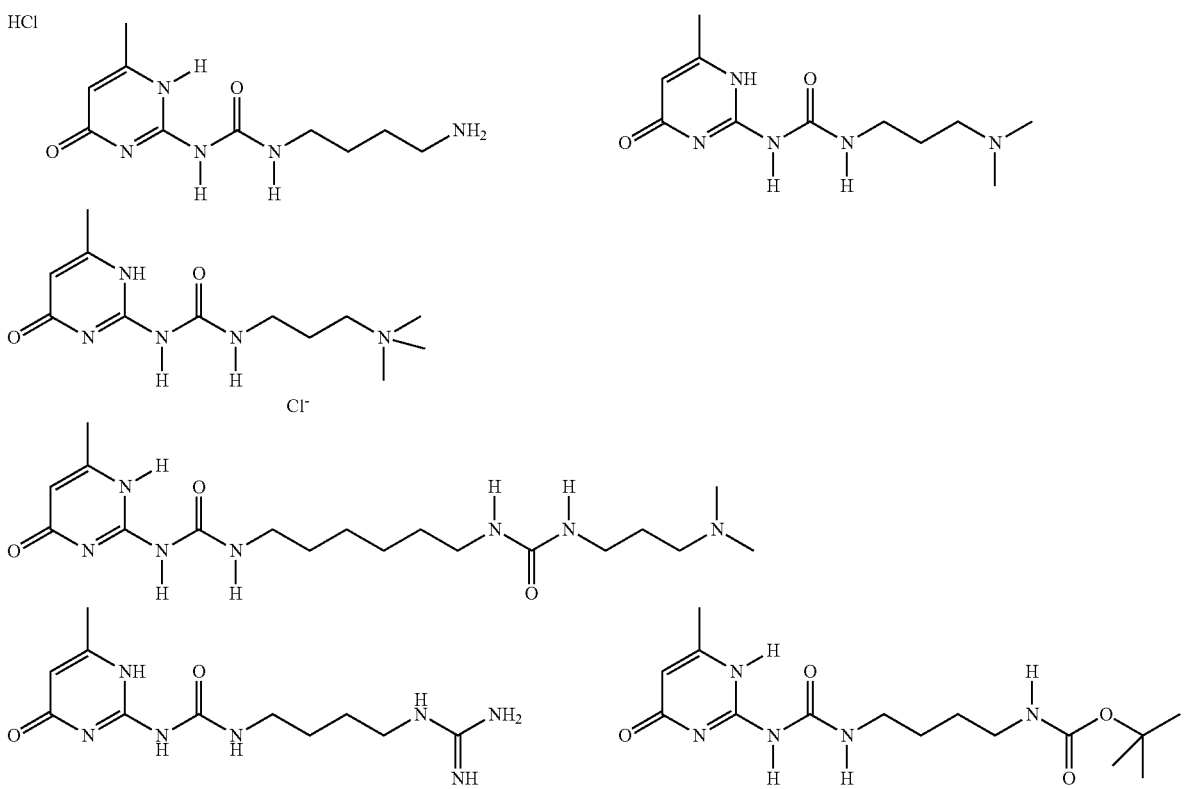

-continued
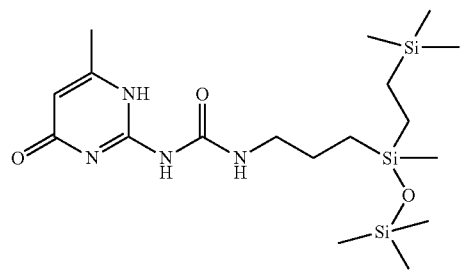
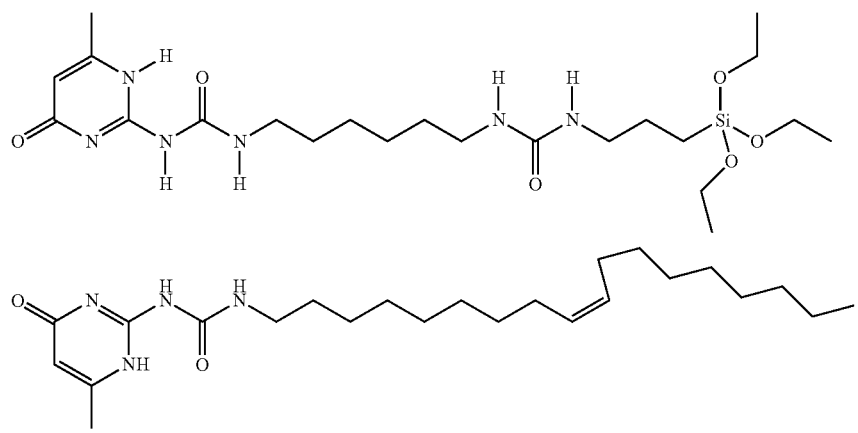
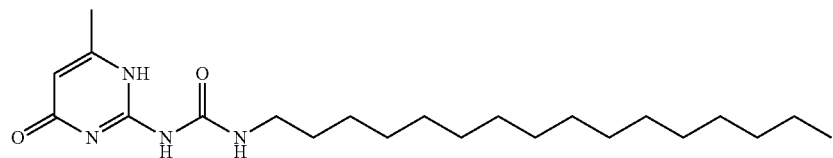
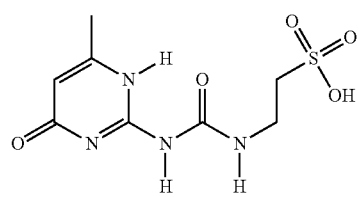
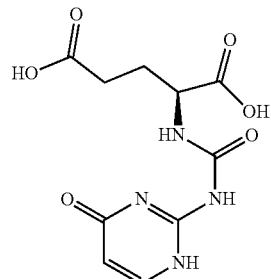
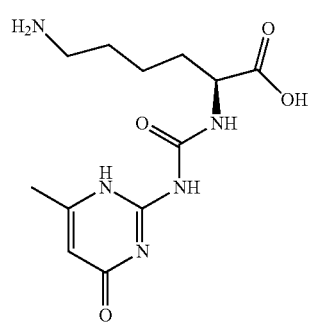
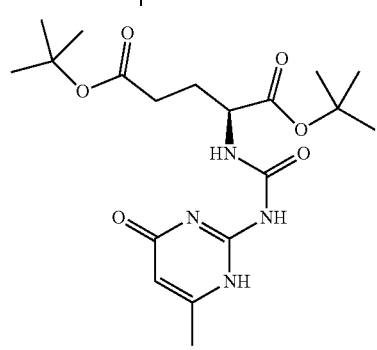

25
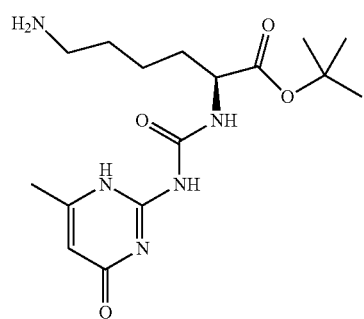
26
-continued
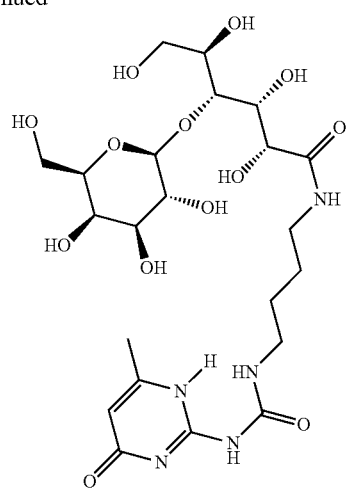
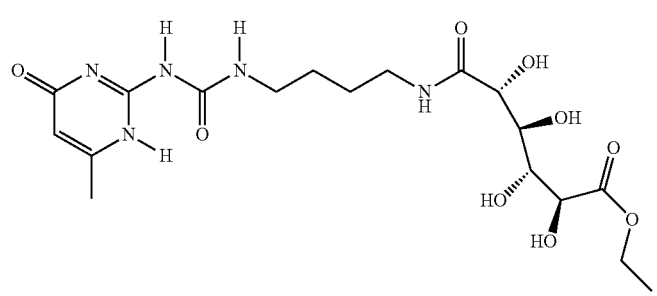
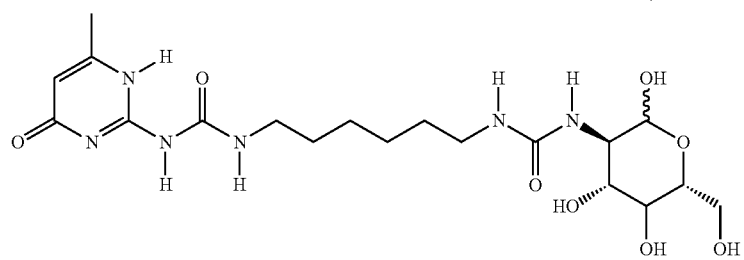
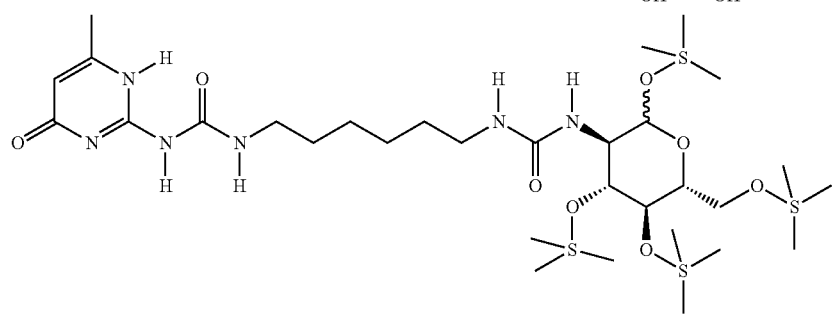
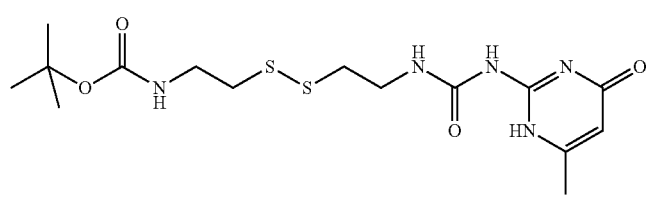
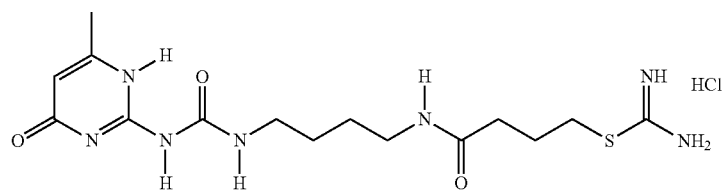

-continued
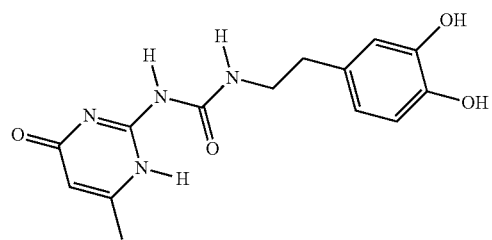
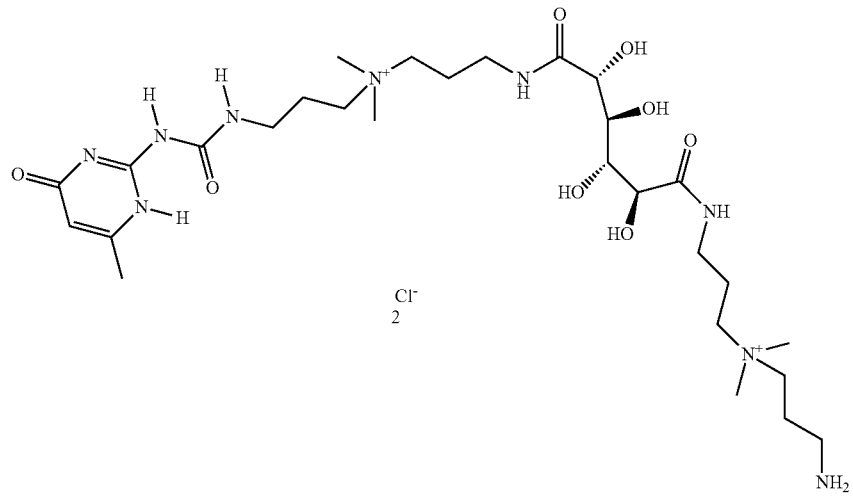
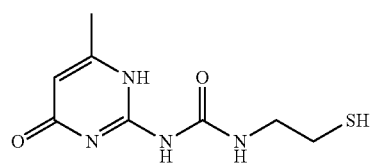
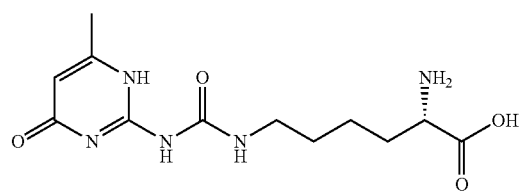
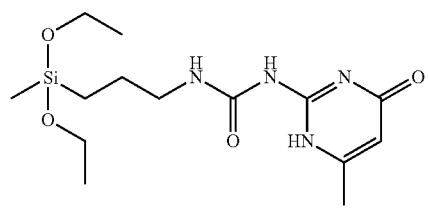
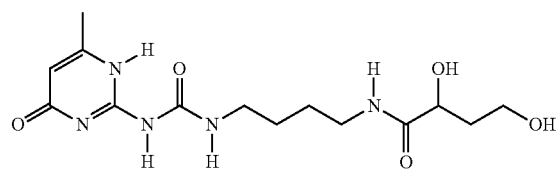
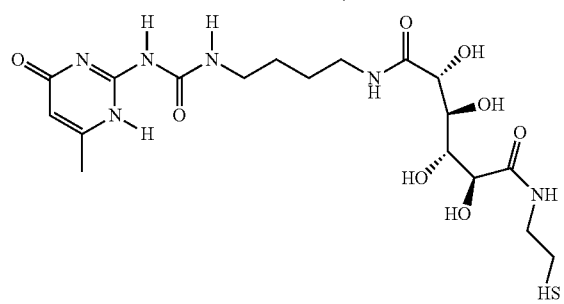
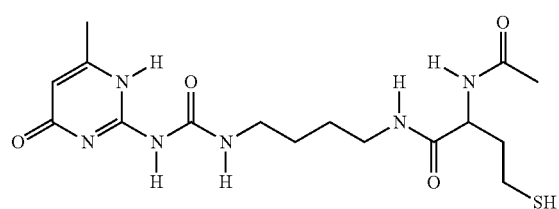
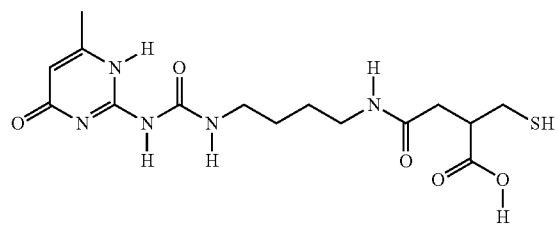
HCl
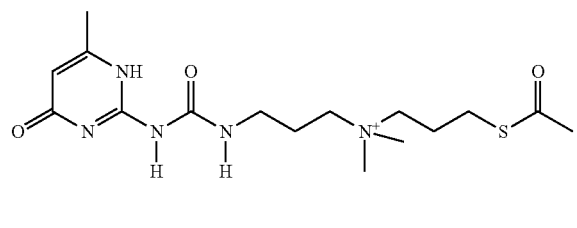

-continued

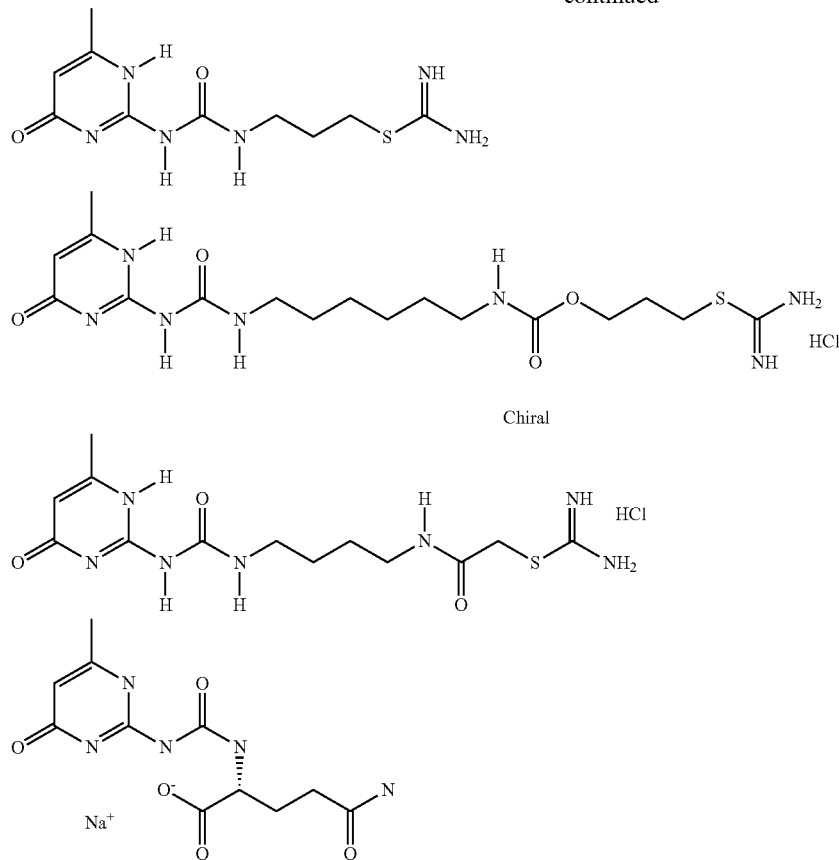

Definition of an N-branched amino acid: —NH—CHL-COP, with L representing the side chain and P being equal to —OH or an acid-protecting group such as an alcohol or an amine.

Definition of a C-branched amino acid: —C(O)—CHL-NHP, with L representing the side chain and P equal to –H or an amine-protecting group such as the group —NHP which represents an amide, a urea, a carbamate, a guanidine.

The compounds of formula (I) may be prepared according to any known method.

If the reference A is given to the group below:

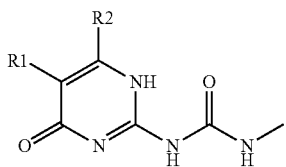

the compounds according to the invention may be represented schematically as: A-Z.

They may be obtained during the reaction:
- between a reactive function bonded to the group A with a reactive function borne by the group Z; or else
- between a reactive function bonded to a precursor of the group A with a reactive function borne by the group Z in order to simultaneously form the group A and the entity A-Z;

the two reactive functions of course being capable of reacting with one another, and possibly being bonded directly or via a divalent segment to the group A, to the group Z and/or to the precursor of said group A.

The reactive functions may preferably be chosen from the following functions:
- isocyanate —N=C=O;
- isothiocyanate —N=C=S;
- carboxylic acid or ester —COOR$_a$ with R$_a$=H or a linear or branched C1-C12, preferably C1-C4 alkyl, better still methyl or ethyl, radical;
- activated ester COOR$_b$ with OR$_b$ chosen from phenoxy, 4-nitrophenoxy, 2,4,5-trichlorophenoxy and the following radicals:

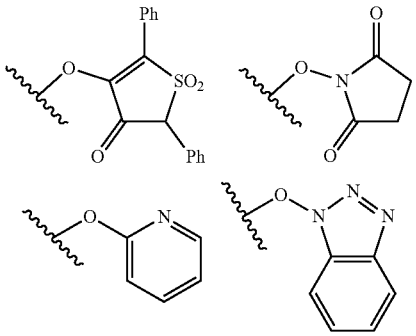

acyl halide,
acyl imidazole or acyl benzotriazole of formula:

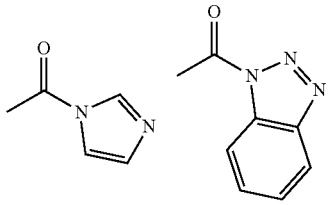

acid anhydride;
activated carbamic acid —NHCOX with X=Cl, imidazole or $OR_b$ with $OR_b$ as defined above;
hydroxyl (OH) or activated hydroxyl, for example in O-tosylate form;
primary or secondary amine —$N(R_a)_2$, where the $R_a$ groups, which are identical or different, are as defined above;
a function chosen from:

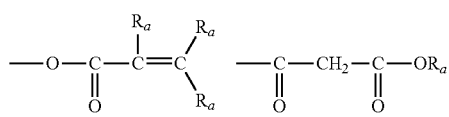

with $R_a$, which may be identical or different, being as defined above.

Preferably, the reactive functions that are a precursor of the bond between Z and A are chosen from isocyanate, amine or hydroxyl functions or functions of formula:

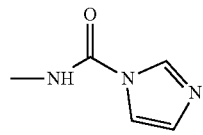

One particular method for obtaining the compounds according to the invention is described in the article by Katritzky et al., Comprehensive Organic Functional Group Transformations, Pergamon, Oxford, 1995, vol. 6, pp. 500-506 or else in Arkiv der Pharmazie, 314(1), 34-41, 1981.

It is in particular possible to react:
an isocytosine with an activated carbamic acid:

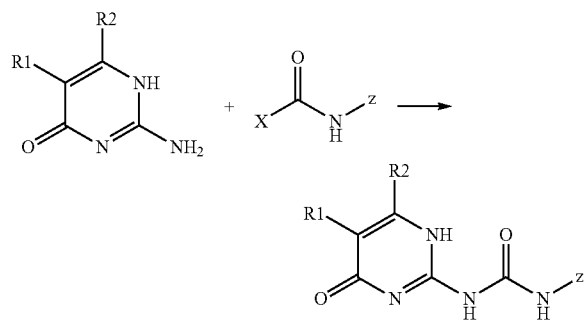

an isocytosine with an amine-derived isocyanate:

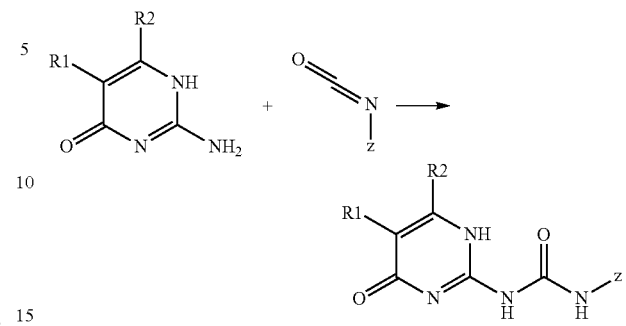

an isocytosine containing an activated carbamic function with an amine:

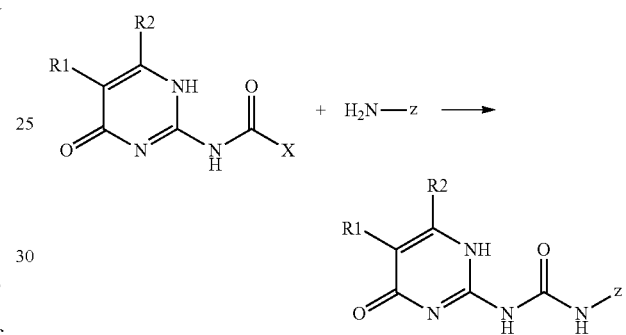

a β-keto ester with a guanylalkylurea derivative:

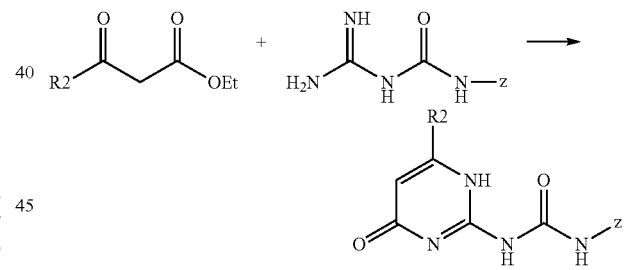

Another method for preparing the compounds according to the invention consists in synthesizing a compound of the following type:

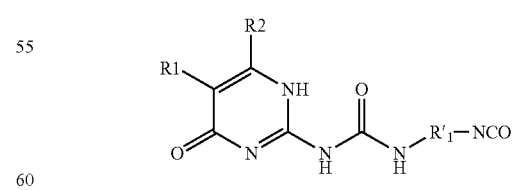

and then reacting it with an alcohol or an amine.

In this formula, the divalent group R'1 represents, for example, a group chosen from: 1,2-ethylene, 1,6-hexylene, 1,4-butylene, 1,6-(2,4,4-trimethylhexylene); 1,4-(4-methylpentylene), 1,5-(5-methylhexylene), 1,6-(6-methylheptylene); 1,5-(2,2,5-trimethylhexylene), 1,7-(3,7-dimethyloctylene); isophorone; 4,4'-methylenebiscyclohexylene, tolylene, 2-methyl-1,3-phenylene; 4-methyl-1,3-phenylene; 4,4-biphenylenemethylene; and preferably isophorone; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebiscyclohexylene; 2-methyl-1,3-phenylene. Better still, R'$_1$=isophorone or 1,6-hexylene.

Preferably, R$_1$=H and R$_2$=methyl.

Particularly preferably, the compounds of formula (I) are soluble or dispersible in water or soluble in water basified using a 28% aqueous ammonia solution (the pH of the solution is then between 8 and 10), or soluble in water acidified using citric acid.

The term "soluble" is understood to mean that the compound forms a clear solution, at a concentration of 0.1% by weight in the medium, at 25° C. and 1 atm.

The term "dispersible" is understood to mean that the compound forms, in the medium, at a concentration of 0.1% by weight at 25° C. and 1 atm., a stable suspension or dispersion of fine particles, which are generally spherical. The term "stable" is understood to mean that the suspension does not precipitate and does not therefore display any visible deposit. The mean size of the particles constituting the suspension or the dispersion is preferably less than 1 μm, and more generally ranges between 5 and 400 nm, preferably 10 to 250 nm. These particle sizes are measured by any conventional light scattering method.

The compounds according to the invention find a very particular application in the field of cosmetics, especially in the field of haircare.

The amount of compound present in the cosmetic compositions according to the invention depends, of course, on the type of composition and on the desired properties, and can vary within a very wide range, generally between 0.001% and 30% by weight, preferably between 0.005% and 15% by weight, in particular between 0.01% and 10% by weight, or even between 0.1% and 5% by weight, relative to the total weight of the composition.

The cosmetic compositions can of course comprise a mixture of compounds of formula (I).

In one particular embodiment of the invention, the cosmetic compositions may comprise, besides the compounds of formula (I), compounds of formula (II) as defined below.

Specifically, it has been noted that when a mixture of compounds (I) and compounds (11) is used, a modification of the mechanical properties of the hair is observed, which may be an increase or decrease in their rigidity, depending on the nature of the compounds used.

Preferably, the compositions may comprise the compounds (11), alone or as a mixture, in an amount between 0.001% and 30% by weight, preferably between 0.005% and 15% by weight, especially between 0.01% and 10% by weight, or even between 0.1% and 5% by weight, relative to the total weight of the composition.

The additional compounds therefore correspond to the formula (II):

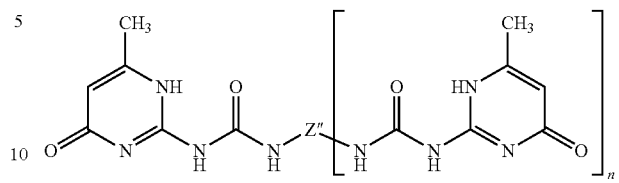

in which:

n=1 or 2, and

Z represents a divalent or trivalent (depending on the value of n), linear or branched C1-C32 alkyl or C2-C32 alkenyl radical; preferably a C2-C18, especially a C3-C12 radical;

optionally substituted with 1 to 10, especially 2 to 8, or even 3 to 6 radicals chosen from —OH, —SO$_3$H, —COOH, —COOR and —N'RR'R", with R, R' and R"=C1-C12 alkyl, especially methyl; and/or optionally interrupted by 1 to 10, especially 2 to 8, or even 3 to 6 groups chosen from (i) the divalent groups: —S—, —NH— (or =NH), —O—, —C(O)—, or of formula:

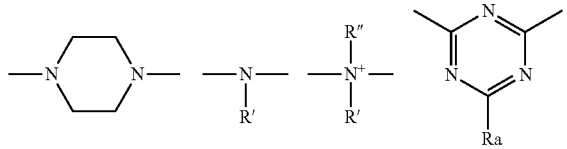

with Ra=H or halogen, especially Cl, or C1-C6 alkyl, or single bond, and

R' and R", which may be identical or different, representing a hydrogen atom or a C1-C6 alkyl radical, especially methyl; and (ii) the trivalent groups of formula:

—N$^+$— —N—
 |        |
 R'

R' representing a hydrogen atom or a C1-C6 alkyl radical, especially methyl; said trivalent groups generally being present at the junction of said radicals.

Among the compounds of formula (II) capable of being used, mention may be made of the following compounds:

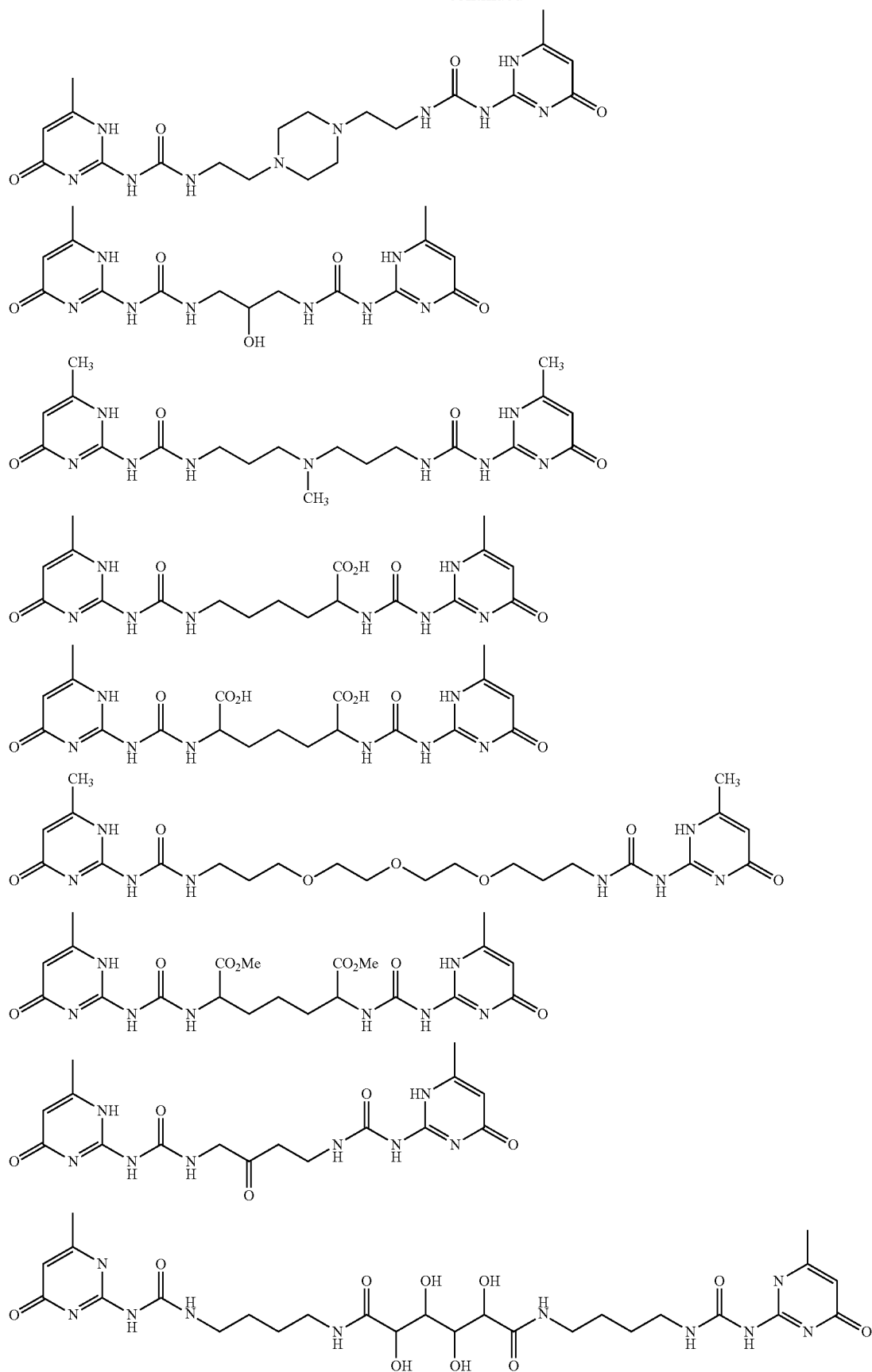

-continued
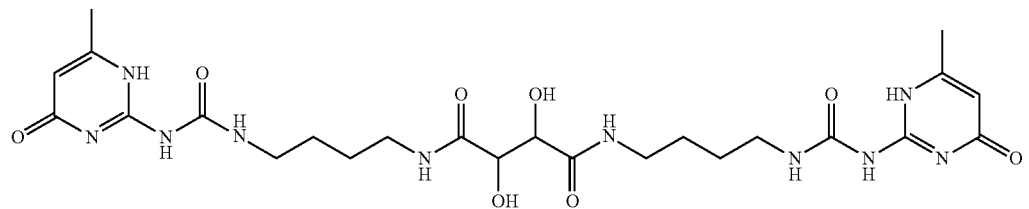
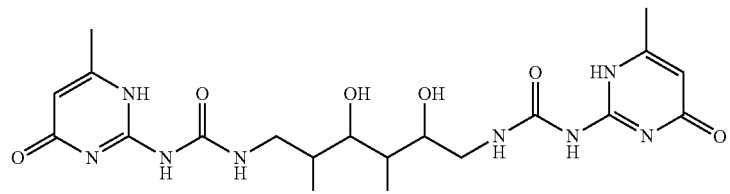
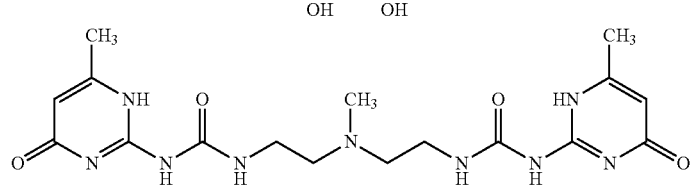
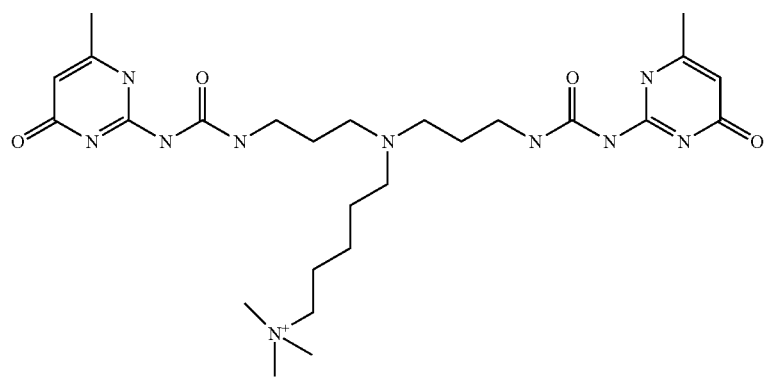
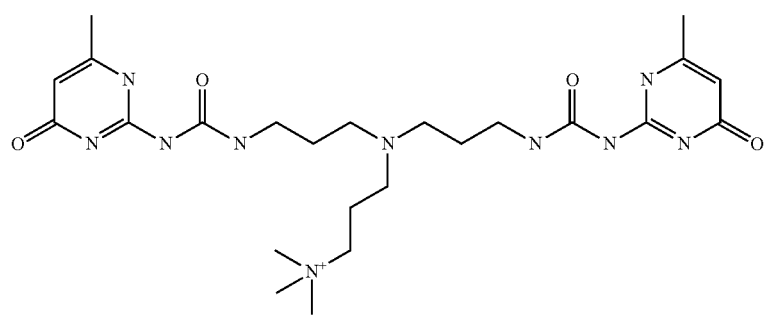
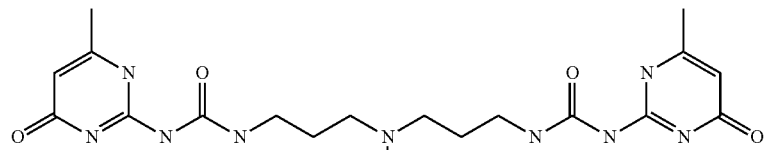
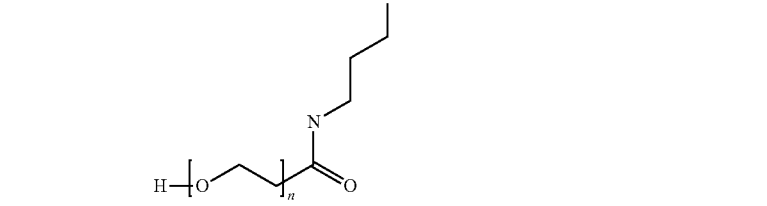
with n = 1 to 4

-continued
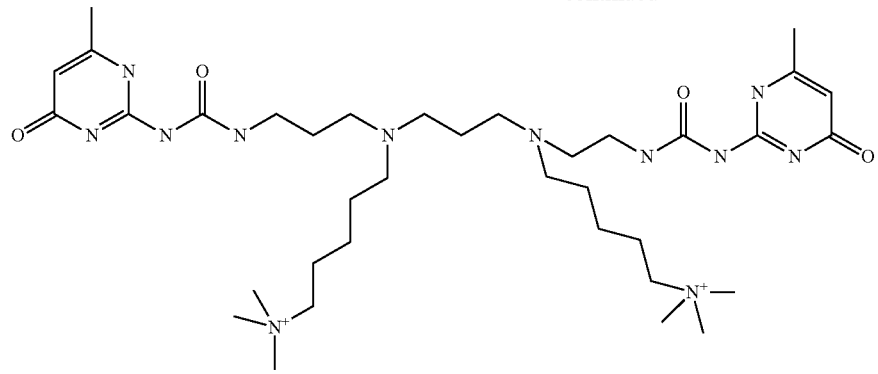
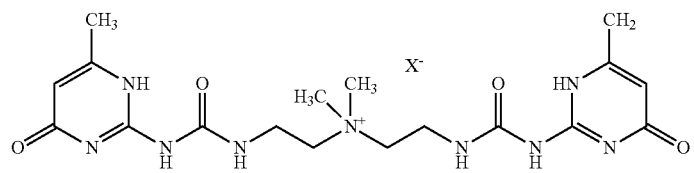
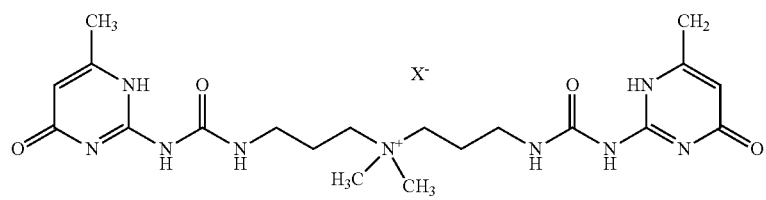
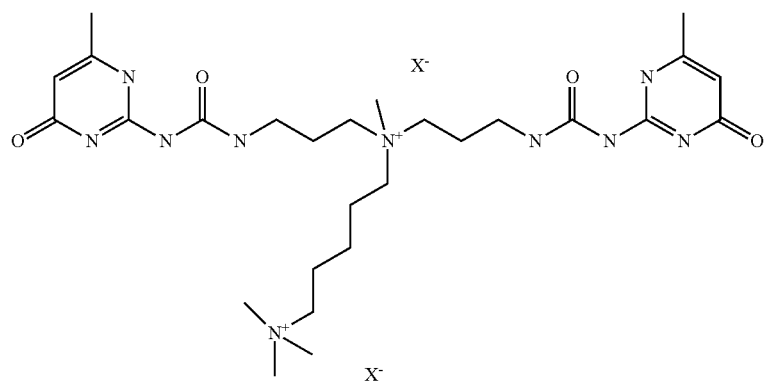
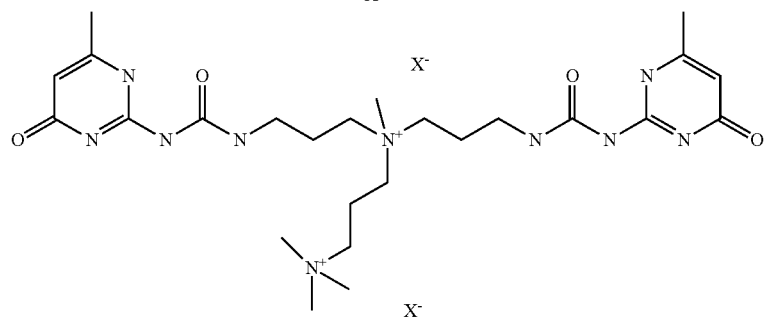

-continued
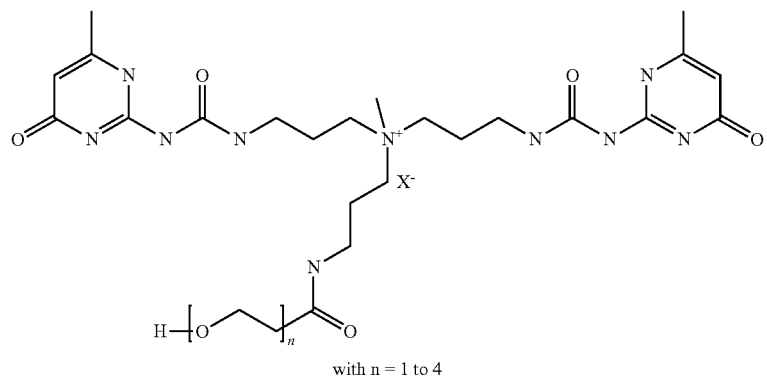
with n = 1 to 4
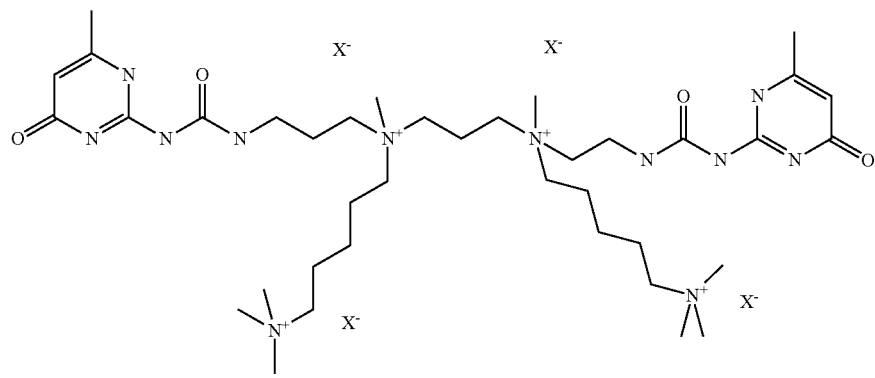
with X = Cl or Br
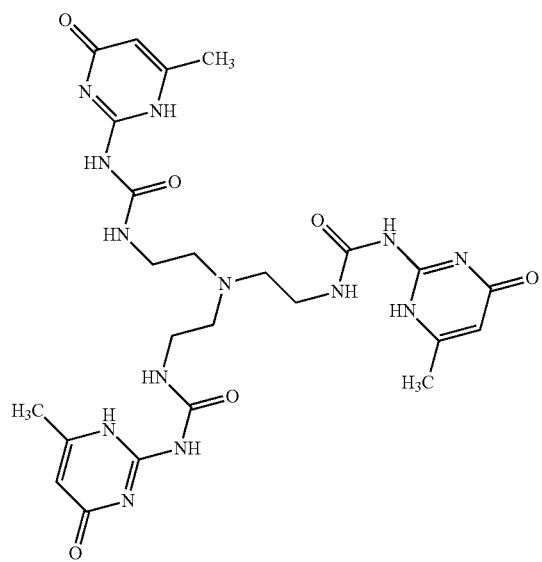

-continued
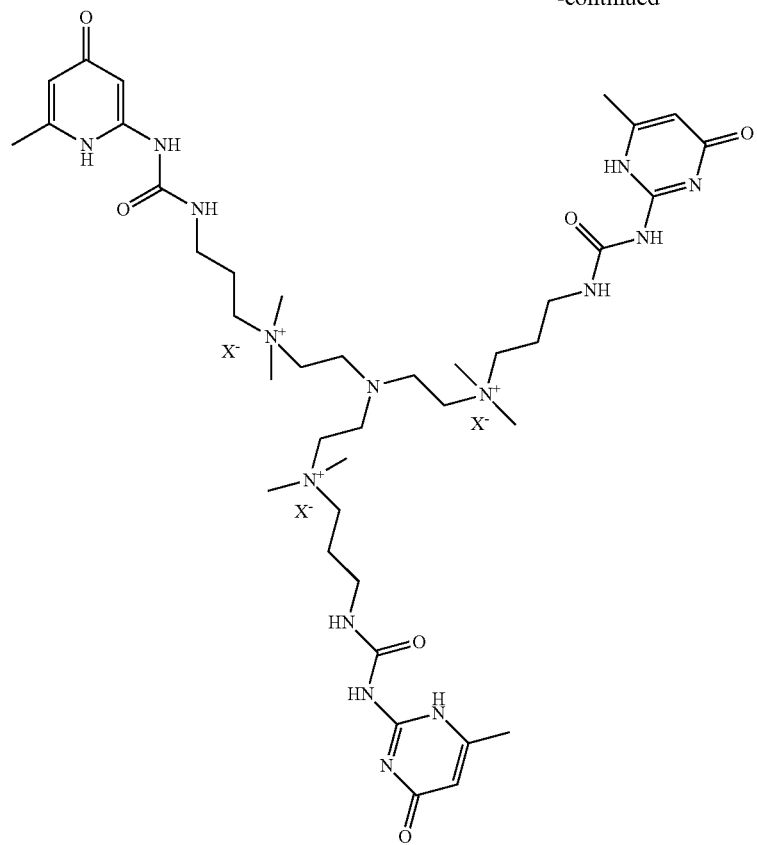
with X = Cl or Br
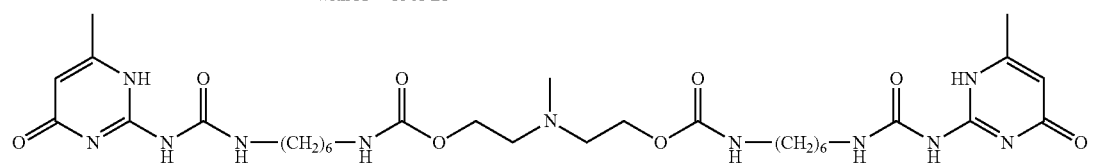
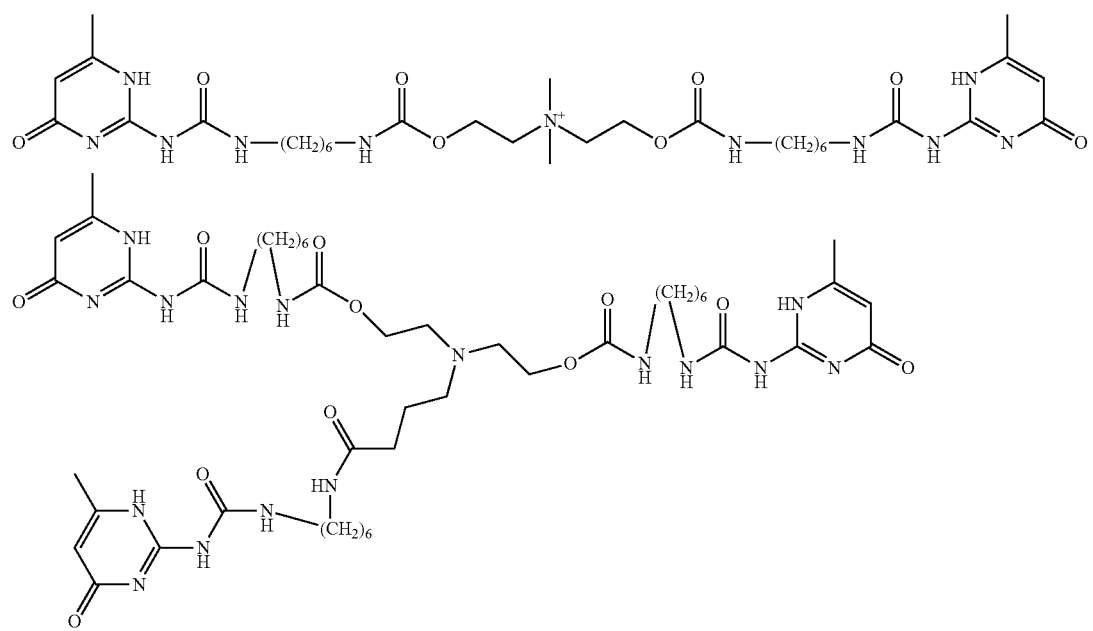

-continued
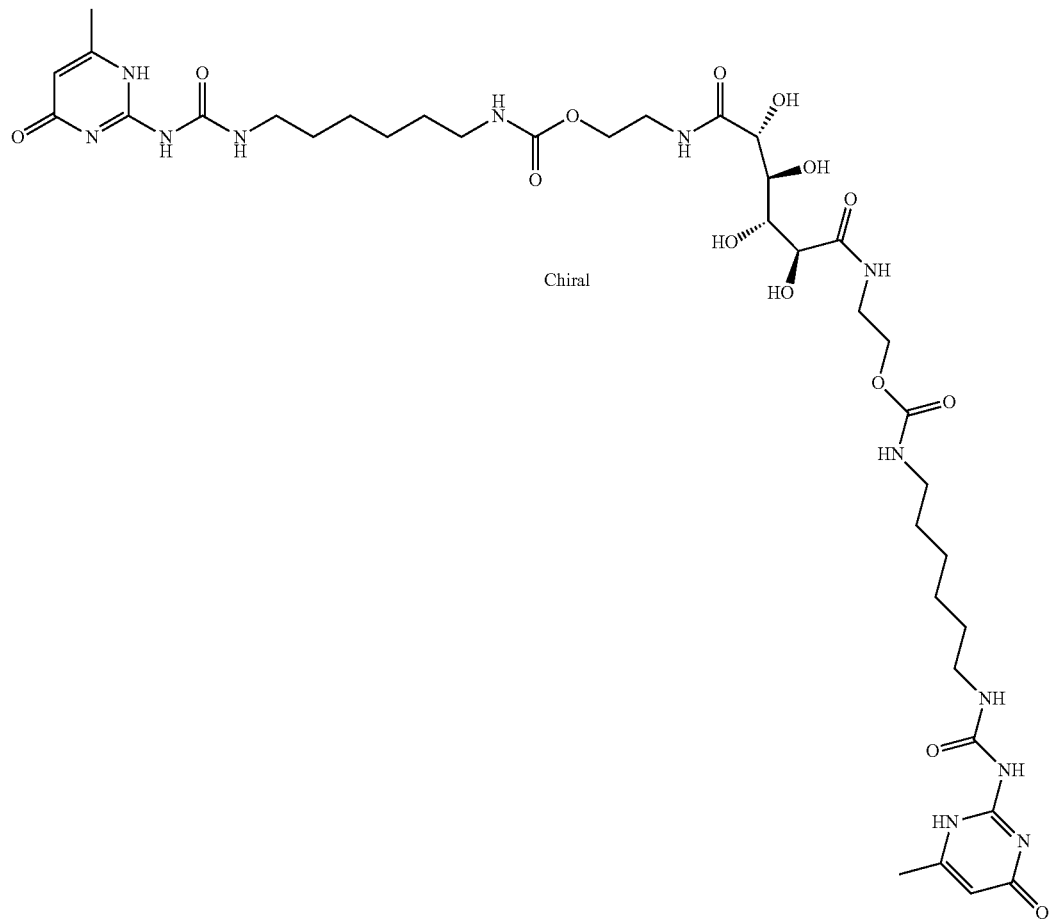
Chiral
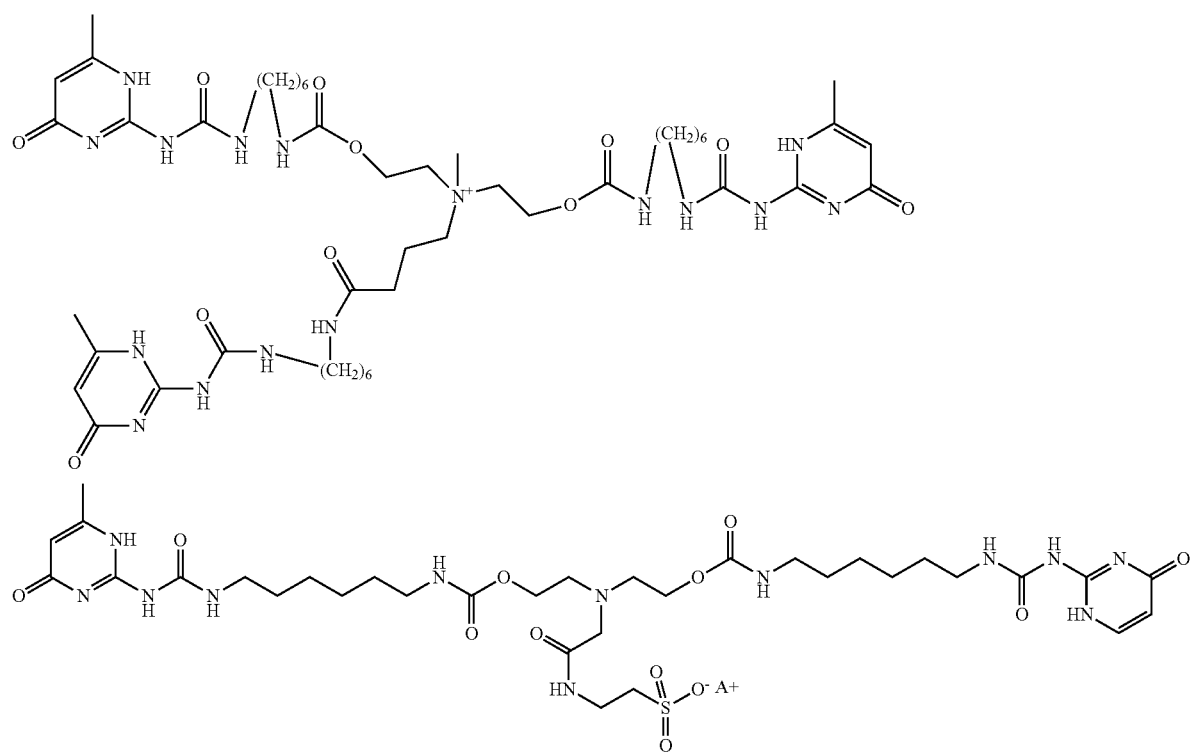
A+ = Na+, K+, NH4+

-continued
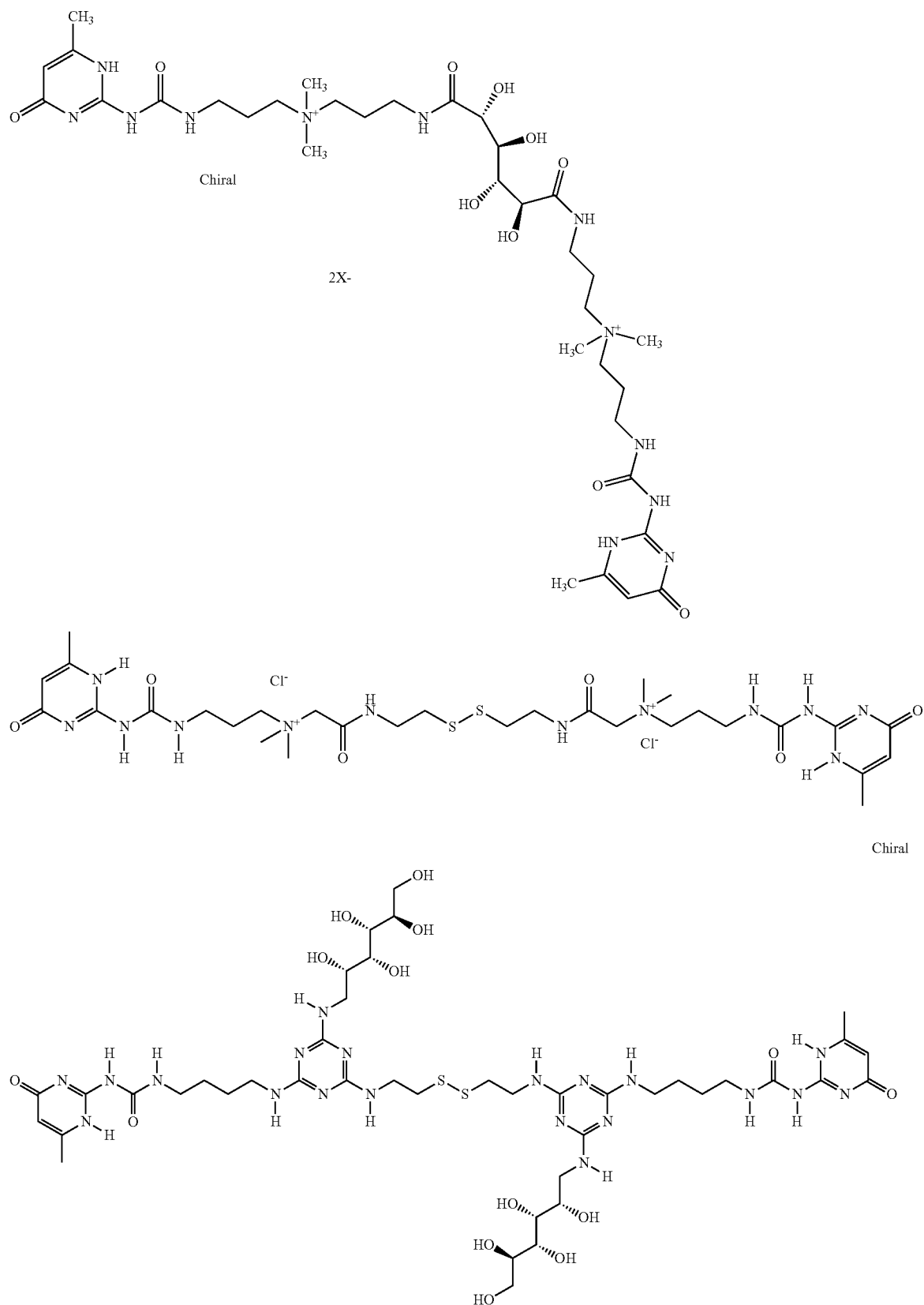

The compositions according to the invention may be in any of the galenic forms conventionally used, and in particular in the form of an aqueous, alcoholic or aqueous-alcoholic, or oily solution or suspension; a solution or a dispersion of the lotion or serum type; an emulsion, in particular of liquid or semi-liquid consistency, of the O/W, W/O or multiple type; a suspension or emulsion of soft consistency of cream (O/W) or (W/O) type; an aqueous or anhydrous gel, or any other cosmetic form. Preferably, the composition is in the form of an aqueous suspension, serum or lotion.

These compositions may be packaged, especially in pump bottles or in aerosol containers, so as to apply the composition in vaporized form or in the form of a mousse. Such packaging forms are indicated, for example, when it is desired to obtain a spray or a mousse, for treating the hair. In these cases, the composition preferably comprises at least one propellant.

The compositions according to the invention comprise a cosmetically acceptable medium, i.e. a medium that is compatible with keratin materials, in particular the skin of the face or of the body, the lips, the hair, the eyelashes, the eyebrows and the nails.

Said medium preferably comprises at least one customary cosmetic ingredient, in particular chosen from propellants; carbon-based oils; silicone oils; C8-C40 alcohols, C8-C40 esters, C8-C40 acids; nonionic surfactants, cationic surfactants, anionic surfactants, amphoteric surfactants, zwitterionic surfactants; sunscreens; moisturizers; antidandruff agents; antioxidants; reducing agents; oxidation bases, couplers, oxidizing agents, direct dyes; hair straightening agents, pearlescent agents and opacifying agents; plasticizers or coalescence agents; hydroxy acids; pigments; fillers; polyols; waxes; thickeners, emulsifiers; polymers; preservatives.

Said medium may also comprise an additional ingredient chosen from water, C1-C7 alcohols, ketones, organic solvents, silicones; waxes; pH agents.

Said medium can of course comprise several cosmetic ingredients appearing in the lists above.

Depending on their nature and the purpose of the composition, the ingredients may be present in normal amounts, which can be readily determined by a person skilled in the art, and which may be, for each ingredient, between 0.01% and 80% by weight.

In one particular embodiment, the composition according to the invention may comprise one or more reducing agents, which may be chosen from thiols, for example cysteine, homocysteine, thiolactic acid, salts of these thiols, phosphines, bisulphite, sulphites, thioglycolic acid, and also esters thereof, especially glyceryl monothioglycolate, and thioglycerol. This reducing agent may also be chosen from borohydrides and derivatives thereof, such as for example borohydride, cyanoborohydride, triacetoxyborohydride and trimethoxyborohydride salts; sodium, lithium, potassium, calcium and quaternary ammonium (tetramethylammonium, tetraethylammonium, tetra-n-butylammonium, benzyltriethylammonium) salts; catecholborane; and mixtures thereof.

The composition may especially comprise water, one or more C1-C7 alcohols, alone or as a mixture with water, and especially a water/ethanol, water/isopropanol or water/benzyl alcohol mixture.

The carbon-based, in particular hydrocarbon-based, oils and/or the silicone oils may be present in a proportion of from 0.01% to 20% by weight relative to the total weight of the composition. Mention may especially be made of hydrogenated or non-hydrogenated plant, animal or mineral oils, saturated or unsaturated, linear or branched, cyclic or aliphatic, hydrocarbon-based synthetic oils, for instance poly(alpha-olefin)s, in particular polydecenes and polyisobutenes; water-soluble or water-insoluble, organomodified or non-organomodified, volatile or non-volatile silicone oils; fluoro or perfluoro oils; mixtures thereof.

The alcohols, the esters and the acids, having 8 to 40 carbon atoms, may be present in a proportion of from 0.01% to 50% by weight, especially 0.1% to 20% by weight, relative to the total weight of the composition.

Mention may especially be made of C12-C32, especially C12-C26, linear-chain or branched-chain fatty alcohols, and in particular cetyl alcohol, stearyl alcohol, cetylstearyl alcohol, isostearyl alcohol, octyldodecanol, 2-butyloctanol, 2-hexyldecanol, 2-undecylpentadecanol, oleyl alcohol or linoleyl alcohol. Mention may also be made of alkoxylated, in particular ethoxylated, C8-C40, especially C16-C20 fatty alcohols, preferably comprising from 10 to 50 mol of ethylene oxide and/or of propylene oxide, such as oleth-12, ceteareth-12 and ceteareth-20, oxypropylenated stearyl alcohol, especially comprising 15 mol of propylene oxide, oxyethylenated lauryl alcohol, especially comprising more than 7 oxyethylenated groups, and also mixtures thereof. Mention may also be made of C16-C40 linear-chain or branched-chain fatty acids, and especially 18 methyleicosanoic acid, coconut oil or hydrogenated coconut oil acids; stearic acid, lauric acid, palmitic acid and oleic acid, behenic acid, and mixtures thereof. Mention may also be made of C16-C40 linear-chain or branched-chain fatty esters, such as esters of polyols derived from fatty acids containing from 8 to 30 carbon atoms, and the oxyalkylenated, and especially oxyethylenated, derivatives thereof, the polyols preferably being chosen from sugars, C2-C6 alkylene glycols, glycerol, polyglycerols, sorbitol, sorbitan, polyethylene glycols, polypropylene glycols, and mixtures thereof.

The silicones may be volatile or non-volatile; mention may especially be made of modified or unmodified polyorganosiloxanes, i.e. polyorganosiloxane oils, gums and resins, as they are or in the form of solutions in organic solvents, or in the form of emulsions or microemulsions.

A person skilled in the art will take care to choose the ingredients which are part of the composition, and also the amounts thereof, in such a way that they are not detrimental to the properties of the compositions of the present invention.

The cosmetic composition according to the invention may be in the form of a care, cleansing and/or makeup product for the skin of the body or the face, the lips, the eyebrows, the eyelashes, the nails and the hair, a suntan or self-tanning product, a body hygiene product, a hair product, especially a hair care, cleansing, conditioning or dyeing product. It especially has a particularly advantageous application in the hair-related field, especially for caring for, cosmetically treating or cleansing the hair.

The hair compositions are preferably shampoos, cream rinses, care gels, lotions or creams, conditioners, hair restructuring lotions; lotions or gels for combating hair loss, antiparasitic shampoos, antidandruff lotions or shampoos, or shampoos for treating seborrhoea. They may also be a hair dyeing product, especially an oxidation dyeing product, optionally in the form of a dye shampoo; in the form of a permanent-waving, hair-straightening or bleaching composition, or else in the form of a rinse-out or leave-in composition, to be applied before or after dyeing, bleaching, permanent-waving or hair-straightening, or else between the two steps of a permanent-waving or hair-straightening operation.

The composition according to the invention has an advantageous application in the care and the cosmetic treatment, especially the protection, of the hair, in particular weakened and/or damaged hair, for example hair weakened and/or damaged by chemical or mechanical treatments; use may especially be made of the compounds according to the invention in post-treatment, after a hair dyeing, bleaching or straightening step.

One subject of the invention is therefore a method for cosmetically treating, in particular for making up, caring for, cleansing or dyeing keratin materials, especially the skin of the body or of the face, the lips, the nails, the hair and/or the eyelashes, comprising the application of a cosmetic composition comprising at least one compound according to the invention to said materials.

Preferably, it is a cosmetic treatment method for conditioning and/or caring for the hair, in particular for giving it body and/or liveliness, or improving the disentangling, smoothing, combability, repair and manageability of the head of hair. It may be a method for repairing and/or protecting damaged or weakened hair.

In one particular embodiment of the treatment method, the composition according to the invention may be applied all at once, or in several applications (multi-application).

Thus, it is possible to apply a composition comprising the compounds according to the invention, in an amount, for example, of from 0.05% to 15%, especially 0.1% to 5% by weight, to the hair a first time, to leave it in for 2 to 20, especially 5 to 15, minutes, optionally while heating at a temperature below 65° C., or else with a smoothing iron or a crimping iron, for example for a few seconds, and then, optionally, to dry the hair before applying the composition a second time, and to again leave it in for 2 to 20, especially 10, minutes, before optionally heating at a temperature below 65° C., or else with a smoothing iron or a crimping iron, for example for a few seconds, and then to dry or allow to dry. It is possible to carry out a third application of the composition. This multi-application of the composition may especially make it possible to improve the penetration of the compounds inside the hair, and therefore to improve the repair of the hair in situ.

As well as that indicated above, the compounds according to the invention have a very particular use in a cosmetic hair treatment method, before, during or after a cosmetic hair dyeing, bleaching, permanent-waving, straightening or smoothing treatment; they also have an application in a maintenance method for damaged hair, especially hair damaged by external attacks such as UV, pollution, repeated brushing and chlorinated water.

The expression "during a treatment" is understood to mean use as a mixture with one or other of the elements of the treatment kit or between the various steps of a treatment, for example a permanent-waving treatment.

Thus, another subject of the invention is a kit comprising, on the one hand, a composition for dyeing, bleaching, permanent waving, straightening or smoothing the hair and, on the other hand, a cosmetic composition comprising at least one compound of formula (I).

The two compositions may be applied one after the other, with optional rinsing between the two applications; they may also be mixed just before use and application of the mixture. A subsequent rinsing and/or drying step may be envisaged.

In one particular embodiment, one of the compositions of the kit comprises at least one reducing agent, in particular chosen from the list given above; the reducing agent may especially be present in the hair dyeing, bleaching, permanent-waving, straightening or smoothing composition, the compound of formula (I) being present in the other composition of the kit.

The invention is illustrated in greater detail in the following exemplary embodiments.

Example 1: N-(4-aminobutyl)-N'-(6-methyl-4-oxo-1,4-dihydropyrimidin-2-yl)urea hydrochloride (1)

1/ Preparation of tert-butyl[4-({[(6-methyl-4-oxo-1,4-dihydropyrimidin-2-yl)amino]carbonyl}amino)butyl]carbamate (1B) from Isocytosine Having a Carbamic Function Activated by Carbonyldiimidazole (1A) (Procedure No. 1)

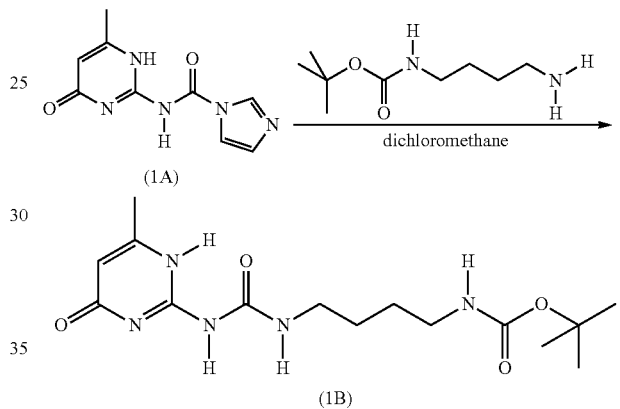

Added to a solution of 1.72 g of tert-butyl(4-aminobutyl)carbamate (9.1 mmol) in 50 ml of dichloromethane, are 2 g of 2-(1-imidazolylcarbonylamino)-6-methyl-4[1H]-pyrimidinone 1A (9.1 mmol) prepared according to the procedure described by E. W. Meijer et al., J. Am. Chem. Soc., 2003, 125, p. 6860. The solution is stirred at reflux for 4 hours. The end product is obtained by precipitation in acetone. After filtering and washing with acetone, the end product is dried under reduced pressure and 4.02 g (11.8 mmol) of pure product 1B are obtained in the form of a white powder with a yield of greater than 99% (hygroscopic product).

$^1$H NMR (DMSO): δ 1.37 ppm (s, 9H), 2.11 ppm (s, 3H), 2.88-2.96 ppm (m, 2H), 3.09-3.16 ppm (m, 2H), 3.17-3.20 ppm (m, 4H), 4.07-4.13 ppm (m, 1H).

2/ Preparation of N-(4-aminobutyl)-N'-(6-methyl-4-oxo-1,4-dihydropyrimidin-2-yl)urea hydrochloride (1) (Procedure No. 2)

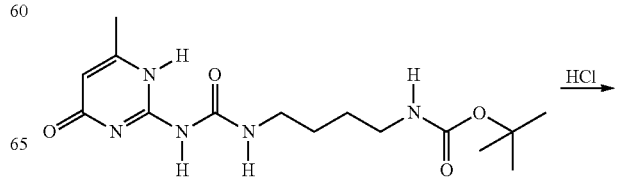

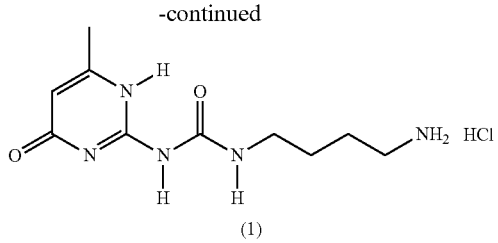

Added to a solution of 3.02 g of tert-butyl[4-({[(6-methyl-4-oxo-1,4-dihydropyrimidin-2-yl)amino]carbonyl}amino)butyl]carbamate (8.9 mmol) prepared above, in 10 ml of ethyl acetate, are 9.28 g of 35% hydrochloric acid (89.5 mmol). The solution is stirred at 5° C. for 1 hour. The end product is obtained by precipitation in acetone. After filtering and washing with acetone, the end product is dried under reduced pressure and 2.28 g (9.5 mmol) of desired product (1) are obtained in the form of a white powder with a yield of greater than 99% (hygroscopic product).

Melting point: 131° C.

$^1$H NMR (DMSO): δ 1.30-1.78 ppm (m, 4H), 2.23 ppm (s, 3H), 2.73-2.87 ppm (m, 2H), 3.10-3.25 ppm (m, 2H), 6.04 ppm (m, 1H).

Example 2: N-[3-(dimethylamino)propyl]-N'-(6-methyl-4-oxo-1,4-dihydropyrimidin-2-yl)urea (2)

Preparation from 6-Methylisocytosine (2A) and Carbonyldiimidazole (2B)

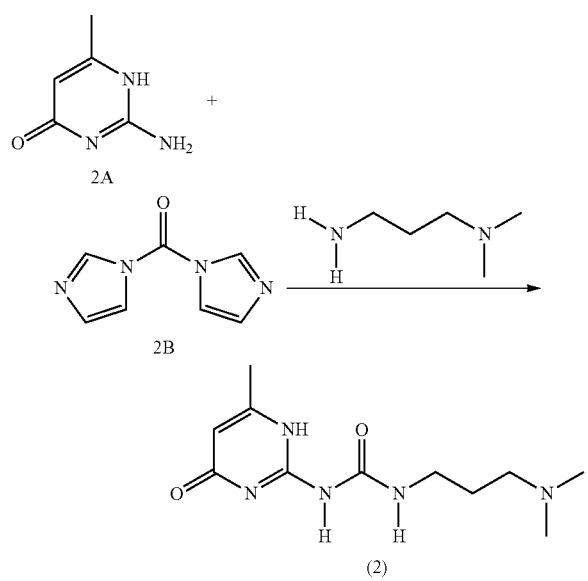

Added to a suspension of 5 g of 6-methylisocytosine (40 mmol) in 100 ml of ethyl acetate are 8.42 g of carbonyldiimidazole (52 mmol). The solution is stirred for 12 hours at reflux, then 8 hours at room temperature. 5.03 ml of dimethylaminopropylamine (40 mmol) are added. The solution is stirred for 6 hours at reflux. The end product is obtained by filtration on a Büchner funnel. The end product is dried under reduced pressure and 9.6 g (38 mmol) of desired product are obtained in the form of a white powder with a yield of 95%.

$^1$H NMR (DMSO): δ 1.77 ppm (t, 2H), 2.19 ppm (s, 3h), 2.71 ppm (s, 6H), 3.28 ppm (t, 2H), 5.84 ppm (s, 1H).

Example 3: trimethyl-{3-[3-(6-methyl-4-oxo-1,4-dihydropyrimidin-2-yl)ureido]-propyl}ammonium chloride (3)

Preparation from Isocytosine Having a Carbamic Function Activated by Carbonyldiimidazole

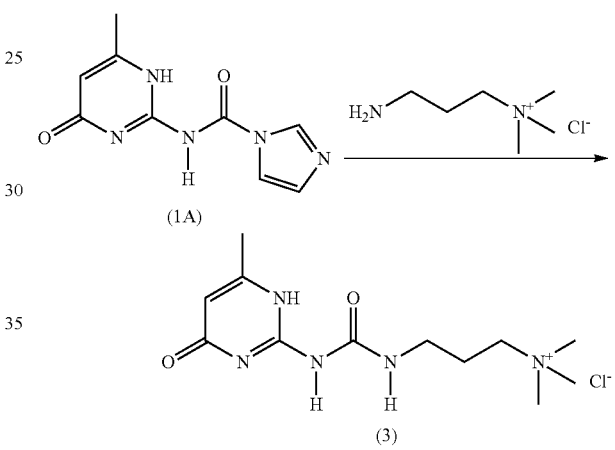

The product is prepared according to procedure no. 1 described in Example 1.

6 g (20.2 mmol) of pure desired product are obtained in the form of a white powder with a yield of 69%.

Melting point: 143.49° C.

$^1$H NMR (D$_2$O): δ 1.97-2.07 ppm (m, 2H), 2.17-2.22 ppm (m, 3H), 3.05-3.08 ppm (m, 9H), 3.10-3.13 ppm (m, 2H), 3.26-3.32 ppm (m, 3H), 3.33-3.37 ppm (m, 2H), 5.86-5.98 ppm (m, 2H).

Example 4: 1-[3-(dimethylamino)propyl]-3-(6-{[(6-methyl-4-oxo-1,4-dihydropyrimidin-2-yl)carbamoyl]amino}hexyl)urea (4)

Preparation from Isocytosine Having an Isocyanate Function

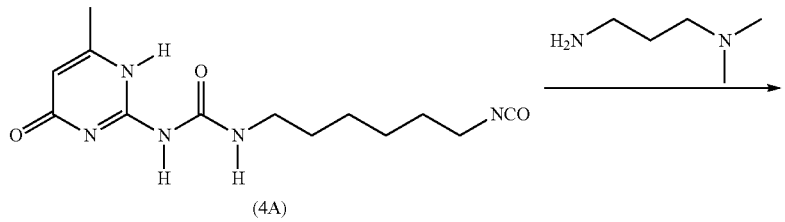

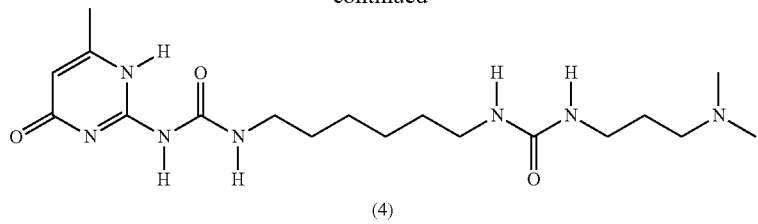

(4)

The product is prepared according to procedure no. 1 described in Example 1, from 1-(6-isocyanatohexyl)-3-(6-methyl-4-oxo-1,4-dihydropyrimidin-2-yl)urea prepared according to the procedure described by E. W. Meijer et al., *J. Am. Chem. Soc.*, 2003, 125, p. 6860.

6.2 g (15.7 mmol) of pure desired product are obtained in the form of a white powder with a yield of 92%.

$^1$H NMR (DMSO+TFA): δ 1.37 ppm (m, 8H); 1.76 ppm (t, 2H); 2.25 ppm (s, 3H); 2.74 ppm (d, 6H); 3.07 ppm (m, 8H); 6.03 ppm (s, 1H).

Example 5: N-(4-{[amino(imino)methyl]amino}butyl)-N'-(6-methyl-4-oxo-1,4-dihydropyrimidin-2-yl)urea (5)

Preparation from Isocytosine Having a Carbamic Function Activated by Carbonyldiimidazole (1A)

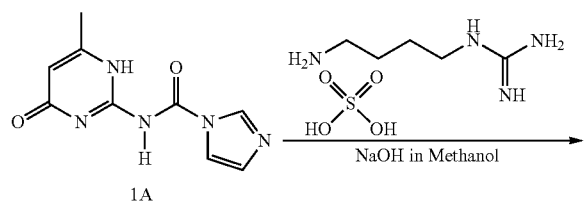

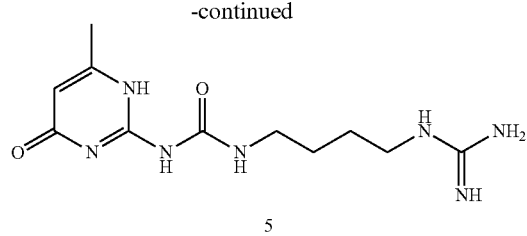

5

The product is prepared according to procedure no. 1.

5.8 g (20.6 mmol) of pure desired product are obtained in the form of a white powder with a yield of 47%.

Melting point: 197.1° C.

$^1$H NMR (DMSO+CD$_3$COOD): δ 1.48 ppm (m, 4H); 2.14 ppm (m, 3H); 3.11-3.17 ppm (m, 4H); 5.84 ppm (m, 1H).

Example 6: 1-(6-methyl-4-oxo-1,4-dihydropyrimidin-2-yl)-3-octadec-9-enylurea (6)

Preparation from Isocytosine Having a Carbamic Function Activated by Carbonyldiimidazole 1A

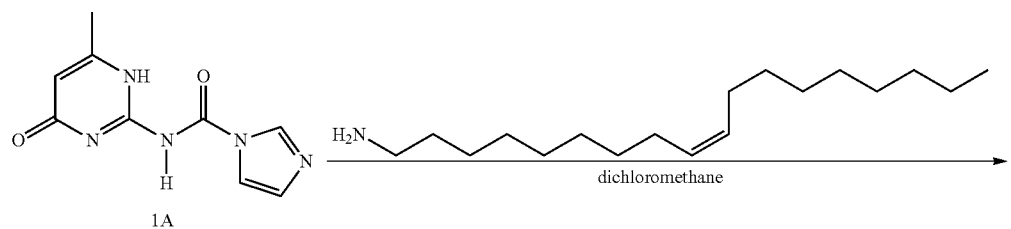

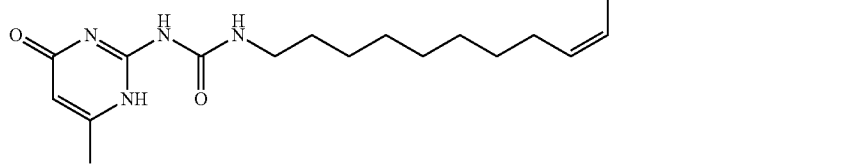

6

The product is prepared according to procedure no. 1.

4.2 g (10 mmol) of pure desired product are obtained in the form of a white powder with a yield of 73%.

Melting point: 114.4° C.

$^1$H NMR (DMSO): δ 0.85-0.91 ppm (m, 3H), 1.18-1.39 ppm (m, 24H), 1.54-1.64 ppm (m, 2H), 1.94-2.05 ppm (m, 2H), 2.14-2.39 ppm (m, 3H), 3.15-3.43 ppm (m, 2H), 5.20-5.55 ppm (m, 2H), 5.67-5.97 ppm (m, 1H).

Example 7: (2S)-6-amino-2-({[(6-methyl-4-oxo-1,4-dihydropyrimidin-2-yl)-amino]carbonyl}amino) hexanoic acid (7)

1/ Preparation of tert-butyl(2S)-6-[(tert-butoxycarbonyl)amino]-2-({[(6-methyl-4-oxo-1,4-dihydropyrimidin-2-yl)amino]carbonyl}amino)hexanoate (7A) from Isocytosine Having a Carbamic Function Activated by Carbonyldiimidazole (1A)

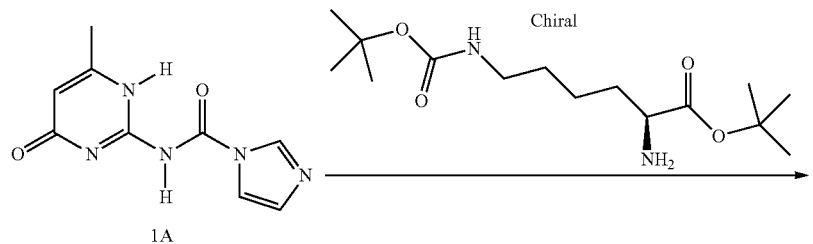

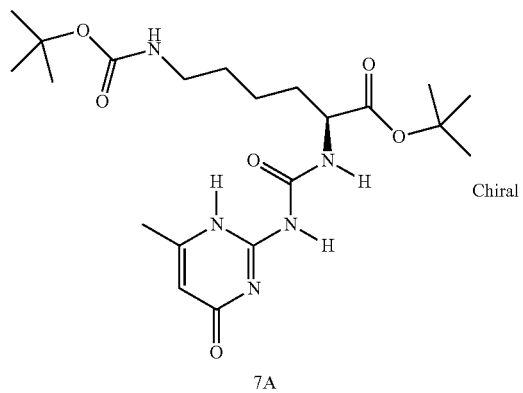

7A

The product (7A) is prepared according to procedure no. 1.

4.6 g (10.1 mmol) of pure desired product are obtained in the form of a white powder with a yield of 69%.

$^1$H NMR (DMSO): δ 1.26 ppm (m, 2H); 1.37 ppm (s, 9H); 1.42 ppm (s, 9H); 1.65 ppm (m, 2H); 2.13 ppm (s, 3H); 2.89-2.91 ppm (q, 2H); 4.14-4.15 ppm (m, 1H); 5.81 ppm (s, 1H).

2/ Preparation of Desired Product (7) from (7A)

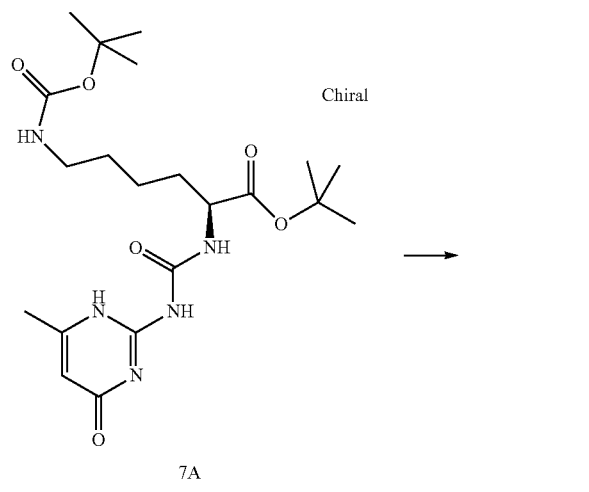

7A

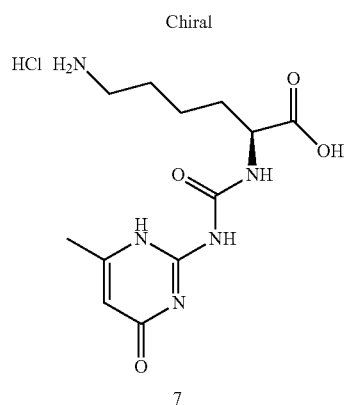

7

The desired product (7) is prepared according to procedure no. 2 described in Example 2.

4.5 g (15.2 mmol) of pure product are obtained in the form of a white powder with a yield >99%.

$^1$H NMR (DMSO): δ 1.39 ppm (m, 2H); 1.56-1.58 ppm (m, 2H); 1.90 ppm (m, 2H); 2.18 ppm (s, 3H); 2.75 ppm (m, 2H); 4.19-4.20 ppm (d, 1H); 5.93 ppm (s, 1H).

Example 8: (2S)-2-({[(6-methyl-4-oxo-1,4-dihydro-pyrimidin-2-yl)amino]-carbonyl}amino)pentanedioic acid (8)

1/ Preparation of di-tert-butyl(2S)-2-({[(6-methyl-4-oxo-1,4-dihydropyrimidin-2-yl)-amino]carbonyl}amino)pentanedioate (8A) from Isocytosine Having a Carbamic Function Activated by Carbonyldiimidazole (1A)

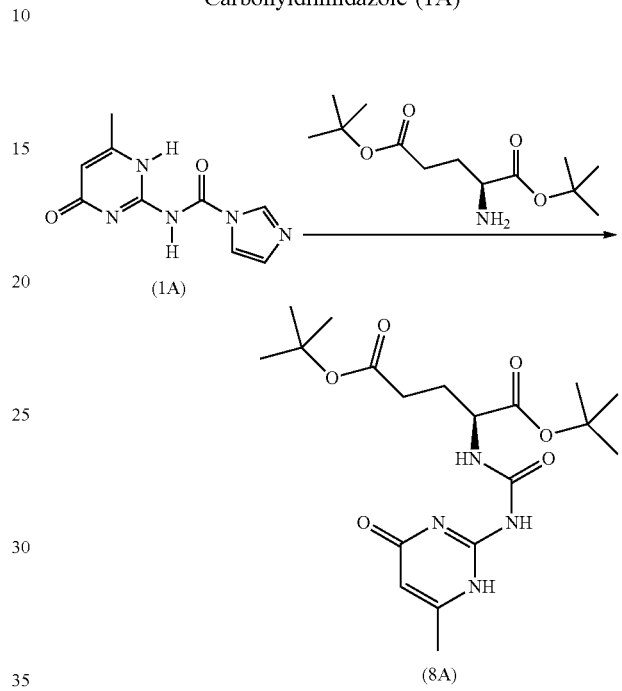

The product (8A) is prepared according to procedure no. 1.

11.7 g (28.5 mmol) of pure product (8A) are obtained in the form of a white powder with a yield >99%.

$^1$H NMR (DMSO): δ 1.38-1.46 ppm (d, 18H); 1.78-1.86 ppm (m, 1H), 1.78-1.86 ppm (m, 1H); 2.14 ppm (s, 3H); 2.24-2.31 ppm (m, 2H); 4.17-4.27 ppm (m, 1H); 5.82 ppm (s, 1H).

2/ Preparation of (2S)-2-({[(6-methyl-4-oxo-1,4-dihydropyrimidin-2-yl)amino]-carbonyl}amino)pentanedioic acid (8)

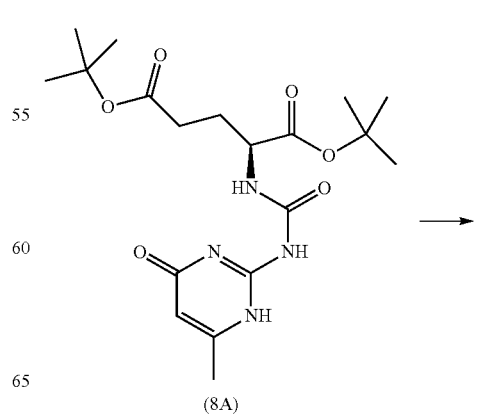

(8A)

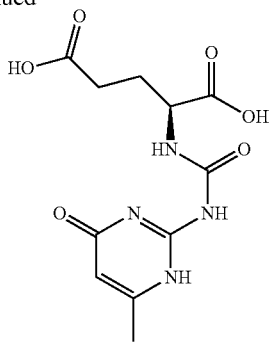

(8)

The product is prepared according to procedure no. 2.

9.8 g (32.9 mmol) of pure product (8) are obtained in the form of a white powder with a yield >99%.

$^1$H NMR (D$_2$O): δ 2.05 ppm (m, 1H); 2.24 ppm (m, 1H); 2.27 ppm (s, 3H); 2.5 ppm (m, 2H); 4.42-4.43 ppm (m, 1H); 6.04 ppm (s, 1H).

Example 9: (2R,3R,4R,5R)-2,3,5,6-tetrahydroxy-N-4-{[(6-methyl-4-oxo-1,4-dihydropyrimidin-2-yl)carbamoyl]amino}butyl)-4-{[(2S,3R,4S,5R,6R)-3,4,5-trihydroxy-6-(hydroxymethyl)tetrahydro-2H-pyran-2-yl]oxy}hexanamide (10)

Preparation of (10) from N-(4-aminobutyl)-N'-(6-methyl-4-oxo-1,4-dihydropyrimidin-2-yl)urea hydrochloride (1) (Procedure No. 3)

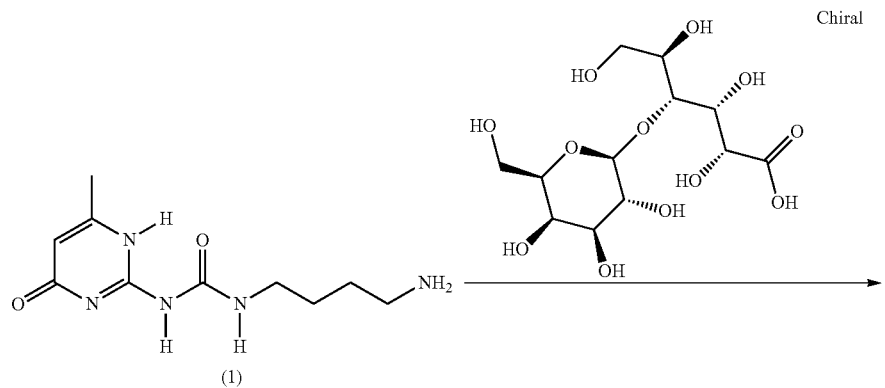

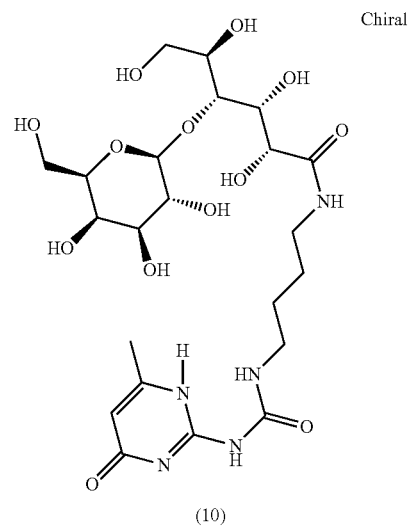

(10)

Added to a suspension of 0.5 g of lactobionic acid (1.4 mmol) in 40 ml of ethanol are 0.35 g of N-(4-aminobutyl)-N'-(6-methyl-4-oxo-1,4-dihydropyrimidin-2-yl)urea hydrochloride (1.27 mmol) and 0.32 g of diisopropylethylamine (2.56 mmol). The solution is stirred for 6 hours at reflux. The end product is obtained by reverse-phase purification, eluting with acetonitrile/water 5/5 with 0.2% of trifluoroacetic acid.

0.45 g (0.78 mmol) of pure product (10) is obtained in the form of a white powder with a yield of 62%.

$^1$H NMR (DMSO): δ 1.47 ppm (m, 4H); 2.12 ppm (s, 3H); 3.12 ppm (m, 4H); 3.25-4.36 ppm (m, 13H); 5.78 ppm (s, 1H).

Example 10: (2-{2-[3-(6-methyl-4-oxo-1,4-dihydro-pyrimidin-2-yl)ureido]ethyl-disulphanyl}ethyl)carbamic acid tert-butyl ester (11)

Preparation of (11) from Isocytosine Having a Carbamic Function Activated by Carbonyldiimidazole (1A)

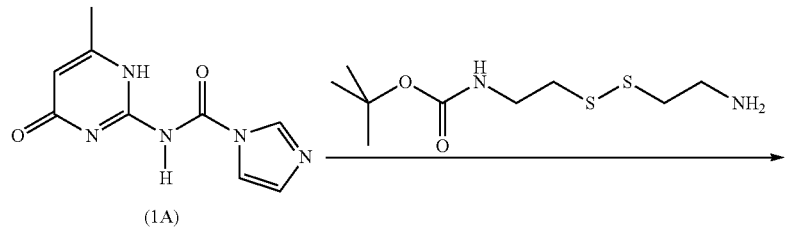

(1A)

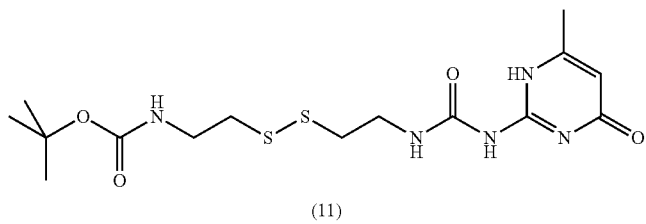

(11)

The product (11) is prepared according to procedure no. 1.

4.8 g (10 mmol) of pure product (11) are obtained in the form of a white powder with a yield of 86%.

Melting point: 182.15° C.

$^1$H NMR (DMSO): δ 1.31-1.45 ppm (s, 9H), 2.11-2.14 ppm (m, 3H), 2.73-2.81 ppm (m, 2H), 2.81-2.90 ppm (m, 2H), 3.15-3.26 ppm (m, 2H), 3.41-3.51 ppm (m, 2H), 5.76-5.81 ppm (m, 1H).

Example 11: 4-[(4-{[(6-methyl-4-oxo-1,4-dihydropyrimidin-2-yl)carbamoyl]-amino}butyl)amino]-4-oxobutyl imidothiocarbamate hydrochloride (12)

1/ Preparation of 4-chloro-N-(4-{[(6-methyl-4-oxo-1,4-dihydropyrimidin-2-yl)-carbamoyl]amino}butyl)butanamide (12A) from N-(4-aminobutyl)-N'-(6-methyl-4-oxo-1,4-dihydropyrimidin-2-yl)urea hydrochloride (1)

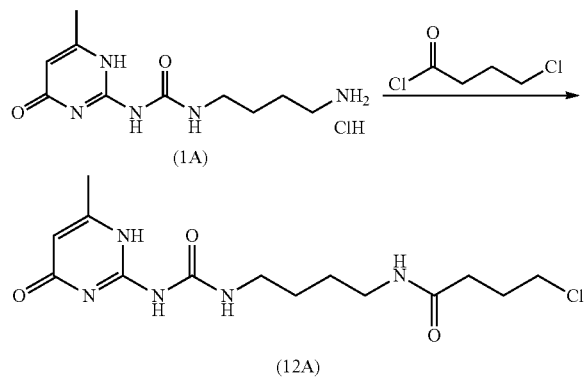

Added to a solution of 20 g of N-(4-aminobutyl)-N'-(6-methyl-4-oxo-1,4-dihydropyrimidin-2-yl)urea hydrochloride (1) (70 mmol) in 200 ml of water cooled to 0° C. are 11.6 g of sodium hydroxide (0.29 mol) and 24.4 ml of chlorobutyl chloride (0.22 mol). The solution is stirred for 18 hours at room temperature. The product obtained is filtered and then dried under reduced pressure.

14.2 g (41.4 mmol) of pure product (12A) are obtained in the form of a white powder with a yield of 54%.

$^1$H NMR (DMSO): δ 1.41 ppm (s, 4H); 1.93 ppm (m, 2H); 2.10 ppm (s, 3H); 2.20 ppm (t, 2H); 3.09 ppm (m, 2H); 3.62 ppm (m, 2H); 5.79 ppm (s, 1H).

2/ Preparation of (12) from 4-chloro-N-(4-{[(6-methyl-4-oxo-1,4-dihydropyrimidin-2-yl)carbamoyl]amino}butyl)butanamide (12A)

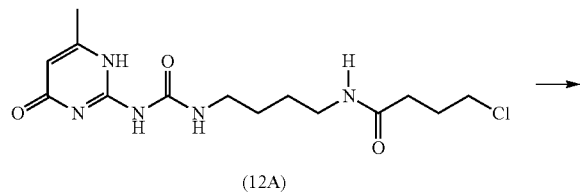

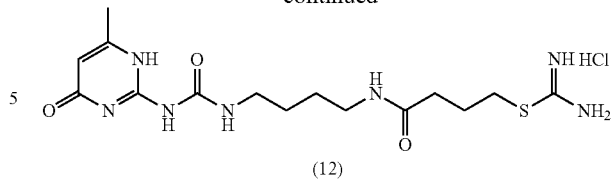

Added to a solution of 10.7 g of 4-chloro-N-(4-{[(6-methyl-4-oxo-1,4-dihydropyrimidin-2-yl)carbamoyl]amino}butyl)butanamide (12A) (3 mmol) in 100 ml of 2-propanol are 2.84 g of thiourea (4 mmol). The solution is stirred for 17 hours at reflux. The product obtained is filtered and then dried under reduced pressure.

10.7 g (25.5 mmol) of pure product (12) are obtained in the form of a yellow powder with a yield of 82%.

$^1$H NMR (DMSO): δ 1.44 ppm (t, 4H); 1.83 ppm (q, 2H); 2.09 ppm (s, 3H); 2.24 ppm (t, 2H); 3.11 ppm (m, 6H); 5.76 ppm (s, 1H).

Example 12: 1-[2-(3,4-dihydroxyphenyl)ethyl]-3-(6-methyl-4-oxo-1,4-dihydropyrimidin-2-yl)urea (13)

Preparation of (13) from Isocytosine Having a Carbamic Function Activated by Carbonyldiimidazole (1A)

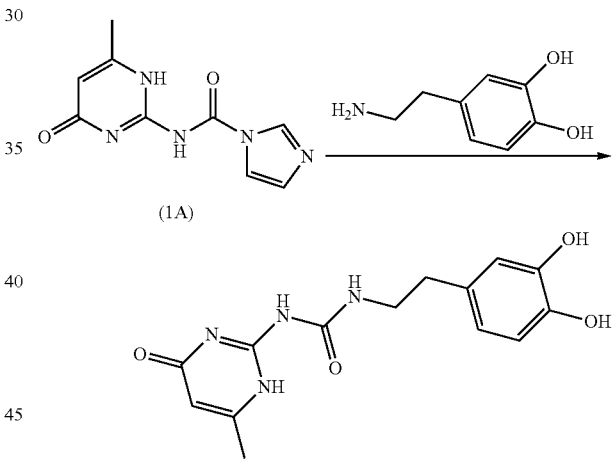

The product is prepared according to procedure no. 1.

11.1 g (36.5 mmol) of pure product (13) are obtained in the form of a white powder with a yield of 80%.

Melting point: 266.28° C.

$^1$H NMR (DMSO): δ 1.95-2.15 ppm (s, 3H); 2.52-2.62 ppm (t, 2H); 5.76 ppm (s, 1H); 3.33 ppm (t, 2H); 6.46-6.66 ppm (m, 3H).

Example 13: Improvement of Hair Straightening

Applied to hair (originally curly hair of curliness IV) straightened by an alkaline hair-straightening product (Goldys—2% active sodium hydroxide) is the following composition, with an amount of product/amount of hair ratio (g/g) of 2, without rinsing:

5% by weight of compound (2) from Example 2 qs for 100% distilled water

Observations are made at T0.

The locks are then washed once or 5 times using Ultra Mild shampoo (Garnier), then dried. Observations are made at T1 (after 1 shampoo wash) and at T5 (after 5 shampoo washes).

The control locks are treated with a composition comprising 100% distilled water.

It is observed that with a treatment according to the invention, at T0, the hair-straightening efficiency is improved compared to a hair-straightening operation that has been subjected to the control post-treatment (only constituted of distilled water). This improvement in the hair-straightening efficiency persists after 1 and 5 shampoo washes.

A porosity measurement of the various locks of hair using a fluorescent probe shows that the improvement in the hair-straightening efficiency at T0 is not accompanied by an increase of the internal porosity of the hair: indeed, the control hair and the hair post-treated according to the invention have an equivalent porosity, after 5 shampoo washes.

Via a post-treatment according to the invention, on hair straightened using sodium hydroxide, it is possible to obtain hair-straightening performances superior to those obtained without treatment, without damaging the fibre further.

Example 14: Reduction of the Concentration of Alkaline Agent in the Hair-Straightening Formulation The composition from Example 14 is applied as post-treatment for a hair-straightening formula containing 1.75% by weight of sodium hydroxide (i.e. a reduction of 0.25% of sodium hydroxide compared to a standard hair-straightening formula containing 2% of sodium hydroxide).

Identical hair-straightening performances are observed at T0 between:
- the standard hair-straightening formula (2% sodium hydroxide), without post-treatment and
- the hair-straightening formula with a lower sodium hydroxide concentration (1.75% of sodium hydroxide), the application of which is followed by the post-treatment with the composition from Example 14.

Example 15

Application of a (14)+(1) Mixture to Locks of Sensitized Hair.

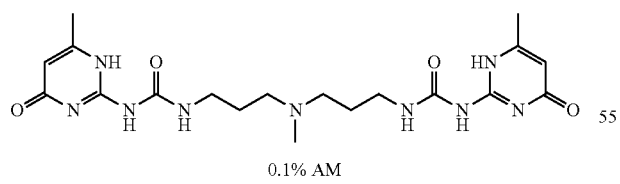

0.1% AM (14)

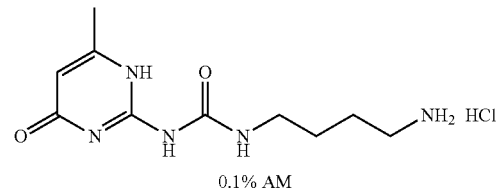

0.1% AM (1)

AM: active material

1/ Preparation of the Solution

The following are mixed:
- 30 mg of N,N''-[(methylimino)dipropane-3,1-diyl]bis[N'-(6-methyl-4-oxo-1,4-dihydropyrimidin-2-yl)urea] (14) (0.06 mmol) and
- 3 mg of 1-(4-aminobutyl)-3-(6-methyl-4-oxo-1,4-dihydropyrimidin-2-yl)urea hydrochloride (0.12 mol) (1) prepared in Example 1,
in 29.94 ml of water.

The mixture is stirred vigorously for 30 minutes at room temperature. A colourless translucent solution is obtained.

2/ Application to Hair

The tests are carried out on 1 g locks of sensitized hair.

The hair is wetted with water, shampooed with 0.4 g of shampoo constituted of 15% sodium lauryl sulphate in water, and then rinsed.

The hair is pretreated with 10 ml of a 0.2N reducing solution of thioglycolic acid for 15 minutes at 30° C. The hair is then rinsed with water.

The hair undergoes the following post-treatment, repeated three times: 10 ml of solution prepared above are applied to the lock of hair for 10 minutes at 60° C. The lock is then wrung out and then left for 10 minutes at room temperature.

A significant increase in the rigidity of the lock post-treated according to the invention (around 15% increase), compared with a control lock, post-treated with water, is observed.

Example 16

In a comparable manner to Example 15, a post-treatment is applied using a composition comprising the compound (5) prepared in Example 5, instead of the compound (1).

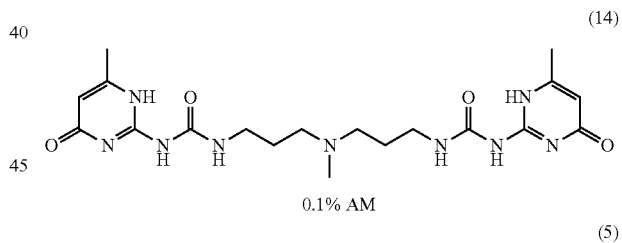

0.1% AM (14)

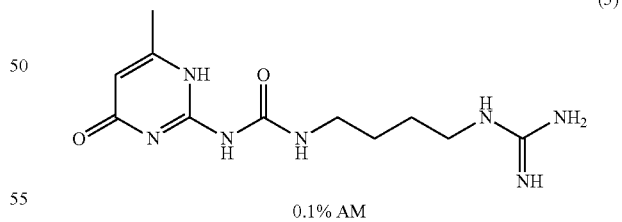

0.1% AM (5)

A significant increase in the rigidity of the lock post-treated according to the invention (around 23% increase), compared with a control lock, post-treated with water, is observed.

Example 17

In a comparable manner to Example 15, a post-treatment is applied using a composition comprising the compound (15) instead of the compound (14).

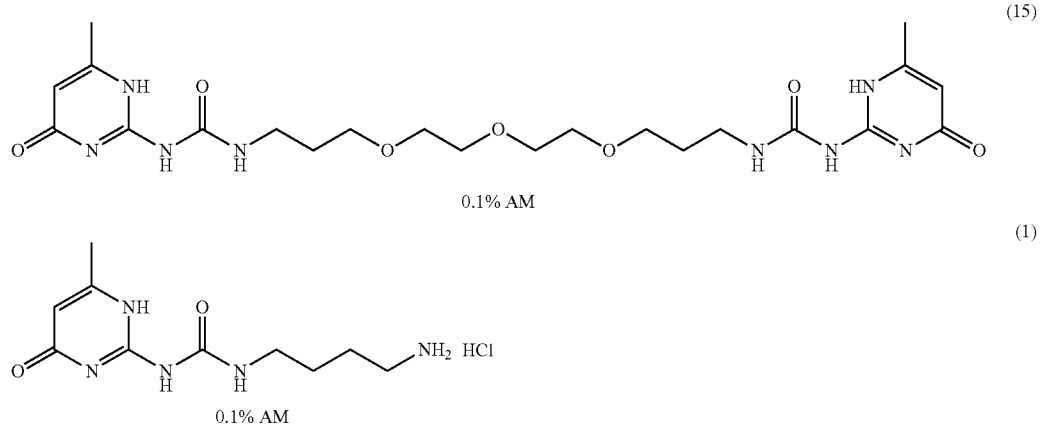

0.1% AM (15)

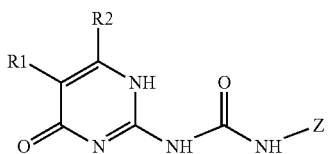

0.1% AM (1)

A significant increase in the rigidity of the lock post-treated according to the invention (around 33% increase), compared with a control lock, post-treated with water, is observed.

The invention claimed is:

1. A method for the cosmetic treatment of a keratin material, comprising applying to said material a cosmetic composition comprising, in a physiologically acceptable medium, at least one compound of formula (I), salts thereof, isomers thereof, solvates thereof, and the tautomeric forms thereof:

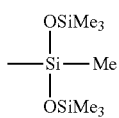

(I)

in which:
R1 and R2, independently of one another, represent H, —OH, —NRR', wherein R and R', individually are H or a linear or branched C1-C12 alkyl radical; or a carbon-based group, which optionally contains one or more heteroatoms;

Z represents a monovalent radical chosen from:
(i) a hydrogen atom,
(ii) a linear or branched C1 to C32 alkyl radical,
(iii) a linear or branched C2 to C32 alkene radical, comprising one or two C=C double bonds;
(iv) a C1-C32 alkyl group substituted with a C6-C10 aryl group and optionally substituted with 1 to 8 groups chosen from —OH, —OR, —SH, —SR, —SO₃H, —SO₃R, —SO₂NRR', —COOH, —COOR, —CONRR', —NR—C(O)—NRR', —NRR' and —N⁺RR'R", with each R, R' and R" individually being H or C1-C6 alkyl; and the substituents of formula (a) to (h) below:

(a)

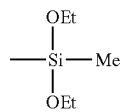

-continued (b)

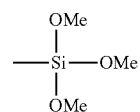

(c)

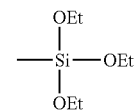

(d)

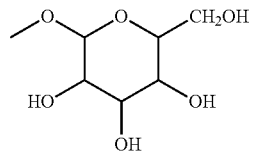

(e)

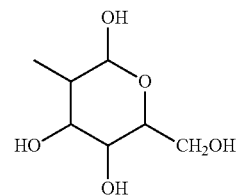

(f)

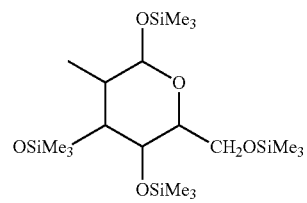

(g)

-continued

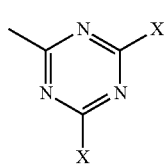

(h)

wherein X is halogen and/or optionally said radicals comprise 1 to 8 groups chosen from, alone or as a mixture, —S—, S(O), SO$_2$, —NH— (or =NH), —N=(trivalent), —O—, —C(O)—, —C(=NH)—, —N$^+$(CH$_3$)$_2$-An$^-$ (An$^-$: anion)n.

2. The method according to claim 1, in which R1 represents H and R2 represents H, CH$_3$, C$_7$H$_{15}$, C$_{13}$H$_{27}$ or aryl.

3. The method according to claim 1, in which the compounds of formula (I) are chosen from the following compounds:

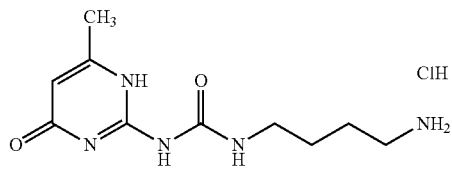

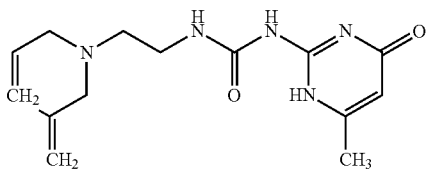

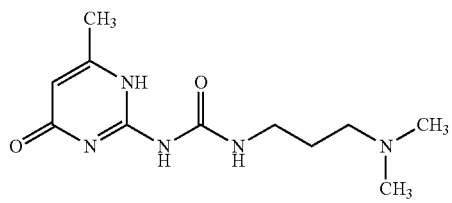

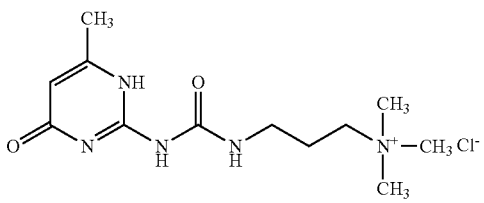

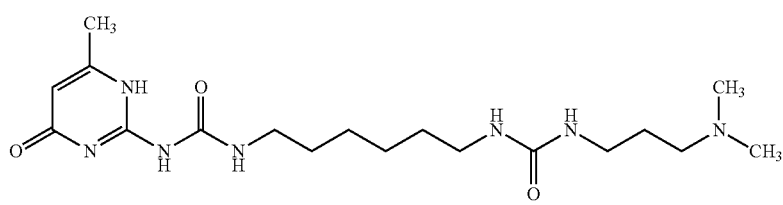

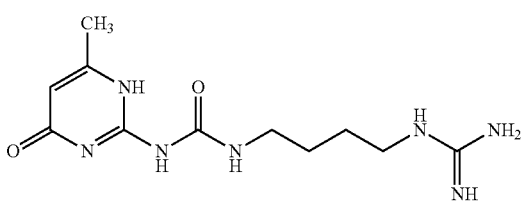

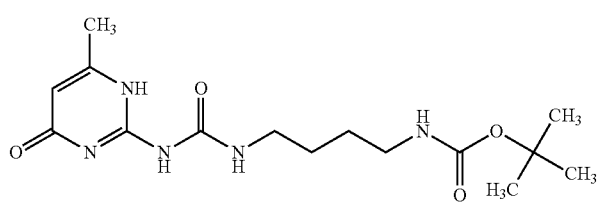

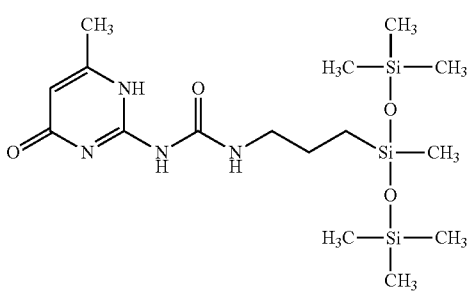

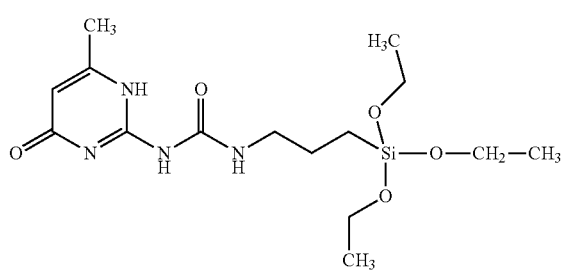

-continued
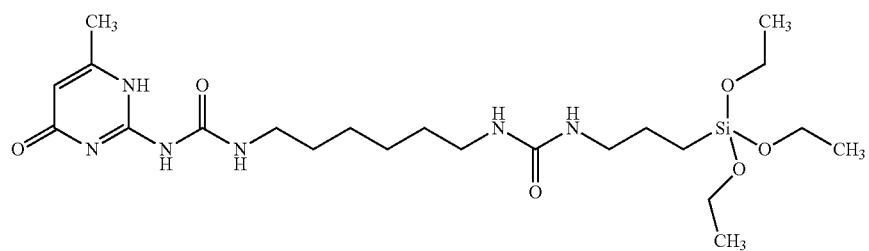
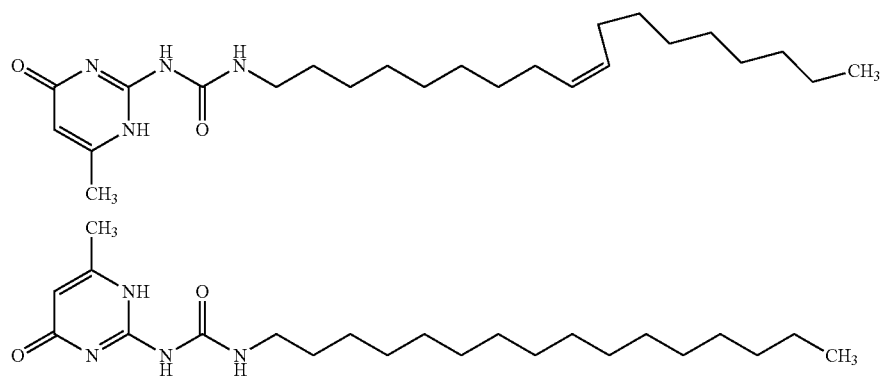
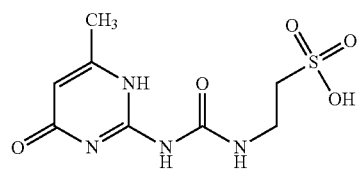
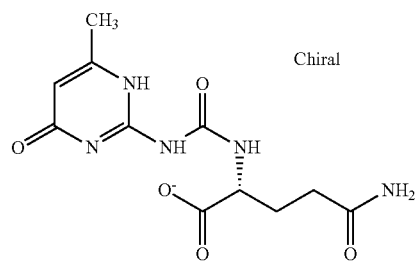
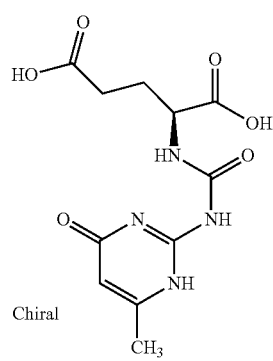
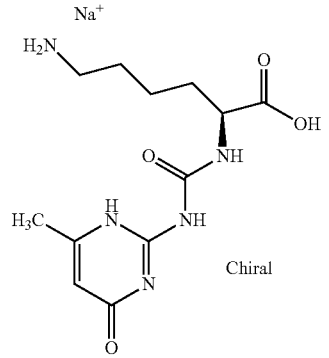
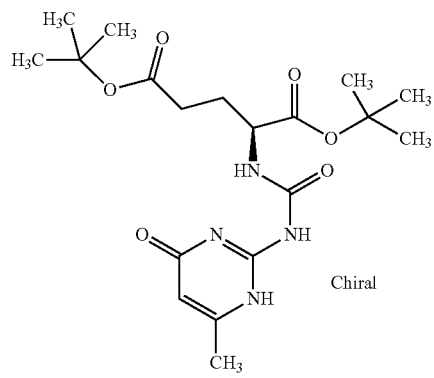
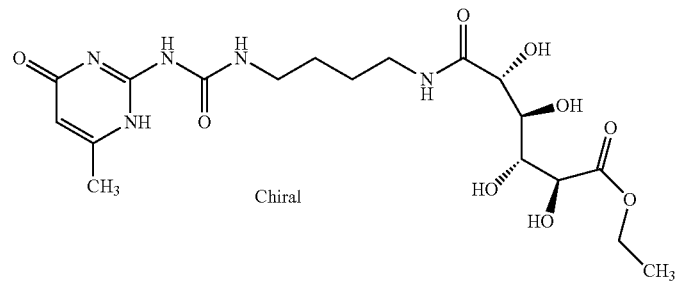

-continued
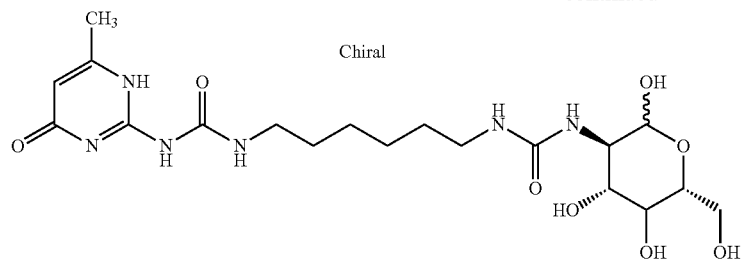
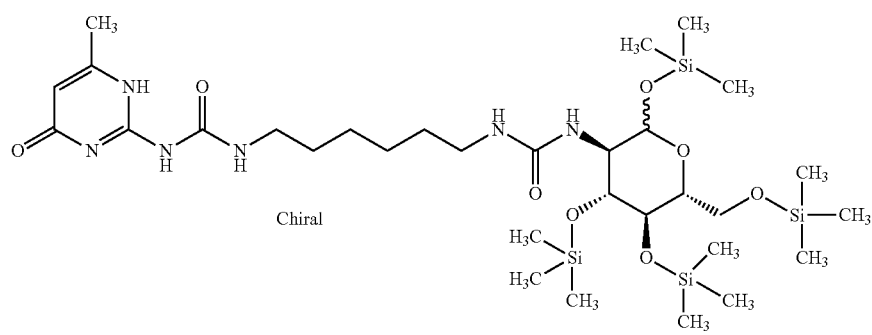
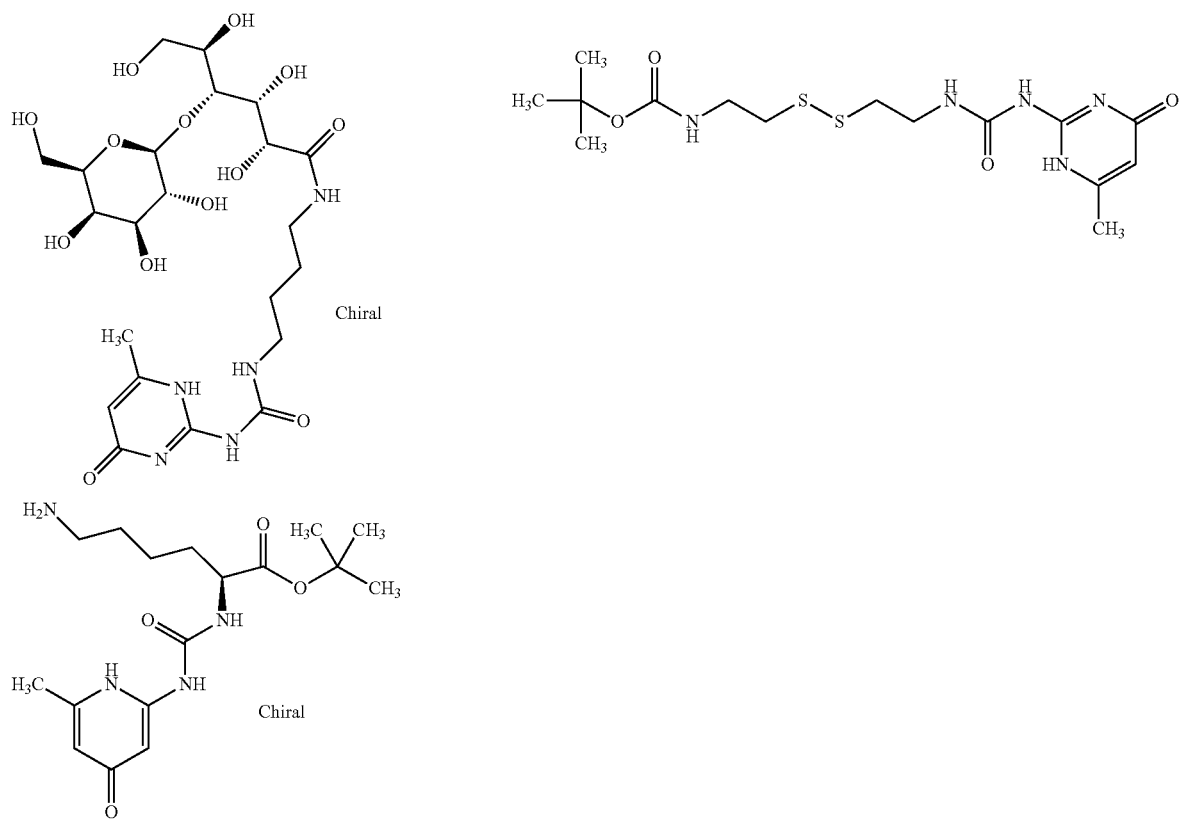

-continued
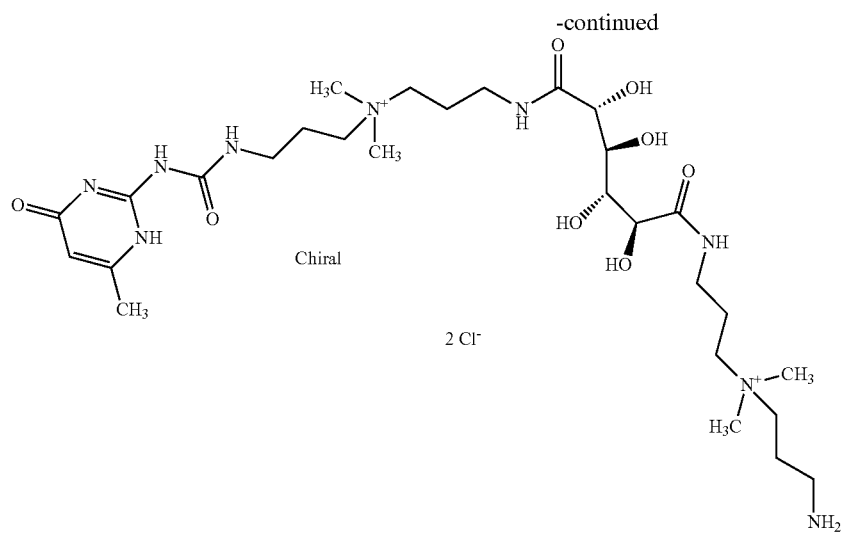
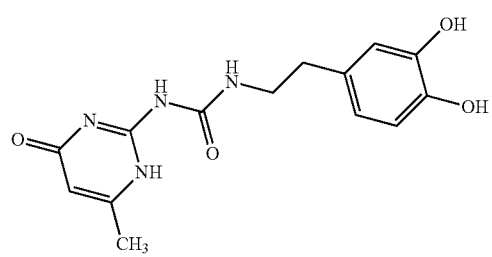
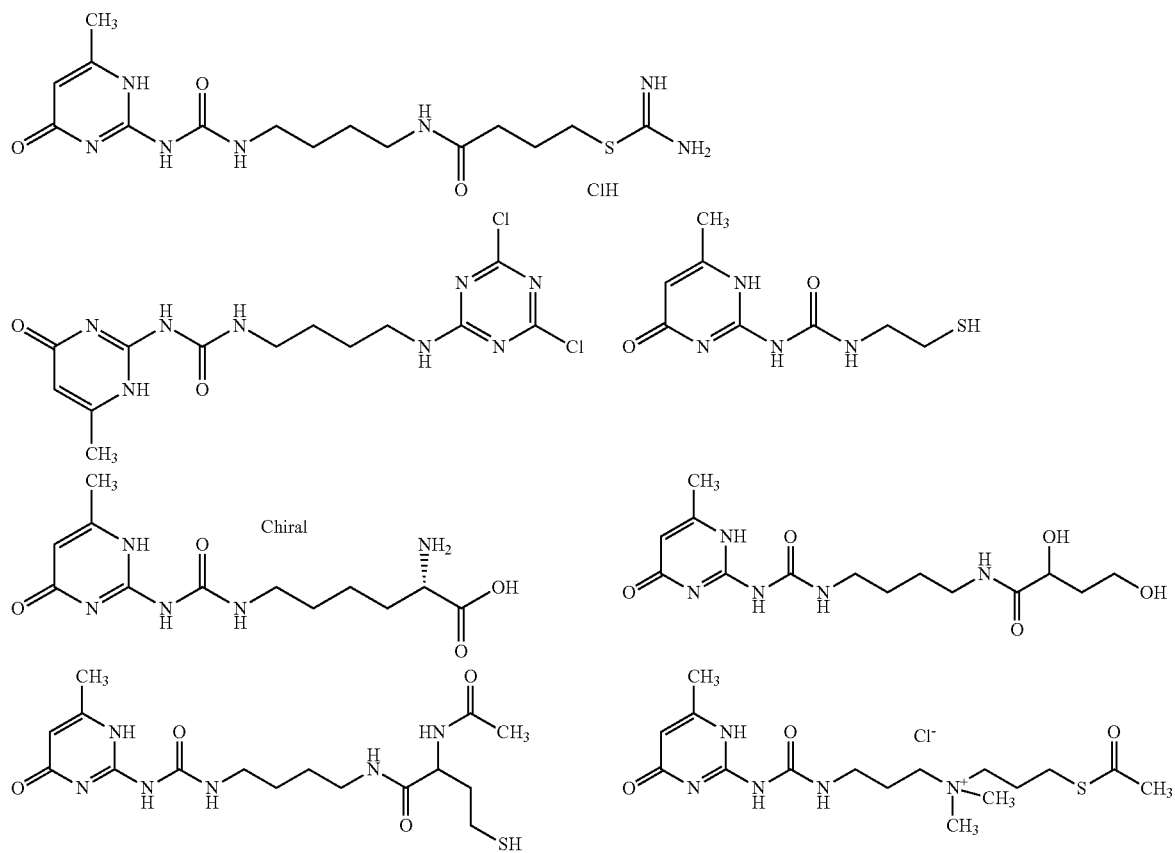

-continued

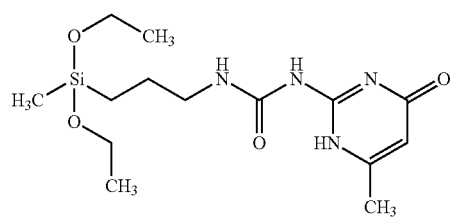

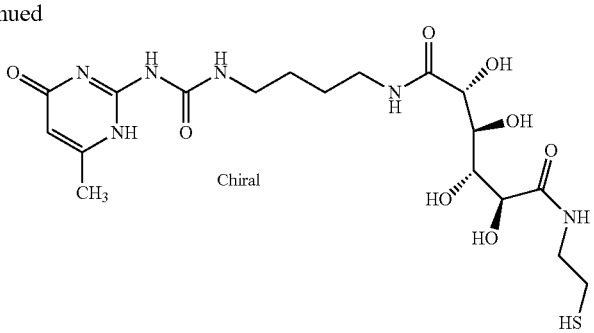

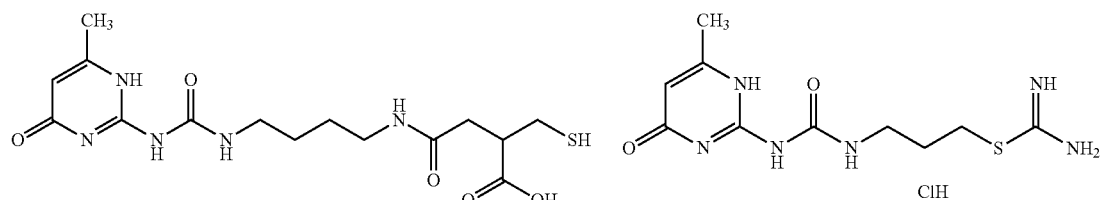

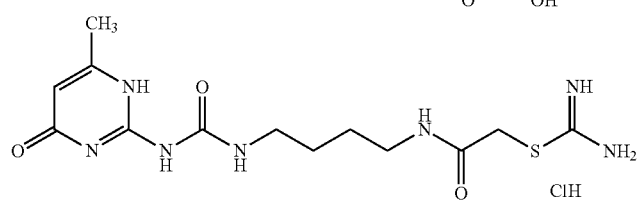

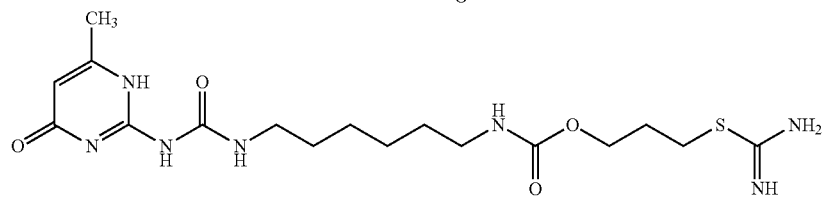

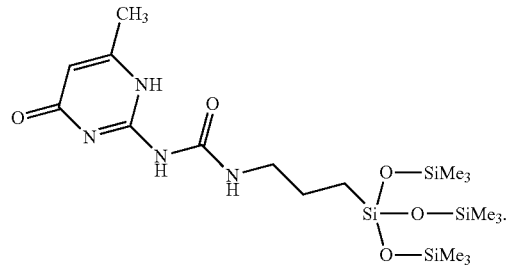

4. The method according to claim 1, in which the compound of formula (I), alone or as a mixture, is present in an amount between 0.001% and 30% by weight relative to the total weight of the composition relative to the total weight of the composition.

5. The method according to claim 1, wherein the composition further comprises at least one additional compound of formula (II):

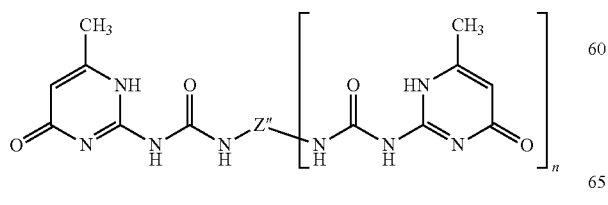

in which:

n=1 or 2, and

Z represents a divalent or trivalent (depending on the value of n), linear or branched C1-C32 alkyl or C2-C32 alkenyl radical;

optionally substituted with 1 to 10 radicals chosen from —OH, —SO₃H, —COOH, —COOR and —N⁺R'R", with each R, R' and R" individually being C1-C12 alkyl, and/or optionally interrupted by 1 to 10 groups chosen from (i) the divalent groups: —S—, —NH— (or =NH), —O—, —C(O)—, or of formula:

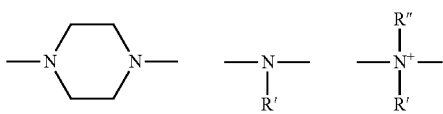

-continued

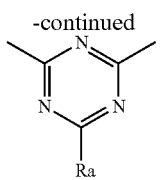

with Ra=H or halogen, or $C_1$-$C_6$ alkyl, or single bond, and

R' and R", which may be identical or different, representing a hydrogen atom or a C1-C6 alkyl radical; and (ii) the trivalent groups of formula:

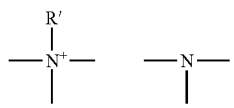

R' representing a hydrogen atom or a C1-C6 alkyl radical.

6. The method according to claim 5, in which the compound of formula (II), alone or as a mixture, is present in an amount between 0.001% and 30% by weight, relative to the total weight of the composition.

7. The method according to claim 1, in which the cosmetically acceptable medium comprises at least one ingredient chosen from propellants; water, carbon-based oils; silicone oils; C8-C40 alcohols, C8-C40 esters, C8-C40 acids; C1-C7 alcohols, ketones, organic solvents, nonionic surfactants, cationic surfactants, anionic surfactants, amphoteric surfactants, zwitterionic surfactants; sunscreens; moisturizers; antidandruff agents; antioxidants; reducing agents; oxidation bases, couplers, oxidizing agents, direct dyes; hair straightening agents, pearlescent agents and opacifying agents; plasticizers or coalescence agents; hydroxy acids; pigments; fillers; silicones; polyols; waxes; thickeners, emulsifiers; polymers; preservatives, and pH agents.

8. The method according to claim 1, wherein the composition is in the form of a product for caring for, cleansing and/or making up bodily or facial skin, the lips, the eyebrows, the eyelashes, the nails and the hair, an antisun or self-tanning product, a body hygiene product, or a haircare product, especially for caring for, cleansing, conditioning or colouring the hair.

9. The method according to claim 1, wherein the composition is in the form of a haircare composition, for the care and cosmetic treatment.

10. The method according to claim 1, for conditioning and/or caring for the hair.

11. The method according to claim 2, in which the compound of formula (I), alone or as a mixture, is present in an amount between 0.001% and 30% by weight relative to the total weight of the composition.

12. The method according to claim 2, wherein the composition further comprises at least one additional compound of formula (II):

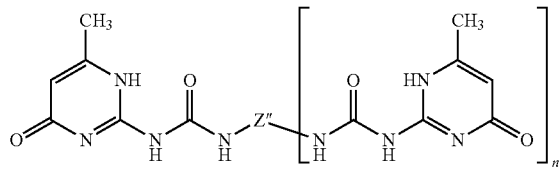

in which:
n=1 or 2, and
Z represents a divalent or trivalent (depending on the value of n), linear or branched C1-C32 alkyl or C2-C32 alkenyl radical;

optionally substituted with 1 to 10 radicals chosen from —OH, —SO$_3$H, —COOH, —COOR and —N$^+$R'R", with R, R' and R"=C1-C12 alkyl, and/or optionally interrupted by 1 to 10 groups chosen from (i) the divalent groups: —S—, —NH— (or =NH), —O—, —C(O)—, or of formula:

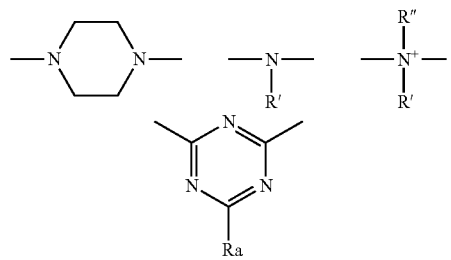

with Ra=H or halogen, or C1-C6 alkyl, or single bond, and

R' and R", which may be identical or different, representing a hydrogen atom or a C1-C6 alkyl radical; and (ii) the trivalent groups of formula:

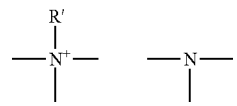

R' representing a hydrogen atom or a C1-C6 alkyl radical.

13. The method according to claim 2, in which the cosmetically acceptable medium comprises at least one ingredient chosen from propellants; water, carbon-based oils; silicone oils; C8-C40 alcohols, C8-C40 esters, C8-C40 acids; C1-C7 alcohols, ketones, organic solvents, nonionic surfactants, cationic surfactants, anionic surfactants, amphoteric surfactants, zwitterionic surfactants; sunscreens; moisturizers; antidandruff agents; antioxidants; reducing agents; oxidation bases, couplers, oxidizing agents, direct dyes; hair straightening agents, pearlescent agents and opacifying agents; plasticizers or coalescence agents; hydroxy acids; pigments; fillers; silicones; polyols; waxes; thickeners, emulsifiers; polymers; preservatives, pH agents.

14. The method according to claim 3, in which the compound of formula (I), alone or as a mixture, is present in an amount between 0.001% and 30% by weight relative to the total weight of the composition.

15. The method according to claim 3, wherein the composition further comprises at least one additional compound of formula (II):

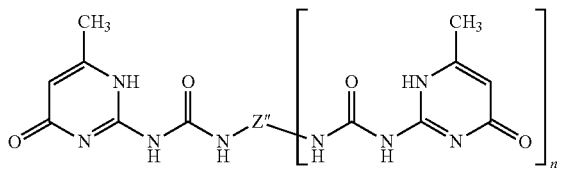

in which:

n=1 or 2, and

Z represents a divalent or trivalent (depending on the value of n), linear or branched C1-C32 alkyl or C2-C32 alkenyl radical;

optionally substituted with 1 to 10 radicals chosen from —OH, —SO₃H, —COOH, —COOR and —N⁺RR'R", with R, R' and R"=C1-C12 alkyl, and/or optionally interrupted by 1 to 10 groups chosen from (i) the divalent groups: —S—, —NH— (or =NH), —O—, —C(O)—, or of formula:

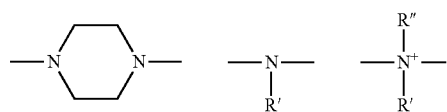

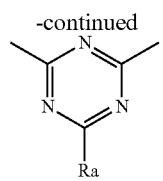

with Ra=H or halogen, or C1-C6 alkyl, or single bond, and

R' and R", which may be identical or different, representing a hydrogen atom or a C1-C6 alkyl radical; and (ii) the trivalent groups of formula:

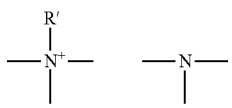

R' representing a hydrogen atom or a C1-C6 alkyl radical.

16. The method according to claim 4, in which the compounds of formula (I) are chosen from the following compounds:

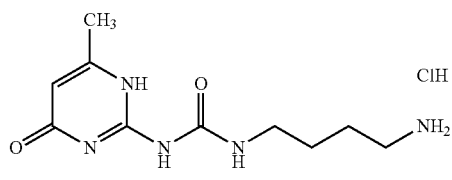
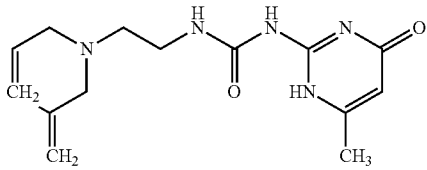
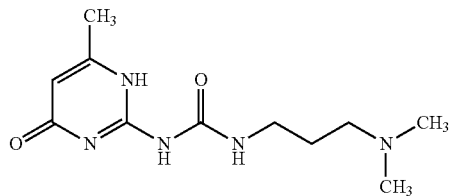
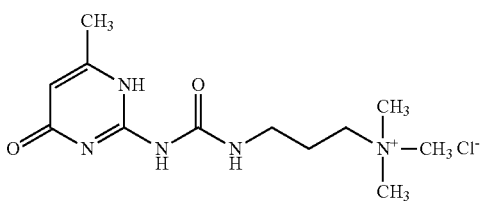
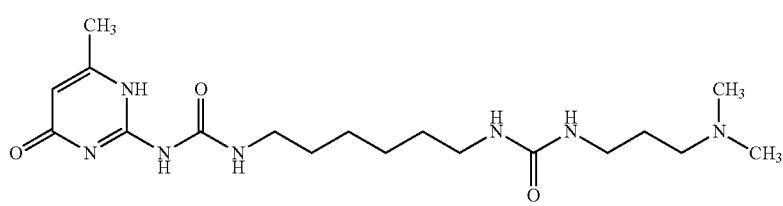
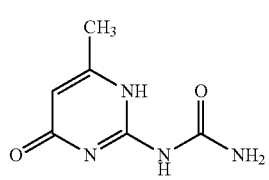
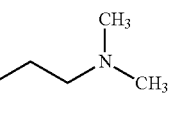
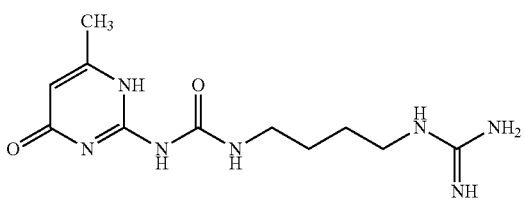
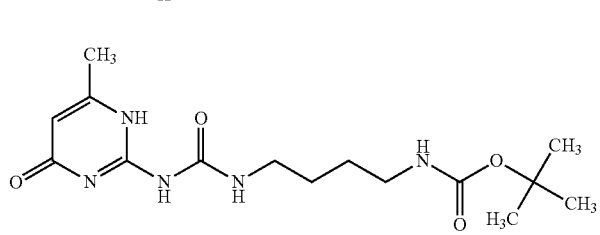
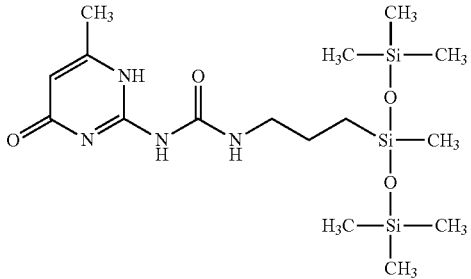

-continued
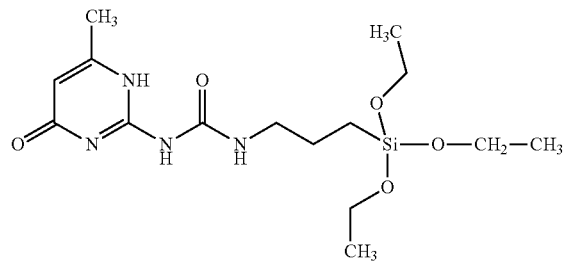
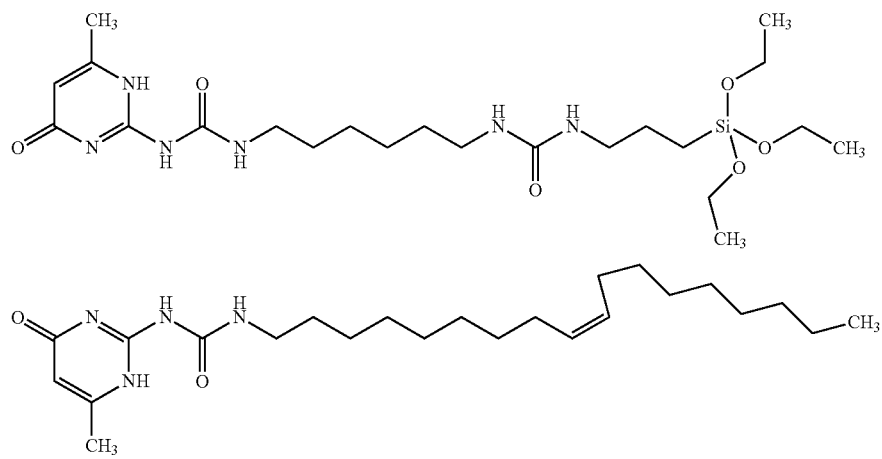
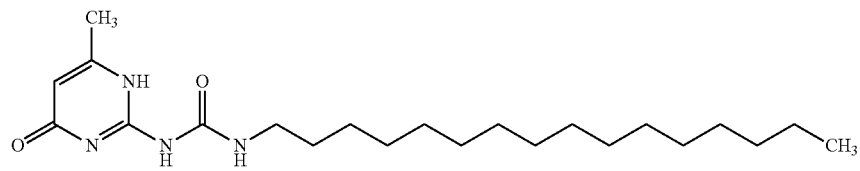
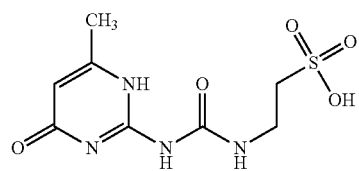
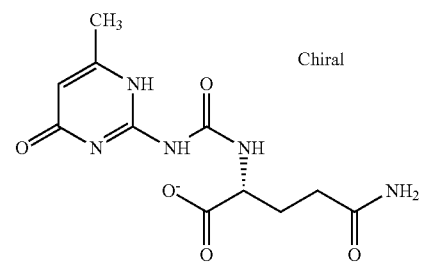
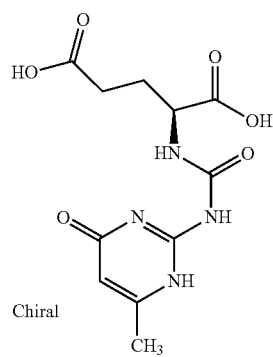
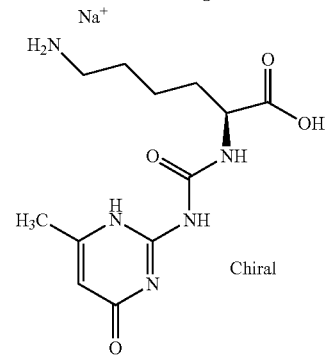

87
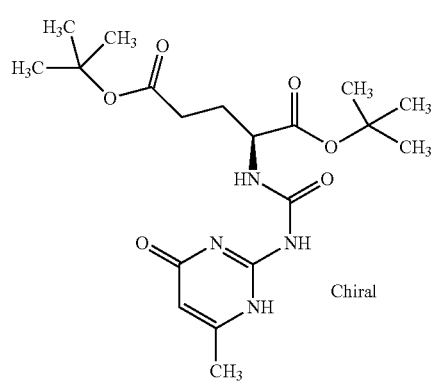
Chiral
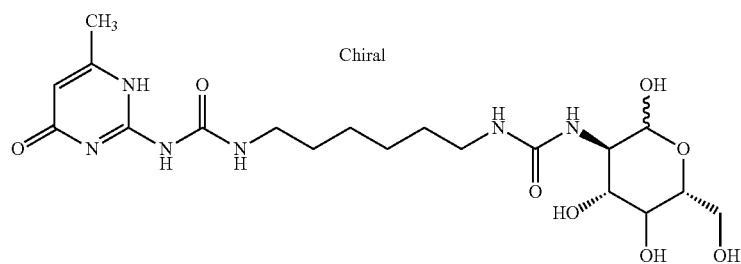
Chiral
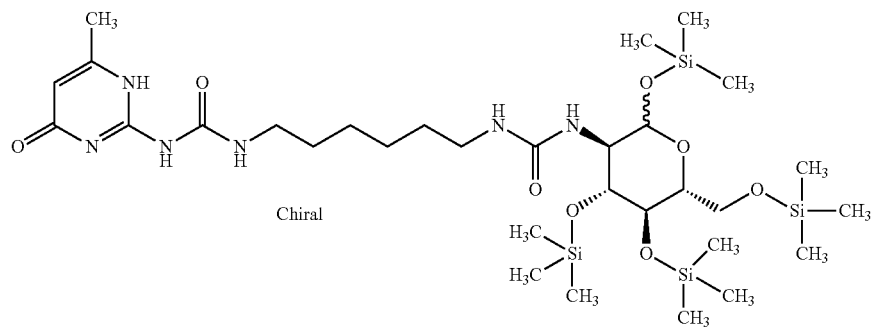
Chiral
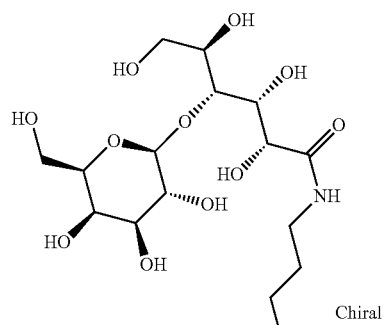
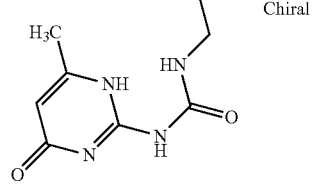
Chiral
88
-continued
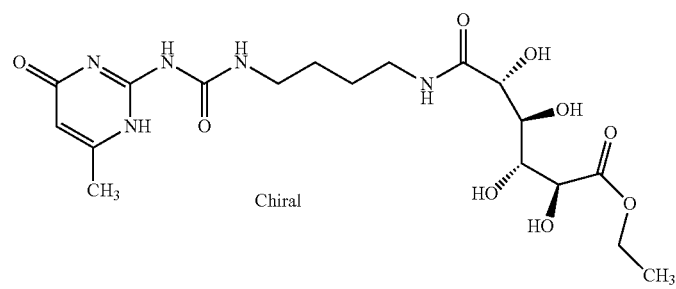
Chiral
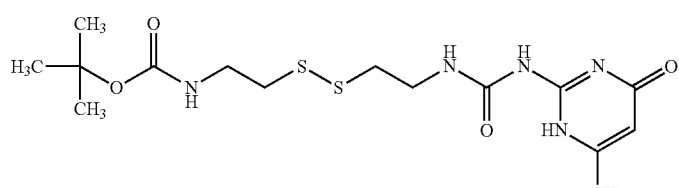

-continued
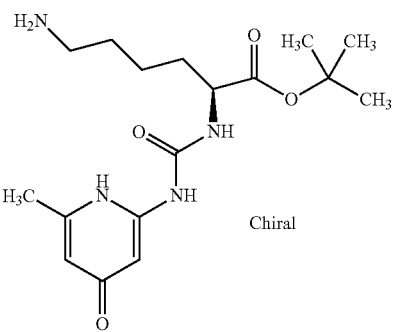
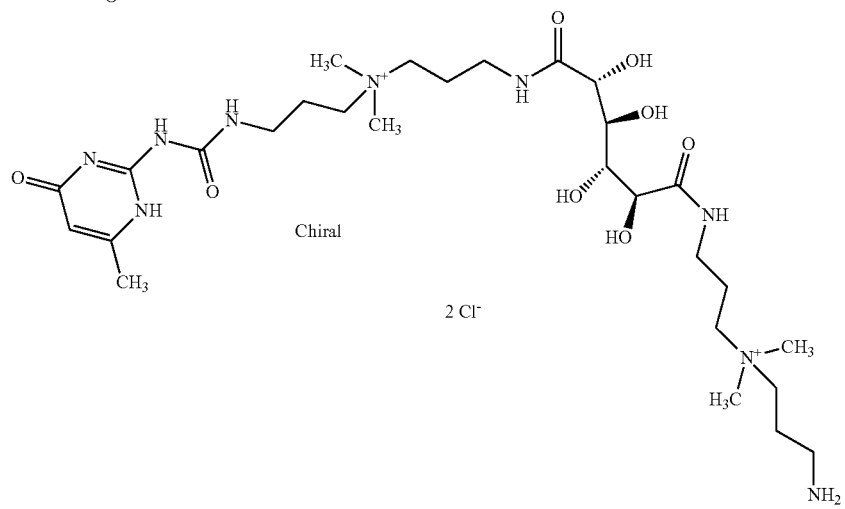
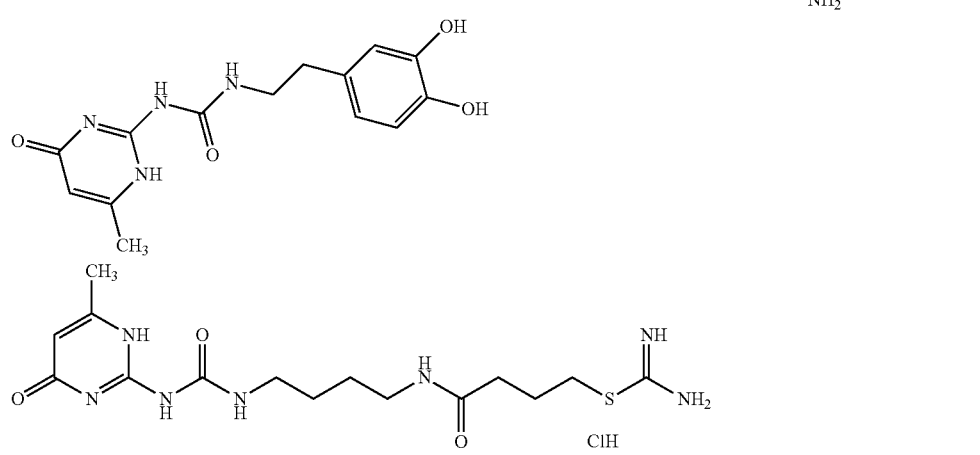
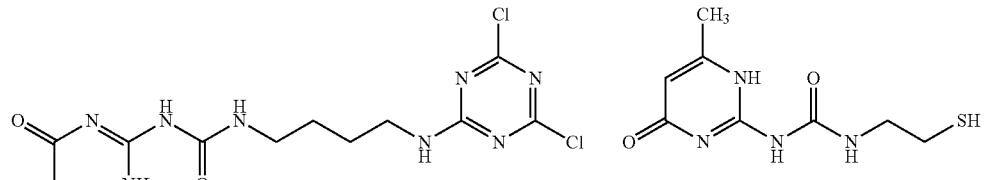
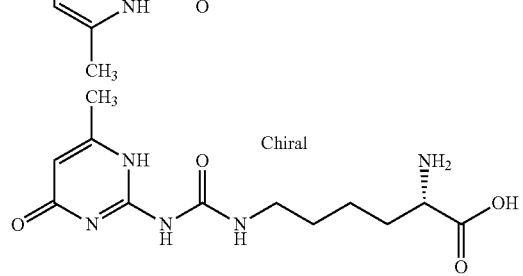
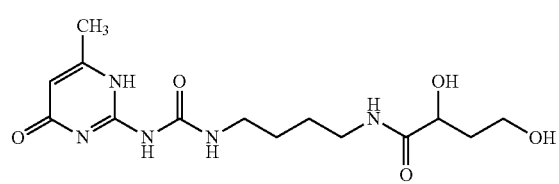

91 92
-continued
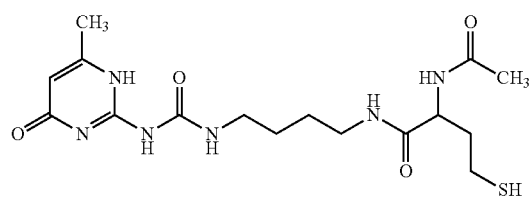 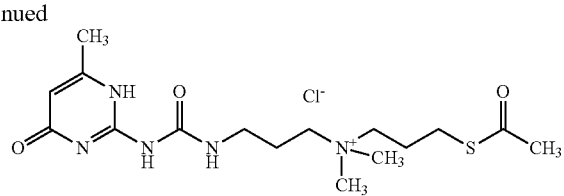
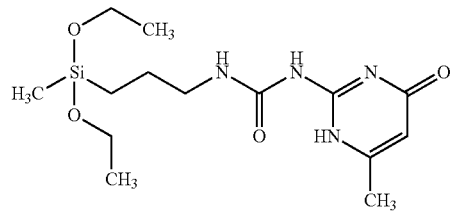 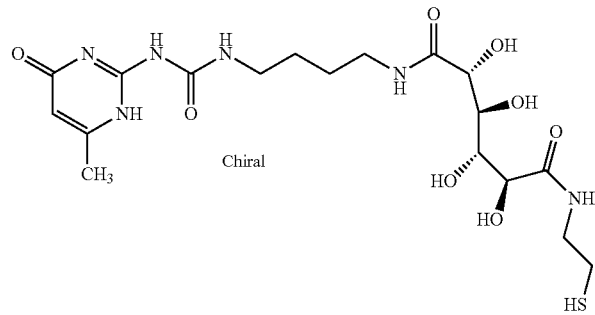
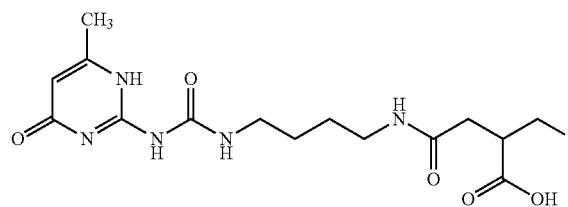 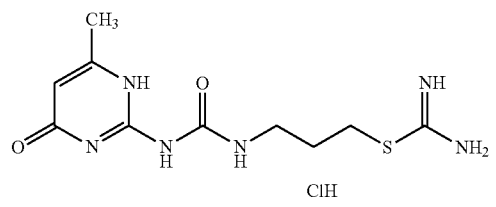
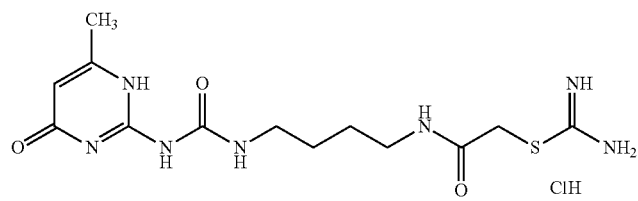
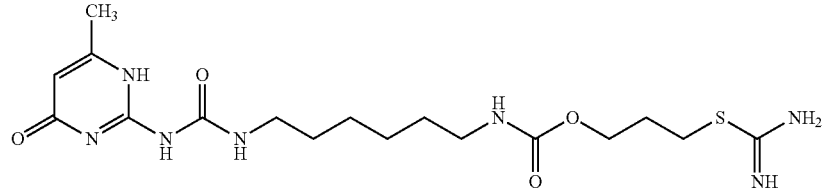
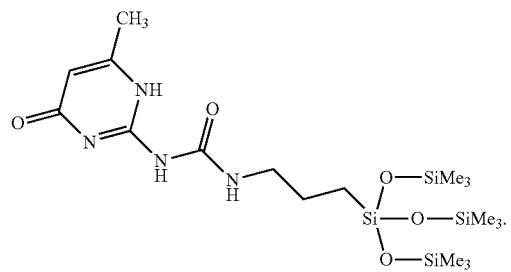

17. The method according to claim 4, wherein the composition further comprises at least one additional compound of formula (II):

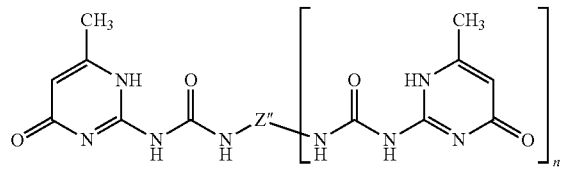

in which:

n=1 or 2, and

Z represents a divalent or trivalent (depending on the value of n), linear or branched C1-C32 alkyl or C2-C32 alkenyl radical;

optionally substituted with 1 to 10 radicals chosen from —OH, —SO$_3$H, —COOH, —COOR and —N$^+$RR'R", with R, R' and R"=C1-C12 alkyl, and/or optionally interrupted by 1 to 10 groups chosen from (i) the divalent groups: —S—, —NH— (or =NH), —O—, —C(O)—, or of formula:

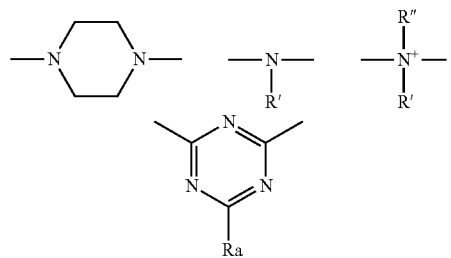

with Ra=H or halogen, or C1-C6 alkyl, or single bond, and

R' and R", which may be identical or different, representing a hydrogen atom or a C1-C6 alkyl radical; and (ii) the trivalent groups of formula:

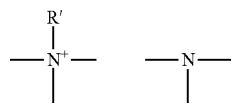

R' representing a hydrogen atom or a C1-C6 alkyl radical.

* * * * *